US007758874B2

(12) United States Patent
Jacobs, Jr. et al.

(10) Patent No.: US 7,758,874 B2
(45) Date of Patent: Jul. 20, 2010

(54) **ATTENUATED *MYCOBACTERIUM TUBERCULOSIS* VACCINES**

(75) Inventors: William R. Jacobs, Jr., Pelham, NY (US); Barry Bloom, Cambridge, MA (US); Mary K. Hondalus, Crawford, GA (US); Samantha Sampson, Brookline, MA (US); Vasan Sambandamurthy, Bronx, NY (US)

(73) Assignees: Albert Einstein College of Medicine of Yeshiva University, Bronx, NY (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/109,056

(22) Filed: Apr. 19, 2005

(65) Prior Publication Data

US 2005/0260232 A1 Nov. 24, 2005

Related U.S. Application Data

(63) Continuation-in-part of application No. 10/351,452, filed on Jan. 24, 2003.

(60) Provisional application No. 60/358,152, filed on Feb. 19, 2002.

(51) Int. Cl.
*A61K 39/04* (2006.01)
*A61K 49/00* (2006.01)
*A61K 39/00* (2006.01)

(52) U.S. Cl. ...................... 424/248.1; 424/9.1; 424/9.2; 424/184.1; 424/185.1; 424/234.1; 424/190.1; 435/243; 435/253.1; 536/23.1; 536/23.7

(58) Field of Classification Search .................. 424/9.1, 424/9.2, 93.2, 184.1, 185.1, 190.1, 234.1, 424/248.1; 435/243, 253.1, 440; 536/23.1, 536/23.7

See application file for complete search history.

(56) References Cited

U.S. PATENT DOCUMENTS

| | | | |
|---|---|---|---|
| 5,750,384 | A | 5/1998 | Jacobs, Jr. et al. |
| 5,837,732 | A | 11/1998 | Sacchettini et al. |
| 5,955,077 | A | 9/1999 | Andersen et al. |
| 5,968,733 | A | 10/1999 | Bloom et al. |
| 5,972,700 | A | 10/1999 | Jacobs et al. |
| 6,015,890 | A | 1/2000 | Jacobs, Jr. et al. |
| 6,221,364 | B1 | 4/2001 | Pavelka et al. |
| 6,221,365 | B1 | 4/2001 | Jones |
| 6,268,201 | B1 | 7/2001 | Alland et al. |
| 6,271,034 | B1 | 8/2001 | Bardarov et al. |
| 6,290,966 | B1 | 9/2001 | Cox et al. |
| 6,291,190 | B1 | 9/2001 | Behr et al. |
| 6,387,694 | B1 | 5/2002 | McKinney et al. |
| 6,423,545 | B1 | 7/2002 | Pavelka et al. |
| 6,562,348 | B2 | 5/2003 | Hondulus et al. |
| 6,566,121 | B1 | 5/2003 | Jacobs, Jr. et al. |
| 6,733,761 | B2 | 5/2004 | McKinney et al. |
| 6,752,994 | B2 | 6/2004 | Jacobs, Jr. et al. |
| 6,821,769 | B2 | 11/2004 | Alland et al. |
| 2003/0059441 | A1 | 3/2003 | Pavelka et al. |
| 2004/0001866 | A1 | 1/2004 | Jacobs et al. |

FOREIGN PATENT DOCUMENTS

| | | | |
|---|---|---|---|
| WO | WO 03/070164 | A2 | 8/2003 |
| WO | WO 2006/076343 | A1 | 7/2006 |
| WO | WO 2006/076517 | A1 | 7/2006 |
| WO | WO 2006/076519 | A2 | 7/2006 |

OTHER PUBLICATIONS

Collins, F.M. "Immunogenicity of various mycobacteria and the corresponding levels of cross-protection developed between species." Infection and Immunity, vol. 4, No. 6, pp. 688-696, Dec. 1971.*

Collins, D.M. Immunology and Cell Biology, 2000, vol. 78, No. 4, pp. 342-348.*

Andersen, P., "Host Responses and Antigens Involved in Protective Immunity to Mycobacterium tuberculosis"; Scand. J. Immunol. 1997, pp. 115-131, vol. 45.

Andersen, P., et al., "Proteins Released from Mycobacterium tuberculosis during Growth"; Infection and Immunity, Jun. 1991, pp. 1905-1910, vol. 59, No. 6.

Behr, M.A., et al., "Comparative Genomics of BCG Vaccines by Whole-Genome DNA Microarray"; Science, May 28, 1999, pp. 1520-1523, vol. 284.

(Continued)

*Primary Examiner*—Rodney P. Swartz
(74) *Attorney, Agent, or Firm*—Amster, Rothstein & Ebenstein LLP

(57) ABSTRACT

Non-naturally occurring mycobacteria in the *Mycobacterium tuberculosis* complex are provided. These mycobacteria have a deletion of an RD1 region or a region controlling production of a vitamin, and exhibit attenuated virulence in a mammal when compared to the mycobacteria without the deletion. Also provided are non-naturally occurring mycobacteria that have a deletion of a region controlling production of lysine, and mycobacteria comprising two attenuating deletions. Vaccines comprising these mycobacteria are also provided, as are methods of protecting mammals from virulent mycobacteria using the vaccines. Also provided are methods of preparing these vaccines which include the step of deleting an RD1 region or a region controlling production of a vitamin or the amino acids leucine and lysine from a mycobacterium in the *M. tuberculosis* complex. Embodiments of these mycobacteria, vaccines and methods, encompassing mycobacteria comprising a leucine auxotrophy and a pantothenate auxotrophy, are also provided.

16 Claims, 29 Drawing Sheets

OTHER PUBLICATIONS

Camacho, L.R., et al., "Identification of a virulence gene cluster of Mycobacterium tuberculosis by signature-tagged transposon mutagenesis"; Molecular Microbiology, 1999, pp. 257-267, vol. 34.
Chambers. M.A. et al., "Identification of a *Mycobacterium bovis* BCG Auxotrophic Mutant That Protects Guinea Pigs against *M. bovis* and Hematogenous Spread of *Mycobacterium tuberculosis* without Sensitization to Tuberculin"; Infection and Immunity, Dec. 2000, pp. 7094-7099, vol. 68, No. 12.
Cole, S.T., et al., "Deciphering the biology of *Mycobacterium tuberculosis* from the complete genome sequence"; Nature, Jun. 11, 1998, pp. 537-544 + table pages, vol. 393.
Cox, J., et al., "Complex lipid determines tissue-specific replication of Mycobacterium tuberculosis in mice"; Nature, Nov. 4, 1999, pp. 79-83, vol. 402.
Dascher C.C. et al., "Immunization with a mycobacterial lipid vaccine Improves pulmonary pathology in the guinea pid model of tuberculosis"; International Immunology, Aug. 2003, pp. 915-925, vol. 15, No. 8.
De Voss, J.J., et al. "The salicylate-derived mycobactin siderophores of Mycobacterium tuberculosis are essential for growth in macrophages"; PNAS, Feb. 1, 2000, pp. 1252-1257, vol. 97, No. 3.
Glickman, M.S., et al., "The *Mycobacterium tuberculosis* cmaA2 Gene Encodes a Mycolic Acid trans-Cyclopropane Synthetase"; The Journal of Biological Chemistry, Jan. 19, 2001, pp. 2228-2233, vol. 276, No. 3.
Gordon, S.V., et al., "Genomics of *Mycobacterium bovis*"; Tuberculosis, 2001, pp. 157-163, vol. 81(1/2).
Guleria, I., et al., "Auxotrophic vaccines for tuberculosis"; Nature Medicine, Mar. 1996, pp. 334-337, vol. 2, No. 3.
Harboe M. et al., "Evidence for Occurance of the ESAT-6 Protein in Mycobacterium tuberculosis and Virulent *Mycobacterium bovis* and for Its Absence in *Mycobacterium bovis* BCG"; Infection and Immunity. Jan. 1996, pp. 16-22, vol. 64, No. 1.
Hernandez-Pando R. et al., "Pathogenesis of Tuberculosis in Mice Exposed to Low and High Doses of an Environmental Mycobacterial Saprophtye before Infection"; Infection and Immunity, Aug. 1997, pp. 3317-3327, vol. 65, No. 8.
Hondalus, M.K., et al., "Attenuation of and Protection Induced by a Leucine Auxotroph of *Mycobacterium tuberculosis*"; Infection and Immunity, May 2000, pp. 2888-2898, vol. 68, No. 5.
Jackson, M., et al., "Persistence and Protective Efficacy of a *Mycobacterium tuberculosis* Auxotroph Vaccine"; Infection and Immunity, Jun. 1999, pp. 2867-2873, vol. 67, No. 6.
Mahairas, G.G., et al., "Molecular Analysis of Genetic Differences between *Mycobacterium bovis* BCG an Virulent *M. bovis*"; Journal of Bacteriology, Mar. 1996, pp. 1274-1282, vol. 178, No. 5.
Manca, C., et al., "Virulence of a *Mycobacterium tuberculosis* clinical isolate in mice is determined by failure to induce Th1 type immunity and is associated with induction of IFN-alpha/beta"; PNAS, May 8, 2001, pp. 5752-5757, vol. 98, No. 10.
McKinney, J.D., et al., "Persistence of *Mycobacterium tuberculosis* in macrophages and mice requires the glyoxylate shunt enzyme isocitrate lyase"; Nature, Aug. 17, 2000, pp. 735-738, vol. 406.
Moreira A.L. et al., "Mycobacterial Antigens Exacerbate Disease Manifestations in *Mycobacterium tuberculosis*-Infected Mice"; Infection and Immunity, Apr. 2002, pp. 2100-2107, vol. 70, No. 4.
Pavelka, Jr., M.S. and Jacobs, Jr., W.R., "Comparison of the Construction of Unmarked Deletion Mutations in *Mycobacterium smegmatis, Mycobacterium bovis*, Bacillus Calmette-Guerin, and *Mycobacterium tuberculosis* H37Rv by Allelic Exchange", Journal of Bacteriology, Aug. 1999, pp. 4780-4789, vol. 181, No. 16.
Sambandamurthy V.K. et al., "A pantothenate auxotroph of *Mycobacterium tuberculosis* is highly attenuated and protects mice against tuberculosis"; Nature Medicine, Oct. 2002, pp. 1171-1174, vol. 8, No. 10.
Sambandamurthy V.K. et al., "Long-Term Protection against Tuberculosis following Vaccination with a Severely Attenuated Double Lysine and Pantothenate Auxotroph of *Mycobacterium tuberculosis*"; Infection and Immunity, Feb. 2005, pp. 1196-1203, vol. 73, No. 2.
Sampson S.L. et al., "Protection Elicited by a Double Leucine and Pantothenate Auxotroph of *Mycobacterium tuberculosis* in Guinea Pigs"; Infection and Immunity, May 2004, pp. 3031-3037, vol. 72, No. 5.
Skinner M.A. et al., "A DNA prime-live vaccine boost strategy in mice can augment IFN-gamma responses to mycobacterial antigens but does not increase the protective efficacy of two attenuated strains of *Mycobacterium bovis* against bovine tuberculosis"; Immunology, Apr. 2003, pp. 548-555, vol. 108, No. 4.
Slyshenkov, V.S., et al., "Pantothenic Acid and Its Derivatives Protect Ehrlich Ascites Tumor Cells Against Lipid Peroxidation"; Free Radical Biology & Medicine, 1995, pp. 767-772, vol. 19, No. 6.
Smith, D.A., et al. "Characterization of Auxotrophic Mutants of *Mycobacterium tuberculosis* and Their Potential as Vaccine Candidates"; Infection and Immunity, Feb. 2001, pp. 1142-1150, vol. 69, No. 2.
Taylor J.L. et al., "Pulmonary Necrosis Resulting from DNA Vaccination against Tuberculosis"; Infection and Immunity, Apr. 2003, pp. 2192-2198, vol. 71, No. 4.
Amendment dated Jul. 8, 2009 for U.S. Appl. No. 10/351,452.
Brennan et al. "Tuberculosis vaccine development: research, regulatory and clinical strategies." Expert Opin. Biol. Ther., vol. 4, No. 9, pp. 1493-1504, 2004.
Orme, "Beyond BCG: the potential for a more effective TB vaccine." Molecular Medicine Today, vol. 5, pp. 487-492, 1999.
Collins, "New generation tuberculosis vaccines," Clinical Microbilogy Newsletter, vol. 23, No. 3, pp. 17-23, 2001.
Hsu at al. "The primary mechanism of attenuation of bacillus Calmette-Guérin is a loss of secreted lytic function required for invasion of lung interstitial tissue." PNAS, Oct. 2003, pp. 1240-1225, vol. 100, No. 21.
Ladel et al. "Immune response to *Mycobacterium bovis* bacille Calmette-Guérin infection in major histocompatibility complex class I- and II-deficient knock-out mice: contribution of CD4 and CD 8 T cells to acquired resistance." Eur. J. Immunol., 1995, pp. 377-384, vol. 25.
Mogues et al. "The relative importance of T cells subsets in immunity and immunopathology of airborn mycobacterium tuberculosis infection in mice." J. Exp. Med., Feb. 2001, pp. 271-280, vol. 193, No. 3.
Slyshenkov et al. "Pantothenic acid and its derivatives protect erlich ascites tumor cells against lipid peroxidation." Free Radical Bio. & Med. 1995, pp. 767-72, 108:4.
Weber et al, "Anaerobic nitrate reductase (narGHJI) activity of *Mycobacterium bovis* BCG in vitro and its contribution to virulence in immunodeficient mice." Molecular Microbiology, 2000, pp. 1017-25, vol. 35, No. 5.
The Office Action dated Nov. 5, 2009 for U.S. Appl. No. 10/542,958, filed Jan. 30, 2007.
Waters et al. "Failure of a *Mycobacterium tuberculosis* ΔRD1 ΔpanCD double deletion mutant in a neonatal calf aerosol *M. bovis* challenge model: Comparisons to responses elicited by *M. bovis* bacille Calmette Guerin." Vaccine 25 (2007) 7832-7840.

* cited by examiner

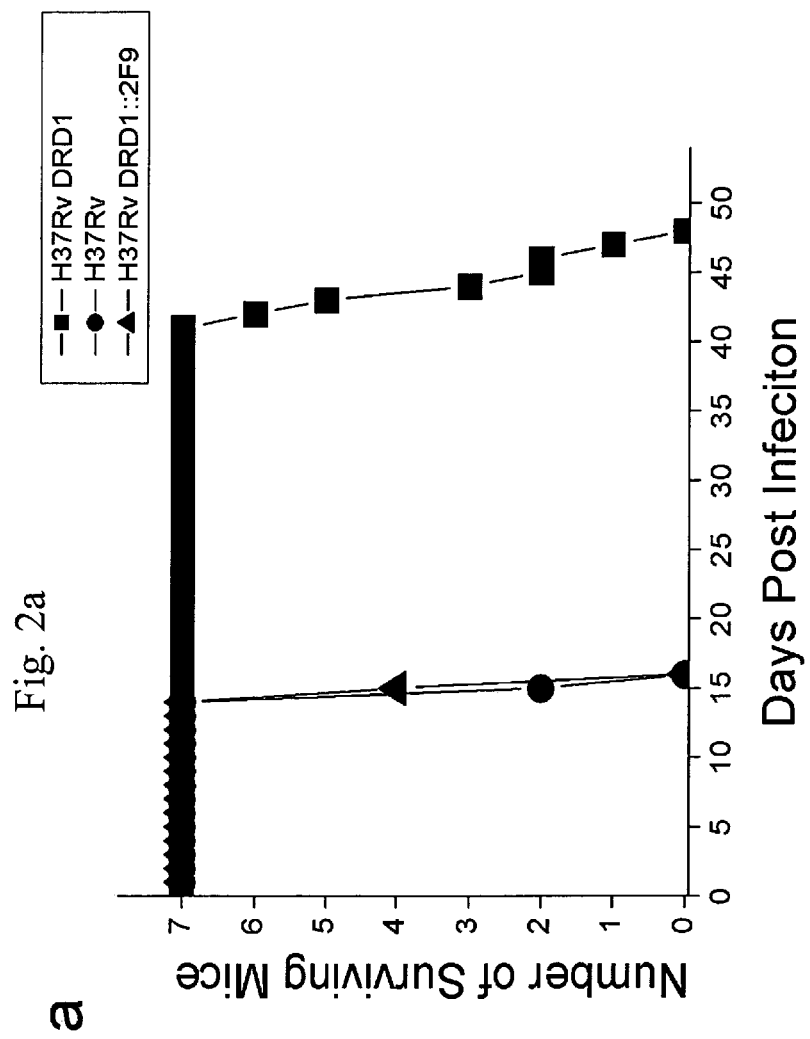

SEQUENCE LISTING

<160> NUMBER OF SEQ ID NOS: 12

<210> SEQ ID NO 1
<211> LENGTH: 9454
<212> TYPE: DNA
<213> ORGANISM: Mycobacterium tuberculosis

<400> SEQUENCE: 1

```
gatcgtgggt gccgccgggg ggatgccgcc gatggcaccg ctggccccgt tattgccggc      60
ggcggcagat atcggggttgc acatcattgt cacctgtcag atgagccagg cttacaaggc     120
aaccatggac aagttcgtcg gcgccgcatt cgggtcgggc gctccgacaa tgttcctttc     180
gggcgagaag caggaattcc catccagtga gttcaaggtc aagcggcgcc ccctggcca      240
ggcatttctc gtctcgccag acggcaaaga ggtcatccag gccccctaca tcgagcctcc      300
agaagaagtg ttcgcagcac ccccaagcgc cggttaagat tatttcattg ccggtgtagc      360
aggacccgag ctcagcccgg taatcgagtt cgggcaatgc tgaccatcgg gtttgtttcc      420
```

```
ggctataacc gaacggtttg tgtacgggat acaaatacag ggagggaaga agtaggcaaa    480
tggaaaaaat gtcacatgat ccgatcgctg ccgacattgg cacgcaagtg agcgacaacg    540
ctctgcacgg cgtgacggcc ggctcgacgg cgctgacgtc ggtgaccggg ctggttcccg    600
cgggggccga tgaggtctcc gcccaagcgg cgacggcgtt cacatcggag ggcatccaat    660
tgctggcttc caatgcatcg gcccaagacc agctccaccg tgcgggcgaa gcggtccagg    720
acgtcgcccg cacctattcg caaatcgacg acggcgccgc cggcgtcttc gccgaatagg    780
cccccaacac atcggaggga gtgatcacca tgctgtggca cgcaatgcca ccggagctaa    840
ataccgcacg gctgatggcc ggcgcgggtc cggctccaat gcttgcggcg ccgcgggat    900 ggcagacgct ttcggcggct ctggacgctc aggccgtcga gttgaccgcg cgcctgaact    960
ctctgggaga agcctggact ggaggtggca gcgacaaggc gcttgcggct gcaacgccga   1020
tggtggtctg gctacaaacc gcgtcaacac aggccaagac ccgtgcgatg caggcgacgg   1080
cgcaagccgc ggcatacacc caggccatgg ccacgacgcc gtcgctgccg gagatcgccg   1140
ccaaccacat cacccaggcc gtccttacgg ccaccaactt cttcggtatc aacacgatcc   1200
cgatcgcgtt gaccgagatg gattatttca tccgtatgtg gaaccaggca gccctggcaa   1260
tggaggtcta ccaggccgag accgcggtta acacgctttt cgagaagctc gagccgatgg   1320
cgtcgatcct tgatcccggc gcgagccaga gcacgacgaa cccgatcttc ggaatgccct   1380
cccctggcag ctcaacaccg gttggccagt tgccgccggc ggctacccag accctcggcc   1440
aactgggtga tgatgagcgg ccgatgcagc agctgaccca gccgctgcag caggtgacgt   1500
cgttgttcag ccaggtgggc ggcaccggcg gcggcaaccc agccgacgag gaagccgcgc   1560
agatgggcct gctcggcacc agtccgctgt cgaaccatcc gctggctggt ggatcaggcc   1620
ccagcgcggg cgcgggcctg ctgcgcgcgg agtcgctacc tggcgcaggt gggtcgttga   1680
cccgcacgcc gctgatgtct cagctgatcg aaaagccggt tgcccccctcg gtgatgccgg   1740 cggctgctgc cggatcgtcg gcgacgggtg gcgccgctcc ggtgggtgcg ggagcgatgg   1800
gccagggtgc gcaatccggc ggctccacca ggccgggtct ggtcgcgccg gcaccgctcg   1860
cgcaggagcg tgaagaagac gacgaggacg actgggacga agaggacgac tggtgagctc   1920
ccgtaatgac aacagacttc ccggccaccc gggccggaag acttgccaac attttggcga   1980
ggaaggtaaa gagagaaagt agtccagcat ggcagagatg aagaccgatg ccgctaccct   2040
cgcgcaggag gcaggtaatt tcgagcggat ctccggcgac ctgaaaaccc agatcgacca   2100
ggtggagtcg acggcaggtt cgttgcaggg ccagtggcgc ggcgcggcgg ggacggccgc   2160
ccaggccgcg gtggtgcgct tccaagaagc agccaataag cagaagcagg aactcgacga   2220
gatctcgacg aatattcgtc aggccggcgt ccaatactcg agggccgacg aggagcagca   2280
gcaggcgctg tcctcgcaaa tgggcttctg acccgctaat acgaaagaa acggagcaaa   2340 aacatgacag agcagcagtg gaatttcgcg ggtatcgagg ccgcggcaag cgcaatccag   2400
ggaaatgtca cgtccattca ttccctcctt gacgagggga agcagtccct gaccaagctc   2460
gcagcggcct ggggcggtag cggttcggag gcgtaccagg gtgtccagca aaaatgggac   2520
gccacggcta ccgagctgaa caacgcgctg cagaacctgg cgcggacgat cagcgaagcc   2580
ggtcaggcaa tggcttcgac cgaaggcaac gtcactggga tgttcgcata gggcaacgcc   2640
gagttcgcgt agaatagcga aacacgggat cgggcgagtt cgaccttccg tcggtctcgc   2700
cctttctcgt gtttatacgt ttgagcgcac tctgagaggt tgtcatggcg gccgactacg   2760
```

```
acaagctctt ccggccgcac gaaggtatgg aagctccgga cgatatggca gcgcagccgt   2820
tcttcgaccc cagtgcttcg tttcgccgg cgcccgcatc ggcaaaccta ccgaagccca    2880
acggccagac tccgccccg acgtccgacg acctgtcgga gcggttcgtg tcggccccgc    2940
cgccgccacc cccaccccca cctccgcctc cgccaactcc gatgccgatc gccgcaggag   3000
agccgccctc gccggaaccg gccgcatcta aaccacccac accccccatg cccatcgccg   3060
gacccgaacc ggccccaccc aaaccaccca caccccccat gccatcgcc ggacccgaac    3120 cggccccacc caaaccaccc acacctccga tgcccatcgc cggacctgca cccaccccaa   3180
ccgaatccca gttggcgccc cccagaccac cgacaccaca aacgccaacc ggagcgccgc   3240
agcaaccgga atcaccggcg ccccacgtac cctcgcacgg ccacatcaa ccccggcgca    3300 ccgcaccagc accgccctgg gcaaagatgc caatcggcga accccccgccc gctccgtcca  3360 gaccgtctgc gtccccggcc gaaccaccga cccggcctgc cccccaacac tcccgacgtg   3420
cgcgccgggg tcaccgctat cgcacagaca ccgaacgaaa cgtcgggaag gtagcaactg   3480
gtccatccat ccaggcgcgg ctgcgggcag aggaagcatc cggcgcgcag ctcgcccccg   3540
gaacggagcc ctcgccagcg ccgttgggcc aaccgagatc gtatctggct ccgcccaccc   3600
gccccgcgcc gacagaacct cccccagcc cctcgccgca gcgcaactcc ggtcggcgtg    3660
ccgagcgacg cgtccacccc gatttagccg cccaacatgc cgcggcgcaa cctgattcaa   3720
ttacggccgc aaccactggc ggtcgtcgcc gcaagcgtgc agcgccggat ctcgacgcga   3780
cacagaaatc cttaaggccg gcggccaagg ggccgaaggt gaagaaggtg aagccccaga   3840
aaccgaaggc cacgaagccg cccaaagtgg tgtcgcagcg cggctggcga cattgggtgc   3900
atgcgttgac gcgaatcaac ctgggcctgt caccgacga gaagtacgag ctggacctgc    3960
acgctcgagt ccgccgcaat ccccgcgggt cgtatcagat cgccgtcgtc ggtctcaaag   4020
gtggggctgg caaaaccacg ctgacagcag cgttggggtc gacgttggct caggtgcggg   4080
ccgaccggat cctggctcta gacgcggatc caggcgccgg aaacctcgcc gatcgggtag   4140
ggcgacaatc gggcgcgacc atcgctgatg tgcttgcaga aaaagagctg tcgcactaca   4200
acgacatccg cgcacacact agcgtcaatg cggtcaatct ggaagtgctg ccggcaccgg   4260
aatacagctc ggcgcagcgc gcgctcagcg acgccgactg gcatttcatc gccgatcctg   4320
cgtcgaggtt ttacaacctc gtcttggctg attgtggggc cggcttcttc gacccgctga   4380
cccgcggcgt gctgtccacg gtgtccggtg tcgtggtcgt ggcaagtgtc tcaatcgacg   4440
gcgcacaaca ggcgtcggtc gcgttggact ggttgcgcaa caacggttac caagatttgg   4500
cgagccgcgc atgcgtggtc atcaatcaca tcatgccggg agaacccaat gtcgcagtta   4560
aagacctggt gcggcatttc gaacagcaag ttcaacccgg ccgggtcgtg gtcatgccgt   4620
gggacaggca cattgcggcc ggaaccgaga tttcactcga cttgctcgac cctatctaca   4680
agcgcaaggt cctcgaattg gccgcagcgc tatccgacga tttcgagagg ctggacgtc    4740 gttgagcgca cctgctgttg ctgctggtcc taccgccgcg ggggcaaccg ctgcgcggcc   4800
tgccaccacc cgggtgacga tcctgaccgg cagacggatg accgatttgg tactgccagc   4860
ggcggtgccg atggaaactt atattgacga caccgtcgcg gtgctttccg aggtgttgga   4920
agacacgccg gctgatgtac tcggcggctt cgactttacc gcgcaaggcg tgtgggcgtt   4980
cgctcgtccc ggatcgccgc cgctgaagct cgaccagtca ctcgatgacg ccggggtggt   5040
cgacgggtca ctgctgactc tggtgtcagt cagtcgcacc gagcgctacc gaccgttggt   5100
cgaggatgtc atcgacgcga tcgccgtgct tgacgagtca cctgagttcg accgcacggc   5160
```

```
attgaatcgc tttgtggggg cggcgatccc gcttttgacc gcgcccgtca tcgggatggc    5220
gatgcgggcg tggtgggaaa ctgggcgtag cttgtggtgg ccgttggcga ttggcatcct    5280
ggggatcgct gtgctggtag gcagcttcgt cgcgaacagg ttctaccaga gcggccacct    5340
ggccgagtgc ctactggtca cgacgtatct gctgatcgca accgccgcag cgctggccgt    5400
gccgttgccg cgcggggtca actcgttggg ggcgccacaa gttgccggcg ccgctacggc    5460
cgtgctgttt ttgaccttga tgacgcgggg cggccctcgg aagcgtcatg agttggcgtc    5520
gtttgccgtg atcaccgcta tcgcggtcat cgcggccgcc gctgccttcg gctatggata    5580
ccaggactgg gtccccgcgg ggggatcgc attcgggctg ttcattgtga cgaatgcggc     5640
caagctgacc gtcgcggtcg cgcggatcgc gctgccgccg attccggtac ccggcgaaac    5700
cgtggacaac gaggagttgc tcgatcccgt cgcgaccccg gaggctacca gcgaagaaac    5760
cccgacctgg caggccatca tcgcgtcggt gcccgcgtcc gcggtccggc tcaccgagcg    5820
cagcaaactg gccaagcaac ttctgatcgg atacgtcacg tcgggcaccc tgattctggc    5880
tgccggtgcc atcgcggtcg tggtgcgcgg gcacttcttt gtacacagcc tggtggtcgc    5940
gggtttgatc acgaccgtct gcggatttcg ctcgcggctt tacgccgagc gctggtgtgc    6000
gtgggcgttg ctggcggcga cggtcgcgat tccgacgggt ctgacggcca aactcatcat    6060
ctggtacccg cactatgcct ggctgttgtt gagcgtctac ctcacggtag ccctggttgc    6120
gctcgtggtg gtcgggtcga tggctcacgt ccggcgcgtt tcaccggtcg taaaacgaac    6180
tctggaattg atcgacggcg ccatgatcgc tgccatcatt cccatgctgc tgtggatcac    6240
cggggtgtac gacacggtcc gcaatatccg gttctgagcc ggatcggctg attggcggtt    6300
cctgacagaa catcgaggac acggcgcagg tttgcatacc ttcggcgccc gacaaattgc    6360
tgcgattgag cgtgtggcgc gtccggtaaa atttgctcga tggggaacac gtataggaga    6420
tccggcaatg gctgaaccgt tggccgtcga tcccaccggc ttgagcgcag cggccgcgaa    6480
attggccggc ctcgttttc cgcagcctcc ggcgccgatc gcggtcagcg gaacggattc    6540
ggtggtagca gcaatcaacg agaccatgcc aagcatcgaa tcgctggtca gtgacgggct    6600
gcccggcgtg aaagccgccc tgactcgaac agcatccaac atgaacgcgg cggcggacgt    6660
ctatgcgaag accgatcagt cactgggaac cagtttgagc cagtatgcat tcggctcgtc    6720
gggcgaaggc ctggctggcg tcgcctcggt cggtggtcag ccaagtcagg ctacccagct    6780
gctgagcaca cccgtgtcac aggtcacgac ccagctcggc gagacggccg ctgagctggc    6840
accccgtgtt gttgcgacgg tgccgcaact cgttcagctg gctccgcacg ccgttcagat    6900
gtcgcaaaac gcatccccca tcgctcagac gatcagtcaa accgcccaac aggccgccca    6960
gagcgcgcag ggcggcagcg gcccaatgcc cgcacagctt gccagcgctg aaaaaccggc    7020
caccgagcaa gcggagccgg tccacgaagt gacaaacgac gatcagggcg accagggcga    7080
cgtgcagccg gccgaggtcg ttgccgcggc acgtgacgaa ggcgccggcg catcaccggg    7140
ccagcagccc ggcgggggcg ttcccgcgca agccatggat accggagccg gtgcccgccc    7200
agcggcgagt ccgctggcgg ccccgtcga tccgtcgact ccggcaccct caacaaccac     7260
aacgttgtag accgggcctg ccagcggctc cgtctcgcac gcagcgcctg ttgctgtcct    7320
ggcctcgtca gcatgcggcg gccagggccc ggtcgagcaa cccggtgacg tattgccagt    7380
acagccagtc cgcgacggcc acacgctgga cggccgcgtc agtcgcagtg tgcgcttggt    7440
gcagggcaat ctcctgtgag tgggcagcgt aggcccggaa cgcccgcaga tgagcggcct    7500
```

```
cgcggccggt agcggtgctg gtcatgggct tcatcagctc gaaccacagc atgtgccgct   7560
catcgcccgg tggattgaca tccaccggcg ccggcggcaa caagtcgagc aaacgctgat   7620
cggtagtgtc ggccagctga gccgccgccg aggggtcgac gacctccagc cgcgaccggc   7680
ccgtcatttt gccgctctcc ggaatgtcat ctggctccag cacaatcttg gccacaccgg   7740
gatccgaact ggccaactgc tccgcggtac cgatcaccgc ccgcagcgtc atgtcgtgga   7800
aagccgccca ggcttgcacg gccaaaaccg ggtaggtggc acagcgtgca atttcgtcaa   7860
ccgggattgc gtgatccgcg ctggccaagt acaccttatt cggcaattcc atcccgtcgg   7920
gtatgtaggc cagcccatag ctgttggcca cgacgatgga accgtcggtg gtcaccgcgg   7980
tgatccagaa gaacccgtag tcgcccgcgt tgttgtcgga cgcgttgagc gccgccgcga   8040
tgcgtcgcgc caaccgcagc gcatcaccgc ggccacgctg gcgggcgctg gcagctgcag   8100
tggcggcgtc gcgtgccgcc cgagccgccg acaccgggat catcgacacc ggcgtaccgt   8160
catctgcaga ctcgctgcga tcgggtttgt cgatgtgatc ggtcgacggc gggcgggcag   8220
gaggtgccgt ccgcgccgag gccgcccgcg tgctcggtgc cgccgccttg tccgaggtag   8280
ccaccggcgc ccgcccagtg gcagcatgcg accccgcgcc cgaggccgcg gccgtaccca   8340
cgctcgaacg cgcgcccgct cccacggcgg taccgctcgg cgcggcggcc gccgccgtg   8400
cgcccgggac accggacgcc gcagccggcg tcaccgacgc ggcggattcg tccgcatggg   8460
caggccccga ctgcgtcccc ccgcccgcat gctggcccgg cacaccaggt tgctccgcca   8520
acgccgcggg tttgacgtgc ggcgccggct cgcccctgg ggtgcccggt gttgctggac   8580
cagacggacc gggagtggcc ggtgtaaccg gctggggccc aggcgatggc gccggtgccg   8640
gagccggctg cgggtgtgga gcgggagctg gggtaacggg cgtggccggg gttgccggtg   8700
tggccggggc gaccgggggg gtgaccggcg tgatcggggt tggctcgcct ggtgtgcccg   8760
gtttgaccgg ggtcaccggg gtgaccggct gccccgggt caccggcgtg acggagtgc   8820
cgggcgttgg tgtgatcgga gttaccggcg ctcccgggat gggtgtgatt ggggttcccg   8880
gggtgatcgg ggttcccggg gtgatcgggg ttcccggtgt gccggtgtg cccggggatg   8940
gcacgaccag ggtaggcacg tctggggtg gcggcgactt ctgctgaagc aaatcctcga   9000
gtgcgttctt cggaggtttc caattcttgg attccagcac ccgctcagcg gtctcggcga   9060
ccagactgac attggcccca tgcgtcgccg tgaccaatga attgatggcg gtatggcgct   9120
catcagcatc caggctaggg tcattctcca ggatatcgat ctcccgttga gcgccatcca   9180
cattattgcc gatatcggat ttagcttgct caatcaaccc ggcaatatgc ctgtgccagg   9240
taatcaccgt ggcagataa tcctgcagcg tcatcaattg attgatgttt gcacccaggg   9300
cgccgttggc agcattggcg gcgccgccgg accataggcc gccttcgaag acgtggcctt   9360
tctgctggcg gcaggtgtcc aatacatcgg tgaccctttg caaaacctgg ctatattcct   9420
gggcccggtc atagaaagtg tcttcatcgg cttc                               9454
```

<210> SEQ ID NO 2
<211> LENGTH: 1298
<212> TYPE: DNA
<213> ORGANISM: Mycobacterium tuberculosis

<400> SEQUENCE: 2

```
ggtctagcag ctcgcccgcg ttttcgggca caaatgccgg atcgtggccc atgtcgatcg     60
gtttgttgta agcgtcgaca aacacgatcc gcggctggta tgtgcgggcc cgggcgtcgt    120
ccatcgtcgc gtacgcaatc agaatcacca gatccccgg atgcaccaag tgcgcggcgg    180
```

-continued

```
caccgttgat gccaatcaca ccactgccgc gttcgccggt gatcgcgtag gtgaccagtc      240
gagcaccgtt gtcgatatcg acgatggtta cctgttcgcc ttccagcagg tcggcggcgt      300
ccatcaagtc ggcatcgatg gtcaccgagc cgacgtagtg caggtcggcg caggtcaccg      360
tggcgcggtg gatcttcgac ttcagcatcg tccgtaacat cagtttctcc aatgtgattc      420
gaggattgcc cggtatccgt ccgggcggtc ggtgccggcg aaagttccga tttcaatcgc      480
aatgttgtcc agcagcctgg tggtgccaag ccgggcagca accagcagcc gaccggaacc      540
gttgagcggc atcgggccaa gcccgatatc gcgcagctcc aggtagtcga ccgccacgcc      600
gggtgcagcg tcgagcaccg cacgggcggc atccagcgcg gcctgcgcgc cagccgttgc      660
cgcatgcgct gcggccgtta gcgccgccga gagcgcgacg gccgccgcac gctgggccgg      720
gtccaggtag cggttgcgcg acgacatcgc cagcccgtcg gcttcgcgca cggtcggcac      780
gccgaccacc gcgacatcga ggttgaagtc cgcgaccagc tgccggatca gcaccagctg      840
ctggtagtcc ttctcaccga agaacacccg atccgggcgc acgatctgca gcagctttag      900
cacgaccgtc agcacgccgg cgaaatgggt tggccgcggg ccgccctcga gttcggcggc      960
caacggaccg ggttgcacgg tggtgcgcag gccgtcggga tacatcgccg cggtagttgg     1020
cgtgaaagcg atttccacgc cttcggcccg cagttgcgcc aggtcgtcgt ccggggtgcg     1080
gggataggcg tcgagatctt ccccggcacc gaattgcatc gggttgacga agatcgacac     1140
gacgacgacc gatccgggca cccgcttggc cgcacgcacc aacgcgaggt ggccttcgtg     1200
cagcgcaccc atagtaggca ccaacatcac tcgccggccg gtgagtcgca gtgcgcgact     1260
gacatcggcg acatcccccg gtgccgagta cacattga                             1298

<210> SEQ ID NO 3
<211> LENGTH: 771
<212> TYPE: DNA
<213> ORGANISM: Mycobacterium tuberculosis

<400> SEQUENCE: 3
aacgggcgat gagccgggac gcgtcgatgt accgcgccgc cgccgggctg caccggctgt       60
gcgacagcct atccggagca caggttcgcg acgtggcttg tcgccgcgat ttcgaggacg      120
tggcgctcac gctggtcgcg cagagcgtga ccgccgccgc cttggcccgc accgaaagcc      180
gtggctgcca tcatcgcgcg gagtacccgt gcaccgtgcc ggagcaggca cgcagcatcg      240
tggtccgggg agccgacgac gcaaatgcgg tgtgtgtcca ggcgctagtg gcggtgtgct      300
gatggggtta tccgactggg agctggctgc ggctcgagca gcaatcgcgc gtgggctcga      360
cgaggacctc cggtacggcc cggatgtcac cacattggcg acggtgcctg ccagtgcgac      420
gaccaccgca tcgctggtga cccgggaggc cggtgtggtt gccggattgg atgtcgcgct      480
gctgacgctg aacgaagtcc tgggcaccaa cggttatcgg gtgctcgacc gcgtcgagga      540
cggcgcccgg gtgccgccgg agaggcact  tatgacgctg gaagcccaaa cgcgcggatt      600
gttgaccgcc gagcgcacca tgttgaacct ggtcggtcac ctgtcgggaa tcgccaccgc      660
gacggccgcg tgggtcgatg ctgtgcgcgg gaccaaagcg aaaatccgcg ataccegtaa      720 gacgctgccc ggcctgcgcg cgctgcaaaa atacgcggtg cgtaccggtg g              771

<210> SEQ ID NO 4
<211> LENGTH: 1255
<212> TYPE: DNA
<213> ORGANISM: Mycobacterium tuberculosis
```

<400> SEQUENCE: 4

```
gtgaacgagc tgctgcactt agcgccgaat gtgtggccgc gcaatactac tcgcgatgaa    60
gtcggtgtgg tctgcatcgc aggaattcca ctgacgcagc tcgcccagga gtacgggacc   120
ccgctgttcg tcatcgacga ggacgacttt cgctcgcgct gccgagaaac cgccgcggcc   180
tttggaagtg gggcgaacgt gcactatgcc gccaaggcgt tcctgtgcag cgaagtagcc   240
cggtggatca gcgaagaagg gctctgtctg gacgtttgca ccggtgggga gttggcggtc   300
gcgctgcacg ctagctttcc gcccgagcga attaccttgc acggcaacaa caaatcggtc   360
tcagagttga ccgctgcggt caaagccgga gtcggccata ttgtcgtcga ttcgatgacc   420
gagatcgagc gcctcgacgc catcgcgggc gaggccggaa tcgtccagga tgtcctggtg   480
cgtctcaccg tcggtgtcga ggcgcacacc cacgagttca tctccaccgc gcacgagacg   540
cgtcagccac atcggttcgc agatcttcga cgtggacggc ttcgaactcg ccgcgcaccg   600
tgtcatcggc ctgctacgcg acgtcgtcgg cgagttcggt cccgaaaaga cggcacagat   660
cgcgaccgtc gatctcggtg gcggcttggg catctcgtat ttgccgtccg acgacccacc   720
gccgatagcc gagctcgcgg ccaagctggg taccatcgtg agcgacgagt caacggccgt   780
ggggctgccg acgcccaagc tcgttgtgga gcccggacgc gccatcgccg gaccgggcac   840
catcacgttg tatgaggtcg gcaccgttaa ggacgtcgat gtcagcgcca cagcgcatcg   900
acgttacgtc agtgtcgacg gcggcatgag cgacaacatc cgcaccgcgc tctacggcgc   960
gcagtatgac gtccggctgg tgtctcgagt cagcgacgcc ccgccggtac cggcccgtct  1020
ggtcggaaag cactgcgaaa gtggcgatat catcgtgcgg gacacctggg tgcccgacga  1080
tattcggccc ggcgatctgg ttgcggttgc cgccaccggc gcttactgct attcgctgtc  1140
gagtcgttac aacatggtcg gccgtcccgc tgtggtagcg gtgcacgcgg gcaacgctcg  1200
cctggtcctg cgtcgggaga cggtcgacga tttgctgagt ttggaagtga ggtga       1255
```

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5

```
gggggcgcac ctcaaacc                                                   18
```

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6

```
atgtgccaat cgtcgaccag aa                                              22
```

<210> SEQ ID NO 7
<211> LENGTH: 17
<212> TYPE: DNA
<213> ORGANISM: Artificial
<220> FEATURE:
<223> OTHER INFORMATION: primer

<400> SEQUENCE: 7

```
cacccagccg cccggat                                                    17
```

```
<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
ttcctgatgc cgccgtctga                                               20

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
gtgcagcgcc atctctca                                                 18

<210> SEQ ID NO 10
<211> LENGTH: 18
<212> TYPE: DNA
<213> ORGANISM: Artificial
<220> FEATURE:
<223> OTHER INFORMATION: primer

<400> SEQUENCE: 10
gttcaccggg atggaacg                                                 18

<210> SEQ ID NO 11
<211> LENGTH: 18
<212> TYPE: DNA
<213> ORGANISM: Artificial
<220> FEATURE:
<223> OTHER INFORMATION: primer

<400> SEQUENCE: 11
cccggctcgg tgtgggat                                                 18

<210> SEQ ID NO 12
<211> LENGTH: 18
<212> TYPE: DNA
<213> ORGANISM: Artificial
<220> FEATURE:
<223> OTHER INFORMATION: primer

<400> SEQUENCE: 12
gcgcggtatg cccggtag                                                 18
```

ATTENUATED MYCOBACTERIUM TUBERCULOSIS VACCINES

CROSS-REFERENCE TO RELATED APPLICATION

This is a continuation-in-part application of application Ser. No. 10/351,452, filed Jan. 24, 2003, which claims the benefit of U.S. Provisional Application No. 60/358,152, filed Feb. 19, 2002. Those applications are incorporated by reference herewith in their entirety.

STATEMENT REGARDING FEDERALLY SPONSORED RESEARCH OR DEVELOPMENT

The present invention was supported by NIH Grant No. AI26170. As such, the U.S. Government has certain rights in the invention.

BACKGROUND OF THE INVENTION (1) Field of the Invention

The present invention generally relates to live bacterial vaccines. More specifically, the invention is related to novel *Mycobacterium* sp. compositions, and the use of those compositions to protect mammals against disease caused by virulent *Mycobacterium* sp.

(2) Description of the Related Art

References Cited

Abiko, Y. in *Metabolic Pathways*. D. M. Greenburg, Ed. (Academic Press, New York, 1975).

Afshar, K., Gonczy, P., DiNardo, S. & Wasserman, S. A. fumble encodes a pantothenate kinase homolog required for proper mitosis and meiosis in *Drosophila melanogaster*. Genetics 157, 1267-76. (2001).

Andersen, P. Host responses and antigens involved in protective immunity to *Mycobacterium tuberculosis*. Scand. J. Immunol. 45, 115-31 (1997).

Andersen, P., Askgaard, D., Ljungqvist, L., Bennedsen, J. & I. Heron. Proteins released from *Mycobacterium tuberculosis* during growth. Infect. Immun. 59, 1905-10 (1991).

Armbruster, C., W. Junker, N. Vetter, and G. Jaksch. Disseminated bacille Calmette-Guerin infection in an A IDS patient 30 years after BCG vaccination. J Infect Dis 162, 1216 (1990).

Baily, G. V. Tuberculosis prevention Trial, Madras. Indian J Med Res 72 Suppl, 1-74 (1980).

Balasubramanian, V., et al. Allelic exchange in *Mycobacterium tuberculosis* with long linear recombination substrates. J. Bacteriol. 178, 273-9 (1996).

Baldwin, S. L. et al. Evaluation of new vaccines in the mouse and guinea pig model of tuberculosis. Infect. Immun. 66, 2951-2959 (1998).

Bardarov, S. et al. Conditionally replicating mycobacteriophages: a system for transposon delivery to *Mycobacterium tuberculosis*. Proc. Natl. Acad. Sci. USA 94, 10961-6. (1997).

Bardarov, S. et al. Microbiology 148, 3007-17 (2002).

Behar, S. M., et al. Susceptibility of mice deficient in CD1D or TAP1 to infection with *Mycobacterium tuberculosis*. J. Exp. Med. 189, 1973-80 (1999).

Behr, M. A., and P. M. Small. Has BCG attenuated to impotence? Nature 389, 133-4 (1997).

Behr, M. A. et al. Comparative genomics of BCG vaccines by whole-genome DNA microarray [see comments]. Science 284, 1520-3 (1999).

Bermudez, L. E., Sangari, F. J., Kolonoski, P., Petrofsky, M. and J. Goodman. Infect. Immun. 71, 140-146 (2002)

Berthet, F. X., Rasmussen, P. B., Rosenkrands, I., Andersen, P. & B. A. Gicquel. *Mycobacterium tuberculosis* operon encoding E SAT-6 and a novel low-molecular-mass culture filtrate protein (CFP-10). Microbiology 144, 3195-203. (1998).

Besnard, M., S. Sauvion, C. Offredo, J. Gaudelus, J. L. Gaillard, F. Veber, and S. Blanche. *Bacillus* Calmette-Guerin infection after vaccination of human immunodeficiency virus-infected children. Pediatr Infect Dis J 12, 993-7 (1993).

Bloom, B. R. & P. Fine, pp. in 531-557 In Tuberculosis pathogenesis, protection, and control (ed. Bloom, B. R.) (American Society for Microbiology, Washington, D. C., 1994).

Brandt, L., M. Elhay, I. Rosenkrands, E. B. Lindblad, and P. Andersen. ESAT-6 subunit vaccination against *Mycobacterium tuberculosis*. Infect Immun 68, 791-5 (2000).

Brandt, L., J. Feino Cunha, A. Weinreich Olsen, B. Chilima, P. Hirsch, R. Appelberg, and P. Andersen. Failure of the *Mycobacterium bovis* BCG vaccine: some species of environmental mycobacteria block multiplication of BCG and induction of protective immunity to tuberculosis. Infect Immun 70, 672-8 (2002).

Calmette, A. & C. Guerin. Origine intestinale de la tuberculose pulmonaire. Ann. Inst. Pasteur 19, 601-618 (1905).

Calmette, A. & C. Guerin. C. R. Acad. Sci. 149; 716 (1909).

Calmette, A. & C. Guerin. Ann. Inst. Pasteur 34, 553 (1920).

Calmette, A. & H. Plotz. Protective inoculation against tuberculosis with BCG. Am. Rev. Tuberc. 19, 567-572 (1929).

Camacho, L. R., Ensergueix, D., Perez, E., Gicquel, B. & Guilhot, C. Identification of a virulence gene cluster of *Mycobacterium tuberculosis* by signature-tagged transposon mutagenesis. Mol Microbiol 34, 257-67. (1999).

Canaday, D. H. et al. Activation of human CD8+ alpha beta TCR+ cells by *Mycobacterium tuberculosis* via an alternate class I M HC antigen-processing pathway. J. Immunol. 162, 372-9 (1999).

Carriere, C. et al. Conditionally replicating luciferase reporter phages: improved sensitivity for rapid detection and assessment of drug susceptibility of *Mycobacterium tuberculosis*. J. Clin. Microbiol. 35, 3232-9. (1997).

Chambers, M. A. et al. Identification of a *Mycobacterium bovis* BCG auxotrophic mutant that protects guinea pigs against *M. bovis* and hematogenous spread of *Mycobacterium tuberculosis* without sensitization to tuberculin. Infect. Immun. 68, 7094-9 (2000).

Cho, S. et al. Antimicrobial activity of MHC class I-restricted CD8+ T cells in human tuberculosis. Proc. Natl. Acad. Sci. USA 97, 12210-5 (2000).

Cirillo, J. D. et al. A novel transposon trap for mycobacteria: isolation and characterization of IS1096. J. Bacteriol. 173, 7772-80 (1991).

Colditz G. A. et al. Pediatrics 96, 29-35. (1995).

Cole, S. T. et al. Deciphering the biology of *Mycobacterium tuberculosis* from the complete genome sequence [see comments] [published erratum appears in Nature 1998 Nov. 12; 396(6707):190]. Nature 393, 537-44 (1998).

Collins, F. M. Protection to mice afforded by BCG vaccines against an aerogenic challenge by three mycobacteria of decreasing virulence. Tubercle 66, 267-76. (1985).

Collins, F. M. Antituberculous immunity: new solutions to an old problem. Rev Infect Dis. 13, 940-50 (1991).

Cox, J. S., Chen, B., McNeil, M. & W. R. Jacobs, Jr. Complex lipid determines tissue-specific replication of *Mycobacterium tuberculosis* in mice. Nature 402, 79-83 (1999).

D'Souza, C. D. et al. An anti-inflammatory role for gamma delta T lymphocytes in acquired immunity to *Mycobacterium tuberculosis*. J. Immunol. 158, 1217-21 (1997).

D'Souza, C. D. et al. A novel nonclassic beta2-microglobulin-restricted mechanism influencing early lymphocyte accumulation and subsequent resistance to tuberculosis in the lung. Am. J. Respir. Cell. Mol. Biol. 23, 188-93 (2000).

Dascher, C. C., K. Hiromatsu, X. Xiong, C. Morehouse, G. Watts, G. Liu, D. N. McMurray, K. P. LeClair, S. A. Porcelli, and M. B. Brenner. Immunization with a Mycobacterial Lipid Vaccine Improves Pulmonary Pathology in the Guinea Pig Model of Tuberculosis. International Immunology 15, 915-925 (2003).

De Voss, J. J. et al. The salicylate-derived mycobactin siderophores of *Mycobacterium tuberculosis* are essential for growth in macrophages. Proc Natl Acad Sci USA 97, 1252-7. (2000).

Delogu, G. et al. Infect. Immun. 70, 293-302 (2002).

Dobos, K., Spotts, E., Quinn, F., & C. King. Infect. Immun. 68, 6300-6310 (2000).

Dolin, P. J., Raviglione, M. C. & A. Kochi. Global tuberculosis incidence and mortality during 1990-2000. Bull. World Health Organ. 72, 213-220 (1994).

Dubos, R. & W. Schaefer. Am. Rev. Tuberculous Pulm. Dis. 74, 541-551 (1956).

Dye, C., Scheele, S., Dolin, P., Pathania, V. & M. C. Raviglione. Consensus statement. Global burden of tuberculosis: estimated incidence, prevalence, and mortality by country. WHO Global Surveillance and Monitoring Project. JAMA 282, 677-686 (1999).

Elgert, K. D. Immunology, Wiley Liss, Inc., (1996).

Feng, C. G. et al. Increase in gamma interferon-secreting CD8(+), as well as CD4(+), T cells in lungs following aerosol infection with *Mycobacterium tuberculosis*. Infect. Immun. 67, 3242-7 (1999).

Fine, P. E. Lancet 346, 1339-45. (1995).

Fine, P. M. & Rodrigues, L. C. Modern vaccines: mycobacterial disease. Lancet 335, 1016-1020 (1990).

Finlay, B. B. & S. Falkow. Microbiol. Mol. Biol. Rev. 61, 136-69. (1997).

Fritz, C., Maass, S., Kreft, A. & F. C. Bange. Infect. Immun 70, 286-91. (2002).

Gennaro, Ed. Remington's Pharmaceutical Sciences, 17th Edition, (Mack Publishing Co., Easton, Pa., 1985).

Gheorghiu, M. in Vaccinia, Vaccination, and Vaccinology: Jenner, Pasteur and their successors (eds. Plotkin, S. A. & Fantini, B.) 87-94 (Elsevier, Paris, 1996).

Glickman, M. S., Cox, J. S. & W. R. Jacobs, Jr. A novel mycolic acid cyclopropane synthetase is required for coding, persistence, and virulence of *Mycobacterium tuberculosis*. Mol. Cell 5, 717-27 (2000).

Glickman, M. S., Cahill, S. M. & W. R. Jacobs, Jr. The *Mycobacterium tuberculosis* cmaA2 gene encodes a mycolic acid trans-cyclopropane synthetase. J. Biol. Chem. 276, 2228-33. (2001).

Gordon, S. V. et al. Genomics of *Mycobacterium bovis*. Tuberculosis 81, 157-63 (2001).

Grange, J. M., Gibson, J., Osborn, T. W., Collins, C. H. & M. D. Yates. What is BCG? Tubercle 64, 129-39. (1983).

Guleria, I. et al. Auxotrophic vaccines for tuberculosis. Nat. Med. 2, 334-7 (1996).

Harboe, M., T. Oettinger, H. G. Wiker, I. Rosenkrands, and P. Andersen. Evidence for occurrence of the ESAT-6 protein in *Mycobacterium tuberculosis* and virulent Mycobacterium bovis and for its absence in *Mycobacterium bovis* BCG. Infect Immun 64, 16-22 (1996).

Hart, P. D. & I. Sutherland. BCG and vole *bacillus* vaccines in the prevention of tuberculosis in adolescence and early life. Br. Med. J. 22, 2293-2295 (1977).

Hepper, K. P. & F. M. Collins. Immune responsiveness in mice heavily infected with *M. kansasii*. Immunol. 53, 357-364 (1984).

Hernandez-Pando, R., L. Pavon, K. Arriaga, H. Orozco, V. Madrid-Marina, and G. Rook. Pathogenesis of tuberculosis in mice exposed to low and high doses of an environmental mycobacterial saprophyte before infection. Infect Immun 65, 3317-27 (1997).

Hernandez-Pando, R., Schon, T., Orozco, R., Serafin, J. & I. Estrada-Garcia. Exp. Tox. Path. 53, 257-265 (2001).

Homchampa, P., Strugnell, R. A. and B. Adler. Molecular analysis of the aroA gene of *Pasteurella multocida* and vaccine potential of a constructed aroA mutant. Mol Microbiol. 6, 3585-93 (1992).

Hondalus, M. K. et al. Attenuation of and protection induced by a leucine auxotroph of *Mycobacterium tuberculosis*. Infect. Immun. 68, 2888-98 (2000).

Honer zu Bentrup, K. & D. G. Russell. Trends Microbiol. 9, 597-605. (2001).

Houde, C., and P. Dery. *Mycobacterium bovis* sepsis in an infant with human immunodeficiency virus infection. Pediatr Infect Dis J 7, 810-2 (1988).

Hubbard, R. D., Flory, C. M., Cocito, C. & F. M. Collins. Immunization of mice with antigen A60 of *Mycobacterium bovis* BCG. Clin. Exp. Immunol. 88, 129-131 (1992).

Hutter, B. & T. Dick. FEMS Microbiol. Lett 178, 63-9. (1999).

Jackowski, S. & J. H. Alix. J. Bacteriol. 172, 3842-8. (1990).

Jackowski, S. in *Escherichia coli and Salmonella typhimurium: Cellular and Molecular Biology*. F. C. Neidhardt, R. Curtiss, et al., Eds. (American Society for Microbiology, Washington, D. C., ed. Second, 1996).

Jackson, M. et al. Infect, Immun. 67, 2867-73. (1999).

Jacobs, W. R., Jr., Tuckman, M. & B. R. Bloom. Introduction of foreign DNA into mycobacteria using a shuttle phasmid. Nature 327, 532-5. (1987).

Jones, B. E. et al. Relationship of the manifestations of tuberculosis to CD4 cell counts in patients with human immunodeficiency virus infection. Am. Rev. Respir. Dis. 148, 1292-7 (1993).

Kalpana, G. V., Bloom, B. R. & W. R. Jacobs, Jr. Insertional mutagenesis and illegitimate recombination in mycobacteria. Proc. Natl. Acad. Sci. USA 88, 5433-7 (1991).

Kanai, K. & K. Yanagisawa. Jpn. J. Med. Sci. Biol. 8, 115-127 (1955).

Kaufmann, S. H., Ladel, C. H. & I. E. Flesch. T cells and cytokines in intracellular bacterial infections: experiences with *Mycobacterium bovis* BCG. Ciba Found. Symp. 195, 123-32 (1995).

Kaushal, D. et al. Reduced immunopathology and mortality despite tissue persistence in a *Mycobacterium tuberculosis* mutant lacking alternative sigma factor, SigH. Proc. Natl. Acad. Sci. USA 99, 8330-5. (2002).

Kirby, J. E., Vogel, J. P., Andrews, H. L. & R. R. Isberg. Mol. Microbiol. 27, 323-336 (1998).

Koch, R. Die Aetiologie der Tuberculos. Ber. Klin. Wochenschr. 19, 221-253 (1882).

Koch, R. 1891. Fortsetzung uber ein Heilmittel gegen Tuberculose. Dtch. Med. Wochenschr. 17, 101-102.

Lalvani, A. et al. Human cytolytic and interferon gamma-secreting CD8+ T lymphocytes specific for *Mycobacterium tuberculosis*. Proc. Natl. Acad. Sci. USA 95, 270-5 (1998).

Lalvani, A. et al. J. Infect. Dis. 183, 469477 (2001).

Lashuel, H. A. et al. Nature 418, 291 (2002).

Lee, M. H., Pascopella, L., Jacobs, W. R., Jr. & G. F. Hatfull. Site-specific integration of mycobacteriophage L5: integration-proficient vectors for *Mycobacterium smegmatis, Mycobacterium tuberculosis*, and bacille Calmette-Guerin. Proc. Natl. Acad. Sci. USA 88, 3111-5. (1991).

Lewinsohn, D. M. et al. *Mycobacterium tuberculosis-reactive* CD8+ T lymphocytes: the relative contribution of classical versus nonclassical H LA restriction. J. Immunol. 165, 925-30 (2000).

Mahairas, G. G., Sabo, P. J., Hickey, M. J., Singh, D. C. & C. K. Stover. Molecular analysis of genetic differences between *Mycobacterium bovis* BCG and virulent *M. bovis*. J. Bacteriol 178, 1274-82 (1996).

Manca, C. et al. Virulence of a *Mycobacterium tuberculosis* clinical isolate in mice is determined by failure to induce Th1 type immunity and is associated with induction of IFN-alpha/beta. Proc. Natl. Acad. Sci. USA 98, 5752-7. (2001).

McAdam, R. A., et al. In vivo growth characteristics of leucine and methionine auxotrophic mutants of *Mycobacterium bovis* BCG generated by transposon mutagenesis. Infect. Immun. 63, 1004-12 (1995).

P. J. McGuire, P. J. et al. Appl. Env. Micro. 68, 4646-9 (2002).

McDonough, K. A. & Y. Kress. Infect. Immun. 63, 4802-4811 (1995).

McKenney, D. et al. Science 284, 1523-7. (1999).

McKinney, J. D. et al., Nature 406, 735-8. (2000).

McMurray, D. M. 1994. Guinea Pig Model of Tuberculosis, p. 135-147. In B. R. Bloom (ed.), Tuberculosis: Pathogenesis, Protection and Control. A SM Press, Washington, D. C.

Mogues, T., et al. The relative importance of T cell subsets in immunity and immunopathology of airborne *Mycobacterium tuberculosis* infection in mice. J. Exp. Med. 193, 271-80 (2001).

Mohagheghpour, N., et al. CTL response to *Mycobacterium tuberculosis*: identification of an immunogenic epitope in the 19-kDa lipoprotein. J. Immunol. 161, 2400-6 (1998).

Morita, C. T., R. A. Mariuzza & M. B. Brenner. Antigen recognition by human gamma delta T cells: pattern recognition by the adaptive immune system. Springer Semin. Immunopathol. 22, 191-217 (2000).

Moreira, A. L., L. Tsenova, M. H. Aman, L. G. Bekker, S. Freeman, B. Mangaliso, U. Schroder, J. Jagirdar, W. N. Rom, M. G. Tovey, V. H. Freedman, and G. Kaplan. Mycobacterial antigens exacerbate disease manifestations in *Mycobacterium tuberculosis-infected* mice. Infect Immun 70, 2100-7 (2002).

Mukadi, Y., et al. Spectrum of immunodeficiency in HIV-1-infected patients with pulmonary tuberculosis in Zaire. Lancet 342, 143-6 (1993).

Muller, I., et al. Impaired resistance to *Mycobacterium tuberculosis* infectin after selective in vivo depletion of L3T4+ and Lyt-2+T cells. Infect. Immun. 55, 2037-41 (1987).

Murray, C. J. & J. A. Salomon. Proc. Natl. Acad. Sci. USA 95, 13881-6. (1998).

Nassi, S. et al. Biochemistry 41, 1445-1450 (2002).

O'Brien, K. L., A. J. Ruff, M. A. Louis, J. Desormeaux, D. J. Joseph, M. McBrien, J. Coberly, R. Boulos, and N. A. Halsey. *Bacillus* Calmette-Guerin complications in children born to HIV-1-infected women with a review of the literature. Pediatrics 95, 414-8 (1995).

Opie, E. L. & J. Freund. An experimental study of protective inoculation with heat killed tubercule bacilli. J. Exp. Med. 66, 761-788 (1937).

Pallen, M. Trends in Microbiol. 10, 209-212 (2002).

Palmer, C. E., and M. W. Long. Effects of infection with atypical mycobacteria on BCG vaccination and tuberculosis. Am Rev Respir Dis 94, 553-68 (1966).

Parish, T. & N. G. Stoker. Use of a flexible cassette method to generate a double unmarked *Mycobacterium tuberculosis* tlyA plcABC mutant by gene replacement. Microbiol. 146, 1969-1975 (2000).

Pascopella, L. et al. Use of in vivo complementation in *Mycobacterium tuberculosis* to identify a genomic fragment associated with virulence. Infect. Immun. 62, 1313-9. (1994).

Pavelka, M. S., Jr. & W. R. Jacobs, Jr. Comparison of the construction of unmarked deletion mutations in *Mycobacterium smegmatis, Mycobacterium bovis bacillus* Calmette-Guerin, and *Mycobacterium tuberculosis* H37Rv by allelic exchange. J. Bacteriol. 181, 4780-9 (1999).

Pedrazzini, T., Hug, K. & J. A. Louis Importance of L3T4+ and Lyt-2+ cells in the immunologic control of infection with *Mycobacterium bovis* strain *bacillus* Calmette-Guerin in mice. Assessment by elimination of T cell subsets in vivo. J. Immunol. 139, 2032-7 (1987).

Pelicic, V., Reyrat, J. M. & B. Gicquel. Generation of unmarked directed mutations in mycobacteria, using sucrose counter-selectable suicide vectors. Mol. Microbiol. 20, 919-25. (1996).

Pelicic, V. et al. Efficient allelic exchange and transposon mutagenesis in *Mycobacterium tuberculosis*. Proc. Natl. Acad. Sci. USA 94, 10955-60 (1997).

Pethe, K. et al. Nature 412, 190-194 (2001).

Petroff, S. A., Branch, A. & W. Steenken, Jr. A study of *Bacillus* Calmette-Guerin. 1. Biological characteristics, cultural 'dissociation' and animal experimentation. Am. Rev. Tuberc. 9, 46 (1929).

Prasad, P. D. et al. J. Biol. Chem. 273, 7501-6. (1998).

Prasad, P. D. & V. Ganaphthy. Curr. Opin. Clin. Nutr. Metab. Care 3, 263-6. (2000).

Pym, A. S. et al. Mol. Microbio. 46, 709-717 (2002).

Pym, A. S., P. Brodin, L. Majlessi, R. Brosch, C. Demangel, A. Williams, K. E. Griffiths, G. Marchal, C. Leclerc, and S. T. Cole. Recombinant BCG exporting ESAT-6 confers enhanced protection against tuberculosis. Nat Med 9, 533-9 (2003).

Raman, S. et al. The alternative sigma factor SigH regulates major components of oxidative and heat stress responses in *Mycobacterium tuberculosis*. J. Bacteriol. 183, 6119-25. (2001).

Renshaw, P. et al. J. Biol. Chem. 277, 21598-21603 (2002).

Reynes, J., C. Perez, I. Lamaury, F. Janbon, and A. Bertrand. Bacille Calmette-Guerin adenitis 30 years after immunization in a patient with AIDS. J Infect Dis 160, 727 (1989).

Riley, R. L., C. C. Mills, W. Nyka, N. Weinstock, P. B. Storey, L. U. Sultan, M. C. Riley, and W. F. Wells. Aerial dissemination of pulmonary tuberculosis. A two year study of contagion in a tuberculosis ward. American Journal of Hygiene 70, 185-196 (1959).

Rodrigues, L. C., Gill, N. & Smith, P. G. BCG vaccination in the first year of life protects children of Indian subcontinent ethnic origin against tuberculosis in England. J. Epidemiol. 45, 78-80 (1991).

Rosat, J. P. et al. CD1-restricted microbial lipid antigen-specific recognition found in the CD8+ alpha beta T cell pool. J. Immunol. 162, 366-71 (1999).

Saliba, K. J. & K. Kirk. J. Biol. Chem. 276, 18115-21 (2001).

Sambandamurthy, V. K., X. Wang, B. Chen, R. G. Russell, S. Derrick, F. M. Collins, S. L. Morris, and W. R. Jacobs. A pantothenate auxotroph of Mycobacterium tuberculosis is highly attenuated and protects mice against tuberculosis. Nat Med 9, 9 (2002).

Sambandamurthy, V. K. et al. Nature Med. 10, 1171-4 (2002).

Sambandamurthy V K, Derrick S C, Jalapathy K V, Chen B, Russell R G, Morris S L, Jacobs W R Jr. Long-term protection against tuberculosis following vaccination with a severely attenuated double lysine and pantothenate auxotroph of Mycobacterium tuberculosis. Infect Immun. 73(2): 1196-203 (2005).

Sampson et al. Protection elicited by a double leucine and pantothenate auxotroph of Mycobacterium tuberculosis in guinea pigs. Infect. Immun. 72, 3031-7 (May 2004).

Scanga, C. A. et al. Depletion of CD4(+) T cells causes reactivation of murine persistent tuberculosis despite continued expression of interferon gamma and nitric oxide synthase 2. J. Exp. Med. 192, 347-58 (2000).

Serbina, N. V. and J. L. Flynn. CD8(+) T cells participate in the memory immune response to Mycobacterium tuberculosis. Infect. Immun. 69, 4320-8 (2000).

Shen, Y. et al. Antiretroviral agents restore Mycobacterium-specific T-cell immune responses and facilitate controlling a fatal tuberculosis-like disease in Macaques coinfected with simian immunodeficiency virus and Mycobacterium bovis BCG. J. Virol. 75, 8690-6 (2001).

Shen, Y., Zhou, D., Chalifoux, L., Simon, M., Shen, L., Li, P., Sehgal, P. K., Letvin, N. L. & Z. W. Chen. Induction of an simian immunodeficiency virus-related tuberculosis-like disease in macaques: An animal model for A IDS virus/mycobacterium coinfection. Infect. Immun. 70, 869-77 (2001).

Silva, C. L. & D. B. Lowrie. Identification and characterization of murine cytotoxic T cells that kill Mycobacterium tuberculosis. Infect. Immun. 68, 3269-74 (2000).

Skinner, M. A., A. J. Ramsay, G. S. Buchan, D. L. Keen, C. Ranasinghe, L. Slobbe, D. M. Collins, G. W. de Lisle, and B. M. Buddle. A D NA prime-live vaccine boost strategy in mice can augment IFN-gamma responses to mycobacterial antigens but does not increase the protective efficacy of two attenuated strains of Mycobacterium bovis against bovine tuberculosis. Immunology 108,548-55 (2003).

Skjot, R. et al., Infect. Immun. 68, 214-220 (2000).

Slyshenkov, V. S., Rakowska, M., Moiseenok., A. G. & L. Wojtczak. Free Radic. Biol. Med. 19, 767-72. (1995).

Slyshenkov, V. S., Moiseenok, A. G. & Wojtczak, L. Noxious effects of oxygen reactive species on energy-coupling processes in Ehrlich ascites tumor mitochondria and the protection by pantothenic acid. Free Radic Biol Med 20, 793-800 (1996).

Slyshenkov, V. S., Piwocka, K., Sikora, E. & L. Wojtczak. Free Radic. Biol. Med. 30, 1303-10. (2001).

Smith, T. Certain aspects of natural and acquired resistance to tuberculosis and their bearing on preventative measures. Journal of the American Medical Association 68:764-769 (1917).

Smith, D. A., Parish, T. Stoker, N. G. & G. J. Bancroft, Infect. Immun. 69, 1142-50. (2001).

Snapper, S. B. et al. Lysogeny and transformation in mycobacteria: stable expression of foreign genes. Proc. Natl. Acad. Sci. USA 85, 6987-91. (1988).

Sousa, A. O. et al. Relative contributions of distinct MHC class I-dependent cell populations in protection to tuberculosis infection in mice. Proc. Natl. Acad. Sci. USA 97, 4204-8 (2000).

Stenger, S. et al. Differential effects of cytolytic T cell subsets on intracellular infection. Science 276, 1684-7 (1997).

Stites et al. Basic & Clinical Immunology; 7th Ed., Appleton & Lange, (1991).

Steyn, A. J. et al. Mycobacterium tuberculosis WhiB3 interacts with RpoV to affect host survival but is dispensable for in vivo growth. Proc. Natl. Acad. Sci. USA 99, 3147-52. (2002).

Talbot, E. A., M. D. Perkins, S. F. Silva, and R. Frothingham. 1997. Disseminated bacille Calmette-Guerin disease after vaccination: case report and review. Clin Infect Dis 24:1139-46.

Taylor, J. L., O. C. Turner, R. J. Basaraba, J. T. Belisle, K. Huygen, and I. M. Orme. 2003. Pulmonary necrosis resulting from D NA vaccination against tuberculosis. Infect Immun 71:2192-8.

Teitelbaum, R. et al. Immun. 10, 641-50 (1999).

Theuer, C. P. et al. Human immunodeficiency virus infection in tuberculosis patients. J Infect Dis. 162, 8-12 (1990).

Tuberculosis Prevention Trial. Trial of BCG vaccines in South India for tuberculosis prevention. Indian J. Med. Res. 72, 1-74 (1980).

Turner, J., E. R. Rhoades, M. Keen, J. T. Belisle, A. A. Frank, and I. M. Orme. Effective preexposure tuberculosis vaccines fail to protect when they are given in an immunotherapeutic mode. Infect Immun 68:1706-9 (2000).

Vallari, D. S. & C. O. Rock. J. Bacteriol. 164, 136-42. (1985).

van Pinxteren, L. et al. Clin. Diagn. Lab. Immunol. 7, 155-160 (2000).

Weber, I., Fritz, C., Ruttkowski, S., Kreft, A. & F. C. Bange. Mol. Microbiol. 35, 1017-25. (2000).

Weill-Halle, B. & Turpin, R. Premiers essais de vaccination antituberculeuse de l'enfant par le bacille Calmette-Guerin (BCG). Bulletins et Memories de la Societe Medicale des Hopitaux de Paris 49, 1589 (1925).

Young, D. B. Tuberculosis, p. 279-289. In B. R. Bloom and P.-H. Lambert (ed.), The Vaccine Book. Academic Press, San Diego (2003).

U.S. Pat. No. 6,271,034.

U.S. Pat. No. 5,504,005.

There exists an urgent need for a novel tuberculosis (TB) vaccine as there are more than 8 million new cases of tuberculosis and more than 2 million deaths reported each year by the WHO (Dye et al., 1999). The discovery of the causative agent of TB, Mycobacterium tuberculosis, by Robert Koch in 1882 opened up the possibility for a novel vaccine (Koch, 1882). Since then, numerous attempts to develop attenuated vaccines against tuberculosis have failed, including tuberculin (a protein extract of killed tubercle bacilli) developed by Dr. Koch himself. This failure of tuberculin to protect led to a firm conviction that immunity could only be established by inducing a definite, albeit limited, tuberculosis process" Grange et al., 1983). Thus, numerous labs set out to follow the example of Dr. Louis Pasteur for viruses and enrich attenuated mutants of the tubercle bacillus following repeated passaging.

In order to test the hypothesis that a tubercle bacillus isolated from cattle (now known as M. bovis) could transmit pulmonary tuberculosis following oral administration, Drs. Calmette and Guerin developed a medium containing beef bile that enabled the preparation of fine homogenous bacillary suspensions (Calmette and Guerin, 1905). An *M. bovis* strain obtained from Dr. Norcard, was passaged every 21 days in this medium and after the 39$^{th}$ passage, the strain was found to be unable to kill experimental animal (Gheorghiu, 1996). "Between 1908 and 1921, the strain showed no reversion to virulence after 230 passages on bile potato medium" (Id.), which is consistent with the attenuating mutation being a deletion mutation. In the animal studies that followed, the strain ('BCG') was found to be attenuated but it also protected animals receiving a lethal challenge of virulent tubercle bacilli (Calmette and Guerin, 1920). BCG was first used as a vaccine against tuberculosis in 1921. From 1921 to 1927, BCG was shown to have protective efficacy against TB in a study on children (Weill-Halle and Turpin, 1925; Calmette and Plotz, 1929) and adopted by the League of Nations in 1928 for widespread use in the prevention of tuberculosis. By the 1950s after a series of clinical trials, the WHO was encouraging widespread use of BCG vaccine throughout the world (Fine and Rodrigues, 1990). Although an estimated 3 billion doses have been used to vaccinate the human population against tuberculosis, the mechanism that causes BCG s attenuation remains unknown.

Mahairas et al. (1996) first compared the genomic sequences of BCG and M bovis using subtractive hybridization and found that there were three major deletions (named RD1, RD2, and RD3) present in the genome of *M. bovis*, but missing in BCG. Behr et al. (1999) and others (Gordon et al., 2001) later identified 16 large deletions, including RD1 to RD3, present in the BCG genome but absent in *M. tuberculosis*. These authors concluded that 111 of these 16 deletions were unique to *M. bovis*, while the remaining 5 deletions were unique to BCG. They also found that one of these 5 deletions, designated RD1 (9454 bp), is present in all of the BCG substrains currently used as TB vaccines worldwide and concluded that the deletion of RD1 appeared to have occurred very early during the development of BCG, probably prior to 1921 (Behr et al., 1999).

The development of insertional mutagenesis systems for BCG and *M. tuberculosis* (Kalpana et al., 1991), transposon mutagenesis systems (Cirillo et al., 1991; McAdam et al., 1995; Bardarov et al., 1997) and allelic exchange systems (Balasubramanian et al., 1996; Pelicic et al., 1997) led to the isolation of the first auxotrophic (nutrient-requiring) mutants of these slow-growing mycobacteria. Auxotrophic mutants of BCG and *M. tuberculosis* have been shown to confer protection to *M. tuberculosis* challenges with variable efficacies (Guleria et al., 1996; Smith et al., 2001). However, a head-to-head comparison of BCG to a leucine auxotroph of BCG showed that a single immunization elicited no positive skin-test and imparted little immunity to challenges with *M. tuberculosis* or *M. bovis* (Chambers et al., 2000). In contrast, a methionine auxotroph of BCG that grows in vivo did confer significant protection to challenge to both *M. tuberculosis* and *M. bovis* (Id.). A single dose of a leucine auxotroph of *M tuberculosis* protected BALB/c mice as well as BCG in terms of survival post *M. tuberculosis* challenge yet was not as efficient as BCG at restricting the in vivo growth of the virulent bacilli (Hondalus et al., 2000). These results suggest that optimal immunity against *M. tuberculosis* requires some growth of the immunizing strain. Double mutants of *M. tuberculosis* have also been created (Parish and Stoker, 2000), but whether such mutants are improved over single attenuating mutants in protecting mammals against challenge with a virulent mycobacterium, particularly when the host is immunocompromised, has not been established.

It is also worth noting that in the study of Chambers et al. (2000), both BCG and the BCG mutants seemed to protect better against *M. bovis* challenge than *M. tuberculosis*. If we assume the reverse correlate is true, we could hypothesize that optimal immunity against *M tuberculosis* could be achieved with *M. tuberculosis*-derived mutant that grew in the mammalian host.

Based on the above, there remains a need for improved live mycobacterial vaccines having attenuated virulence, that confer protection from virulent mycobacteria, particularly *M. tuberculosis*. The instant invention satisfies that need.

SUMMARY OF THE INVENTION

The present invention is based on the discovery that deletion of the RD1 region or a region controlling the production of a vitamin or the amino acids leucine or lysine from the genome of virulent mycobacteria in the *M. tuberculosis* complex attenuates the virulence of the mycobacteria without eliminating the ability of the mycobacteria to colonize susceptible mammals. These attenuated mycobacteria are capable of protecting the mammals from challenge by a virulent *M. tuberculosis* complex mycobacteria. The attenuated mycobacteria are thus useful in methods and compositions for vaccination of humans, cows and other mammals from virulent *M. tuberculosis* complex mycobacteria.

Accordingly, in some embodiments, the present invention is directed to a non-naturally occurring *Mycobacterium tuberculosis*. The *M. tuberculosis* comprises a deletion of an RD1 region or a region controlling production of a vitamin or the amino acids leucine or lysine. The *M. tuberculosis* preferably exhibits attenuated virulence in a mammal when compared to the *M. tuberculosis* without the deletion.

In certain aspects of these embodiments, the *Mycobacterium tuberculosis* is produced by deletion of an RD1 region or a region controlling production of a vitamin or leucine or lysine. In these aspects, the *M. tuberculosis* also preferably exhibits attenuated virulence in a mammal when compared to the *M. tuberculosis* without the deletion.

In related embodiments, the present invention is also directed to mycobacteria in the *M. tuberculosis* complex that are genetically engineered to comprise a deletion of an RD1 region or a region controlling production of a vitamin or the amino acids leucine or lysine.

The present invention is also directed to mycobacteria in the *M. tuberculosis* complex that comprise a deletion of a region controlling production of a vitamin. These mycobacteria are preferably capable of sustaining an infection in an immunocompetent mouse for at least 20 weeks.

The inventors have also discovered that mycobacteria that are auxotrophic for lysine or leucine have attenuated virulence and can protect a mammal against challenge by a virulent mycobacterium. Accordingly, the invention is also directed to non-naturally occurring mycobacteria in the *M. tuberculosis* complex, wherein the mycobacteria comprise a deletion of a region controlling production of lysine, and wherein the mycobacteria are capable of sustaining an infection in an immunocompetent mouse for at least 20 weeks.

The inventors have additionally discovered that mycobacteria having two attenuating deletions are highly attenuated, even in immunocompromised mammals, and are surprisingly effective in protecting mammals against challenge by a virulent microorganism. Thus, the invention is additionally directed to mycobacteria in the *M. tuberculosis* complex that are genetically engineered to comprise two deletions. The two deletions are any deletions where a virulent mycobacterium in the *M. tuberculosis* complex having either deletion exhibits attenuated virulence.

In further embodiments, the invention is directed to tuberculosis vaccines comprising any of the above-described M. tuberculosis or mycobacteria in the M. tuberculosis complex, in a pharmaceutically acceptable excipient. These vaccines are capable of protecting mammals from challenge by virulent mycobacteria in the M. tuberculosis complex.

The invention is also directed to methods of protecting mammals from virulent M. tuberculosis or mycobacteria in the M. tuberculosis* complex. The methods comprise treating the mammal with any of the above vaccines.

In other embodiments, the invention is directed to methods of preparing tuberculosis vaccines. The methods comprise deleting an RD1 region or a region controlling production of a vitamin or lysine or leucine from an *M. tuberculosis* to produce any of the M tuberculosis described above. In these embodiments, the vaccine is capable of protecting the mammal from challenge by a virulent *M. tuberculosis.*

In related embodiments, the invention is directed to other methods of preparing a tuberculosis vaccine. These methods comprise genetically engineering a mycobacterium to delete an RD1 region or a region controlling production of a vitamin or lysine or leucine to produce any of the mycobacteria described above. In these embodiments, the vaccine is capable of protecting the mammal from challenge by virulent mycobacteria of the *M. tuberculosis* complex.

The invention is also directed to non-naturally occurring *Mycobacterium tuberculosis* auxotrophic for leucine and pantothenate. In these embodiments, the *M. tuberculosis* exhibits attenuated virulence in a mammal when compared to the *M. tuberculosis* without the leucine and pantothenate auxotrophy. Tuberculosis vaccines comprising these *M. tuberculosis* in a pharmaceutically acceptable excipient are also part of the present invention. These vaccines are capable of protecting a mammal from challenge by a virulent *M. tuberculosis*. The invention is also directed to methods of protecting a mammal from a virulent *M. tuberculosis*. The methods comprise treating the mammal with these vaccines.

In further embodiments, the invention is directed to mycobacteria in the *Mycobacterium tuberculosis* complex, genetically engineered to comprise a deletion causing leucine auxotrophy and a deletion causing pantothenate auxotrophy. Tuberculosis vaccines comprising these mycobacteria in a pharmaceutically acceptable excipient are also part of the present invention. These vaccines are capable of protecting a mammal from challenge by a virulent *M. tuberculosis*. The invention is also directed to methods of protecting a mammal from a virulent mycobacterium. The methods comprise treating the mammal with these vaccines.

BRIEF DESCRIPTION OF THE DRAWINGS

FIG. 1 shows maps and autoradiographs pertaining to the construction of ΔRD1 mutants of *M. tuberculosis*. Panel a, *M. tuberculosis* H37Rv published sequence between 4346 kb and 4364 kb, showing predicted NcoI sites. Arrows on the top represent the genes in the RD1 region. The RD1 region deleted from *M. bovis* BCG is represented by an open bar spanning from Rv3871 to Rv3879c. Upstream and downstream flanking sequences, UFS and DFS respectively, are indicated as closed bars underneath the grid line. Panel b, Southern hybridization of *M. tuberculosis* H37Rv ΔRD1 created using two-step sequential homologous recombination. Panel c, Southern hybridization of *M. tuberculosis* H37Rv and Erdman ΔRD1 strains created using specialized transduction.

FIG. 2 shows graphs summarizing experiments establishing that *M. tuberculosis* H37Rv ΔRD1 is attenuated in SCID mice. Panel a, Seven female SCID mice were infected intravenously with $2\times10^6$ CFU *M. tuberculosis* H37Rv, *M. tuberculosis* H37Rv ΔRD1, and *M. tuberculosis* H37Rv ΔRD1::2F9 per mouse. The number of surviving mice was recorded post infection. Panel b, Mice were infected with different doses of *M. tuberculosis* H37Rv, *M tuberculosis* H37Rv ΔRD1, and *M. bovis* BCG. For each strain, infection doses of $2\times10^6$ CFU, $2\times10^5$ CFU, $2\times10^4$ CFU, and $2\times10^3$ CFU per mouse, were administered via tail intravenous injection.

FIG. 3 is photographs, micrographs and autoradiographs showing that the *M. tuberculosis* H37Rv ΔRD1 mutant exhibits two distinct colonial morphotypes. Panel a, *M tuberculosis* H37Rv. Panel b, *M. tuberculosis* H37Rv ΔRD1. Panel c, *M. tuberculosis* H37Rv ΔRD1::2F9. Panel d, Southern analysis of *M. tuberculosis* H37Rv ΔRD1 NcoI-digested genomic DNA, isolated from three smooth and three rough colonies and probed with DFS. Panels e-g, Colonial morphotypes at higher magnification. e, Smooth morphotype at week 4. f, Rough morphotype at week 4. g, Rough morphotype at week 6.

FIG. 4 is graphs showing the growth kinetics of *M. tuberculosis* H37Rv ΔRD1 in BALB/c mice. Mice were infected with $2\times10^6$ CFU through tail injection. Time to death was noted and at day 1, week 4, 8, 14, and 22 post-infection, mice were sacrificed to determine the mycobacterial burden in the spleen, liver, and lung. The numbers represent the means of CFUs in organs derived from three animals. The error bars represent the standard errors of the means. Panel a, Time to death assay in BALB/c mice. Panel b, Spleen. Panel c, Liver. Panel d, Lung.

FIG. 5 is micrographs from pathological studies of infected BALB/c mice. Panels a c, Lungs from mice infected with $2\times10^6$ CFU of *M. tuberculosis* H37Rv examined at 4, 8 and 14 weeks post-infection. The mild to moderate pneumonia at 4 and 8 weeks (a and b) progressed to severe consolidating granulomatous pneumonia at 14 weeks post infection (c). Panels d f, Lungs from mice infected with $2\times10^6$CFU of *M. tuberculosis* H37Rv ΔRD1 examined at 4, 8 and 22 weeks post-infection showing moderate pneumonia at 8 weeks post-infection (e) and persistent bronchitis and multifocal pneumonitis at 22 weeks post-infection (f). Panels (g) (i), Mild lung lesions from mice infected with $2\times10^6$CFU of BCG at 4, 8 and 22 weeks post-infection. Mild focal granulomas scattered widely in the lung at each time point with predominately lymphocytic accumulations in foci at 22 weeks post-infection.

FIG. 6 shows graphs summarizing experiments establishing that pantothenate auxotrophy leads to attenuation of *M. tuberculosis* ΔpanCD mutant in SCID mice. Panel A, Survival of BALB/c SCID mice (n=12 per group) infected intravenously with 490 CFU of H37Rv (○) or 210 CFU of panCD complementing strain (panCD in single copy integrated into the chromosome)(●) or $3.4\times10^5$ CFU of ΔpanCD mutant (▲) or $3.3\times10^5$ CFU of BCG-P (□). Panel B, Bacterial numbers in the spleen (●) and lungs (▲) of SCID mice infected intravenously with 490 CFU of H37Rv or numbers in spleen (○) and lungs (Δ) of mice infected with $3.4\times10^5$ CFU of ΔpanCD mutant. The results represent means±standard errors of four to five mice per group.

FIG. 7 shows graphs summarizing experiments demonstrating the attenuation, limited growth and persistence of ΔpanCD mutant in immunocompetent mice. Panel A, Survival of BALB/c mice (n=12 per group) infected with $4.4\times10^6$ CFU of wild-type *M. tuberculosis* H37Rv (○), $3.2\times10^6$ CFU panCD complementing strain (panCD in single copy integrated into the chromosome)(●) or $2.4\times10^6$ CFU panCD mutant (▲). Panels B and C, Bacterial loads in spleen and lungs of BALB/c mice infected intravenously with 4.4×10⁶ CFU wild-type H37Rv (○) or 3.2×10⁶ CFU panCD complementing strain (●) or 2.4×10⁶ CFU ΔpanCD mutant (▲). CFUs were assayed at various time points on 7H11 agar with or without pantothenate supplementation where required. The results represent means±standard errors of four to five mice per group.

FIG. 8 shows graphs summarizing experiments demonstrating the attenuation, limited replication and persistence of ΔnadBC mutant in immunocompetent mice. Panels A and B, Bacterial loads in lungs and spleen of C57BL/6 mice infected with wild type $M.$ $tuberculosis$ H37Rv (●) or ΔnadBC mutant (○). Mice were infected intravenously with 10⁶ CFU of each strain. CFUs were assayed at various time points on 7H11 agar with or without nicotinamide supplementation where required. The results represent means±standard errors of four to five mice per group. Panel C, Survival of C57BL/6 mice (n=12 per group) infected with 10⁶ CFU of wild-type bacteria (●) or 10⁶ CFU of ΔnadBC mutant (○).

FIG. 9 shows an illustration, map and autoradiograph relating to the pathway for the biosynthesis of pantothenic acid and coenzyme A and its disruption in $M.$ $tuberculosis$. Panel a. The enzymes involved in the biosynthesis of pantothenic acid and having annotation in the genomic sequence of $M.$ $tuberculosis$ H37Rv are shown in bold numbers: 1) panB, ketopantoate hydroxymethyl transferase; 2) panD, aspartate-1-decarboxylase; 3) panC, pantothenate synthetase; 4) panK, pantothenate kinase; 5) acpS, ACP synthase. Panel b. Map of the panCD genomic region in the wild type $M.$ $tuberculosis$ H37Rv and the ΔpanCD mutant. Restriction sites and probe location are indicated. Panel c. Southern blot of BssHII-digested genomic DNA from wild-type H37Rv (lane 1), two independent clones of ΔpanCD mutant from H37Rv (lanes 2 & 3) and probed with a 716 bp downstream region flanking the panCD operon. Molecular size marker (in kb) is shown on the left.

FIG. 10 shows graphs summarizing experiments demonstrating that pantothenate auxotrophy leads to attenuation of ΔpanCD mutant in mice. a. Survival of BALB/c SCID mice (n=12 per group) infected intravenously with H37Rv (○) or panCD-complemented strain (●) or ΔpanCD mutant (▲) or $M.$ $bovis$ BCG-P (□). b. Bacterial numbers in the spleen (○), liver (□) and lung (Δ) of SCID mice infected intravenously with H37Rv or the bacterial numbers in the spleen (●), liver (■) and lung (▲) of mice infected with ΔpanCD mutant. c. Survival of immunocompetent BALB/c mice (n=16 per group) infected with H37Rv (○) or panCD-complemented strain (●) or ΔpanCD mutant (▲). d, e, f. Bacterial numbers in lung (d), spleen (e) and liver (f) of immunocompetent BALB/c mice infected intravenously with either H37Rv (○), panCD-complemented strain (●) or ΔpanCD mutant (▲). Data are means±standard errors of four to five mice per group.

FIG. 11 shows micrographs (Panels a-d) and graphs (Panels e and f) summarizing experiments demonstrating that the ΔpanCD mutant produces less tissue pathology in lungs of infected BALB/c mice and protects mice against challenge with virulent $M.$ $tuberculosis$. Panel a. Severe consolidating granulomatous pneumonia (*) obliterating the normal lung parenchyma at 3 weeks post-infection with H37Rv. Panel b. Severe consolidating granulomatous pneumonia (*) obliterating the normal lung parenchyma at 3 weeks post-infection with the panCD-complemented strain, similar to the wild type strain. Panel c. Mild lung infection caused by the ΔpanCD mutant at 3 weeks post-infection. Localized multifocal granulomas (arrows) scattered widely in the lung. Most of the lung is normal alveolar spaces and airways. Panel d. Lung of mouse infected with ΔpanCD mutant examined histologically at 23 weeks post-infection. Occasional focal, mild perivascular and interstitial infiltrations composed of predominately lymphocytes (arrows). Most of the lung is normal alveolar spaces and airways. Panels e, f (graphs). The attenuated ΔpanCD mutant protects mice against aerogenic challenge with virulent $M.$ $tuberculosis$ Erdman. Subcutaneously immunized mice were challenged after 90 days through the aerosol route. The CFU numbers reflect the bacterial burden at 28 days post aerosol challenge in the lung (e) and spleen (f). Naive mice—black fill; mice infected with 1 dose panCD—light shade, second bar from left; mice infected with 2 doses panCD —dark shade; mice infected with BCG-P—light shade, rightmost bar. In (e) and (f), * =P<0.05; **=P<0.01.

FIG. 12 shows autoradiographs of Southern analysis of the NcoI-digested genomic DNA isolated from the wild type and the ΔRD1 mutants generated using specialized transduction in $M.$ $tuberculosis$ and $M.$ $bovis$. Lanes: 1—$M.$ $tuberculosis$ H37Rv; 2—$M.$ $tuberculosis$ H37Rv ΔRD1; 3—$M.$ $tuberculosis$ Erdman; 4—$M.$ $tuberculosis$ Erdman ΔRD1; 5 —$M.$ $tuberculosis$ CDC1551; 6 —$M.$ $tuberculosis$ CDC1551 ΔRD1; 7 —$M.$ $bovis$ Ravenel; and 8 —$M.$ $bovis$ Ravenel ΔRD1. The probes used in the Southern analysis was either DFS (left) or IS6110-specific sequence (right).

FIG. 13 shows graphs summarizing data confirming that deletion of RD1 in $M.$ $tuberculosis$ and $M.$ $bovis$ confers an attenuation of virulence for $M.$ $tuberculosis$ and $M.$ $bovis$, as indicated by these Time to death curves of mice infected intravenously with $2\times10^6$ CFU mycobacteria. Panel A, SCID mice infected with *M. tuberculosis* H37Rv (■), *M. tuberculosis* H37Rv ΔRD1 (□), *M. tuberculosis* Erdman (●), *M. tuberculosis* Erdman ΔRD1 (○), *M tuberculosis* CDC 1551 (▲), *M. tuberculosis* CDC 1551 ΔRD1 (Δ), *M. bovis* Ravenel (▼), M bovis Ravenel ΔRD1 (Δ); Panel B, SCID mice infected intravenously with *M. tuberculosis* H37Rv (●), *M. tuberculosis* ΔRD1 (■), *M. tuberculosis* ΔRD1::2F9 (▲), *M. bovis* Ravenel (○), *M. bovis* Ravenel ΔRD1 (□), and *M. bovis* BCG (Δ); Panel C, BALB/c mice were infected with *M. tuberculosis* H37Rv (○), *M. tuberculosis* ΔRD1 (Δ), and *M. bovis* BCG (□).

FIG. 14 are graphs summarizing experiments demonstrating the clearance of the lysine auxotroph in SCID mice. The viable bacterial counts are shown for the spleens, livers, and lungs of SCID mice injected intravenously with the lysine auxotroph strain and the prototrophic control strain. Three mice were assayed at each time point. The error bars indicate the standard deviations of the mean values. Note that the counts at time zero are the counts obtained at 24 hours post-injection, as described in Example 5. Panels A, B and C show the log of the viable bacteria in each organ after injection with $1\times10^7$ CFU of the $Lys^-$ *M tuberculosis* mutant $mc^23026$ (□), or $1\times10^7$ CFU of the complemented $Lys^+$ *M. tuberculosis* strain $mc^23026$/pYUB651 (■).

FIG. 15 is graphs summarizing experimental results of experiments that establish the vaccine efficacy of the *M. tuberculosis* lysine auxotroph $mc^23026$. C57B1/6 mice were injected intravenously with $1\times10^6$ CFU of the *M. tuberculosis* lysine auxotroph $mc^23026$, followed by one or two additional injections at 4-week intervals. Five mice were sacrificed weekly after each immunization and the viable bacteria counts of the auxotroph determined in the lungs and spleens. Control mice were given a similar amount of BCG-Pasteur or only PBST. Shown in Panel A is the clearance of the auxotroph from the lungs of the mice after each immunization period; one injection (■), two injections (◇), and three injections (●). Three months after the initial immunization the vaccinated and control mice were challenged with virulent *M tuberculosis* Erdman by the aerosol route. Five challenge mice were sacrificed following the challenge period and the lung homogenates plated to check the viable counts of the challenge inoculum. Groups of vaccinated and control mice were sacrificed at 14, 28, and 42 days later and the lung and spleen homogenates plated to determine viable colony forming units. Shown in Panel B are the viable challenge bacteria per lung of mice given one dose of the *M. tuberculosis* lysine auxotroph, and in panel C, the viable challenge bacteria per lung of mice given two doses of the auxotroph. Key: Viable challenge bacteria per lung of mice given the *M. tuberculosis* lysine auxotroph $mc^2$3026 (■) BCG-Pasteur (◇), or PBST (○). P values are indicated in the figure. Note that the results shown here are for the lungs. Similar results (not shown) were obtained from the spleens in all the experiments.

FIG. 16 shows a graph summarizing experiments establishing the survival curves of mice immunized three times with the *M. tuberculosis* lysine auxotroph $mc^2$3026. C57B1/6 mice were injected intravenously with $1\times10^6$ CFU of the *M. tuberculosis* lysine auxotroph $mc^2$3026, followed by two more injections at 4 week intervals, and challenged as described in Example 5. The percent survival is shown for mice immunized thrice with the *M. tuberculosis* lysine auxotroph $mc^2$3026 (■, 5 mice total), once with BCG-Pasteur (♦, 5 mice), and for the PBST controls (●, 10 mice).

FIG. 17 shows graphs summarizing experimental results establishing that the virulence of strain $mc^2$6030 is highly attenuated in SCID mice and BALB/c mice.

FIG. 18 shows graphs summarizing experimental results measuring growth of various strains of *M. tuberculosis* in spleen (Panel A) and lungs (Panel B) of C57BL/6 mice.

Figure 19:
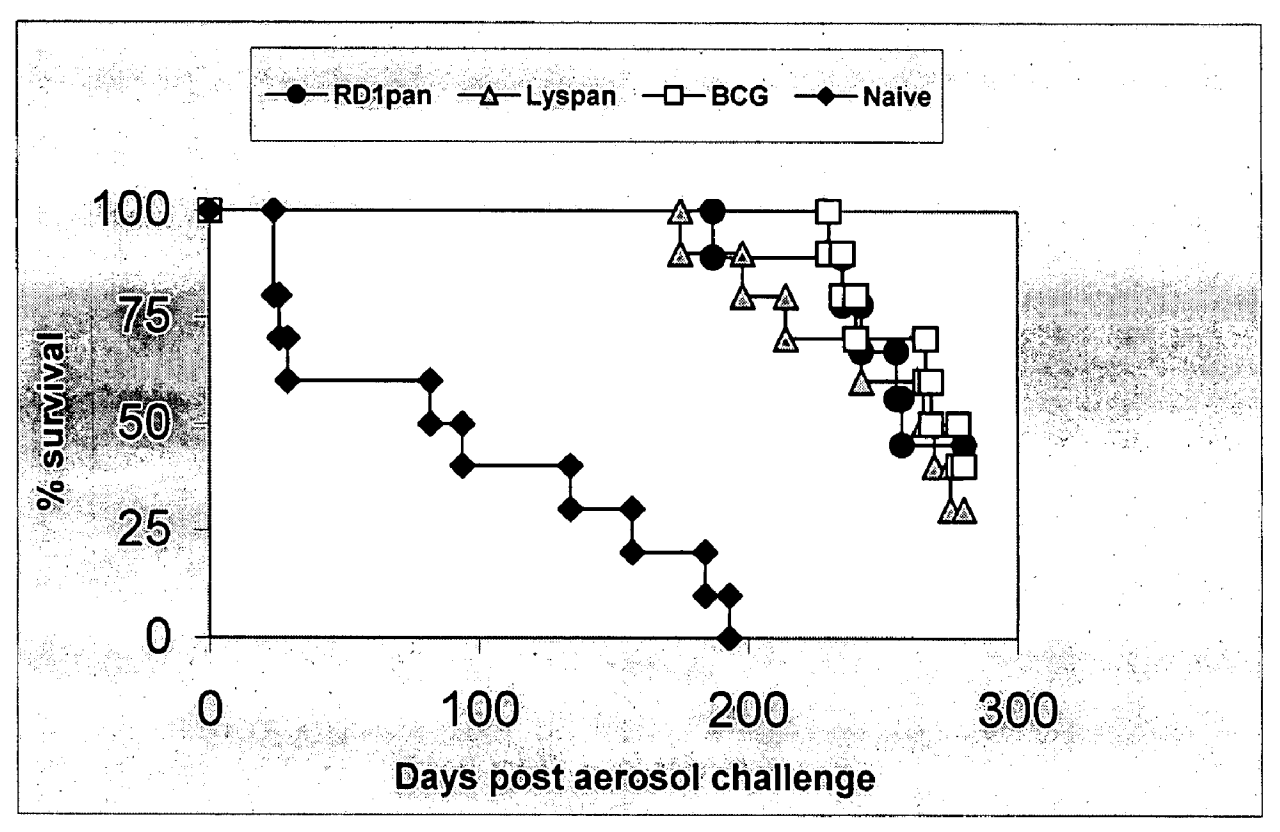

FIG. 19 is a graph summarizing experimental results establishing that immunization with $mc^2$6020 and $mc^2$6030 protects mice against TB as effectively as BCG. This graph shows the survival of C57BI/6 mice challenged with virulent *M. tuberculosis* Erdman through the aerosol route three months after a single dose subcutaneous immunization with either BCG, $mc^2$6020 (ΔlysAΔpanCD) or $mc^2$6030 (ΔRD1ΔpanCD) and compared to non-immunized naive mice. There were 12 to 15 mice in each survival group.

FIG. 20 shows graphs summarizing experimental results establishing that *M. tuberculosis* double deletion mutants are highly attenuated in SCID mice. A dose of $10^5$ $mc^2$6020 or $mc^2$6030 were intravenously inoculated into SCID mice (10 per group) and time to death assessments were performed. While the same dose of *M. tuberculosis* and BCG killed mice in 40 or 90 days, respectively, the mice infected with $mc^2$6020 or $mc^2$6030 survived over 400 or 250 days, respectively.

FIG. 21 is graphs of experimental results showing the immune response to PPD in ΔleuD/ΔpanCD immunized guinea pigs. Outbred female Hartley guinea pigs were immunized i.d. with $5\times10^5$ CFU ΔleuD/ΔpanCD, followed six weeks later by a second immunization with $3\times10^6$ CFU ΔleuD/ΔpanCD. At the time that the above group received the booster vaccination, a second group received a single immunization with $3\times10^6$ CFU ΔleuD/ΔpanCD, while a third group received $3\times10^6$ CFU BCG-P. A control group was unimmunized. Each experimental group consisted of 5 animals. For Panel A, five weeks after the last immunization, PBMCs were isolated from whole blood by Ficoll-Histopaque density-gradient centrifugation. Two individual guinea pigs were tested per treatment group. PBMCs ($2\times10^5$/well) were incubated at 37° C. in 5% $CO_2$ for 5 days with media alone, phytohemagglutinin A (PHA, Sigma, St. Louis, Mo.) (data not shown) or 5 μg PPD (Mycos Research, LLC, Loveland, Colo.) per well. Proliferation was assessed on day 5 by [$^3$H]-thymidine (0.5 μCi/well) incorporation for 6 hours. Cells were harvested using a Skatron cell harvester and incorporated thymidine was measured using a beta-plate liquid scintillation counter. Values are expressed as mean CPM of triplicate samples. Error bars represent standard deviation from the mean. For Panel B, DTH responses were determined 7 weeks after the last immunization. 4TU (not shown) or 40 TU of PPD (FDA/CBER, Bethesda, Md.) was injected i.d. in the right flank, and the diameter of induration was measured at 24 h. Mean induration diameters (in mm) (indicated by horizontal line) were 11.6±2.3 for BCG-P-immunized animals, 11.0±2.3 for animals immunized once with ΔleuD/ΔpanCD and 13±2.4 for animals immunized twice with ΔleuD/ΔpanCD. *=P<0.001 as determined by one-way ANOVA analysis.

FIG. 22 is a graph of experimental results showing protection of guinea pigs against aerosol challenge with *M. tuberculosis* H37Rv. Outbred female Hartley guinea pigs (n=5 per group) were immunized i.d. once with *M. bovis* BCG Pasteur (BCG-P), once with ΔleuD/ΔpanCD or twice (6 weeks apart) with ΔleuD/ΔpanCD. A negative control group was unimmunized. Seven weeks subsequent to the last immunization, animals were challenged via the aerosol route with 20 CFU *M. tuberculosis* H37Rv. Spleen and right caudal lung bacterial burdens were determined 5 weeks post-challenge. Error bars represent standard deviations from the mean. *=P<0.001, **=P<0.01 as determined by one-way ANOVA analysis.

FIG. 23 shows histopathology of the lungs of vaccinated and unvaccinated guinea pigs 5 weeks after an aerosol challenge with *M. tuberculosis*. Panels A and B show a left caudal lung section from an unvaccinated guinea pig showing severe multifocal and spreading granulomatous pneumonia with central caseation necrosis. Panel B shows a higher power photomicrograph showing the spreading granulomatous reaction composed of epithelioid cells accompanied by large numbers of macrophages and lymphocytes, surrounding the central caseation necrosis. Panels C and D show the lung of a guinea pig vaccinated with BCG-P. The lower power photomicrograph (C) shows multiple sites of focal perivascular and interstitial discrete accumulations of moderate to large numbers of lymphocytes (arrowheads). Also shown are scattered granulomatous foci composed of epithelioid cells and numerous lymphocytes (arrows). Very mild caseation necrosis was evident in a few of the granulomas. Panel D is a higher power photomicrograph showing perivascular lymphoid accumulations (large arrows). Panels E and F show the lung of a guinea pig vaccinated once with ΔleuD/ΔpanCD. In Panel E, the lungs had lower numbers of discrete focal granulomas widely scattered in the parenchyma (arrows). Multifocal small, localized lymphocytic accumulations (arrowheads) were apparent, similar to those in the BCG vaccinated guinea pigs. Panel F is a higher power photomicrograph showing a discrete granuloma composed of predominately epithelioid cells accompanied by low to moderate numbers of lymphocytes and focal lymphocytic accumulations in the parenchyma and perivascular regions. A few granulomas had mild central caseation necrosis. Panels G and H shows the lung from a guinea pig vaccinated twice with ΔleuD/ΔpanCD, exhibiting extensive coalescing granulomatous pneumonia, particularly along airways (see G). The spreading areas of inflammation were composed of epithelioid cells and moderate numbers of lymphocytes, accompanied by macrophages. Many of the granulomas showed mild to moderate central caseation necrosis, considerably less pronounced than in the unvaccinated guinea pigs, but more prominent than in BCG- and singly-immunized animals.

FIG. 24 shows a morphometric analysis of lung pathology. The areas of lung lesions were measured on hematoxylin and eosin stained left caudal lobe sections by use of Scion Image software. These measurements were used to calculate the total area of the lung section occupied by diseased tissue. The percentage of diseased tissue was significantly reduced in BCG-P- and ΔleuD/ΔpanCD-immunized animals relative to naïve animals. *=P<0.01 as determined by one-way ANOVA analysis.

FIG. 25 shows a Southern blot analysis of wild-type *M. tuberculosis* H37Rv 102J23, ΔleuD/ΔpanCD, ΔleuD and ΔpanCD. Genomic DNAs from wild-type (wt) *M. tuberculosis* H37Rv 102J23 (Lane 1), ΔleuD/ΔpanCD (Lane 2), and the single auxotrophs ΔleuD (Lane 3) and ΔpanCD (Lane 4) were isolated, digested and hybridized as follows. For Panel A, genomic DNA was digested with Acc65I and probed with the 600 bp leuD flanking region to yield a 2.43 kb wt and 2.20 kb ΔleuD hybridizing band. For Panel B, genomic DNA was digested with BssHII and probed with a 716 bp probe downstream of the panCD operon, to detect a 1.48 kb wt and 2.65 kb ΔpanCD allele (Sambandamurthy et al., 2002). Molecular size markers (kb) are indicated on the left.

FIG. 26 is graphs showing that deletion of leuD and panCD confers leucine and pantothenate auxotrophy. Bacterial strains were cultured in Middlebrook 7H9 liquid broth with or without leucine (50 μg/ml) and pantothenate (24 μg/ml) supplementation where necessary, then pelleted, washed and resuspended in media with and without leucine and or pantothenate supplementation (as indicated in the figure inset). In Panel A, filled symbols (●,▲,▼,♦) represent ΔleuD/ΔpanCD growth with or without supplementation as indicated in figure inset. Wild-type *M. tuberculosis* H37Rv 102J23 (□) was cultured in 7H9 medium with no supplementation. For Panel B, ΔleuD/ΔpanCD (▲), ΔleuD/ΔpanCD complemented with leuD and panCD (Δ) and wild-type *M. tuberculosis* H37Rv 102J23 (□) were cultured in minimal 7H9 medium with no supplementation. The $OD_{600}$ of the broth cultures were determined daily.

FIG. 27 shows the DTH response to PPD in BCG- and ΔleuD/ΔpanCD-immunized and naive guinea pigs. Outbred female Hartley guinea pigs were (A) not immunized to serve as a negative control group, (B) immunized once i.d. with $3\times10^6$ CFU BCG-P, (C) immunized once with $3\times10^6$ CFU ΔleuD/ΔpanCD, or (D) immunized with $5\times10^5$ CFU ΔleuD/ΔpanCD, followed six weeks later by a second immunization with $3\times10^6$ CFU ΔleuD/ΔpanCD. Each experimental group consisted of 5 animals. DTH responses were determined 7 weeks after the last immunization. 4 TU (arrowhead) and 40 TU (arrow) of PPD (FDA/CBER, Bethesda, Md.) was injected i.d. in the right flank, and the diameter of induration was measured at 24 h. Representative examples of DTH responses at 24 h are shown. Blue ink marks delineate the injection site, and are not a measure of the diameter of induration. Mean induration diameters (in mm) were 11.6±2.3 for BCG-P-immunized animals, 11.0±2.3 for animals immunized once with ΔleuD/ΔpanCD and 13±2.4 for animals immunized twice with ΔleuD/ΔpanCD.

DETAILED DESCRIPTION OF THE INVENTION

Figure 1:
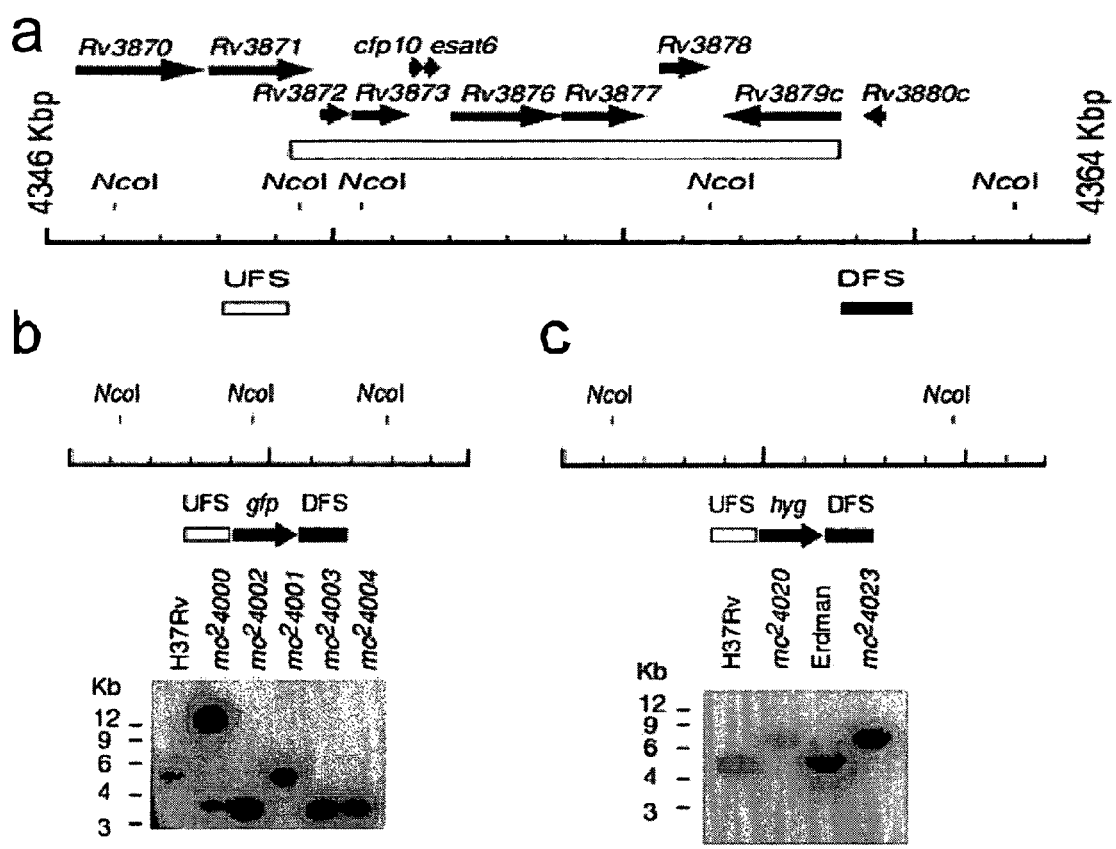

The present invention is based in part on the discovery that virulent mycobacteria in the *M. tuberculosis* complex that have deletions in the RD1 region, or in a region that controls production of a vitamin or the amino acids leucine or lysine, are attenuated in virulence but are capable of sustaining viability and growth in a mammalian host, and are also capable of protecting against a challenge by a virulent *M. tuberculosis* complex mycobacterium.

Thus, in some embodiments, the invention is directed to non-naturally occurring *Mycobacterium tuberculosis* that comprise a deletion of an RD1 region or a region controlling production of a vitamin or the amino acids leucine or lysine. These *M. tuberculosis* preferably exhibit attenuated virulence in a mammal when compared to the *M. tuberculosis* without the deletion.

A host organism can be inoculated with the mycobacteria of the present invention by any of a number of ways known in the art. These include oral ingestion, gastric intubation, or broncho-nasal-ocular spraying. Other methods of administration include intravenous, intramuscular, intramammary, or, preferably, subcutaneous or intradermal injection. The immunization dosages required can be determined without undue experimentation. One or two dosages of avirulent mycobacteria at $1-2\times10^6$ colony forming units (CFU) have previously been used, but other dosages are contemplated within the scope of the invention. Multiple dosages can be used as needed to provide the desired level of protection from challenge.

It is well known in the art that in order to elicit an immune response with a live vaccine such as an avirulent mycobacteria, it is preferred that the vaccine organism can sustain an infection in the immunized host, to provide a sustained exposure of the host's immune system to the organism. Therefore, in various preferred embodiments, the *M. tuberculosis* of the invention are capable of sustaining an infection in the host. The ability to sustain infection can be measured without undue experimentation by any of a number of ways described in the art. With the mycobacteria of the present invention, a preferred way of measuring sustained infection is by determining whether viable mycobacteria of the inoculated strain will remain resident in an immunocompetent mouse (e.g., BALB/c or C57BL/6 strain) for more than four weeks. More preferably, the inoculated mycobacteria will remain resident in the mouse for at least ten weeks. In the most preferred embodiments, viable mycobacteria of the inoculated strain will remain resident in the mouse for at least 20 weeks.

Preferably, the attenuated mycobacteria of the invention are capable of protecting a mammal from challenge by a virulent *M. tuberculosis* complex mycobacteria. This ability can be determined by any of a number of ways provided in the literature. A preferred method is aerogenically treating an immunocompetent mouse with the virulent mycobacteria, as described in Examples 1 and 2. Aerogenic challenge is preferred because that most closely mimics natural infection. The skilled artisan would understand that the ability of an avirulent mycobacterium to protect a mouse from challenge from a virulent mycobacterium is indicative of the ability of the avirulent mycobacterium to protect a human, including a human child, from tuberculosis infection. A more stringent test of an avirulent mycobacterium to prevent infection by a virulent challenge is to use an immunocompromised mammal such as a SCID mouse.

The deletion of the RD1 region or the region controlling production of a vitamin or the amino acids leucine or lysine is contemplated in these embodiments with any *M tuberculosis* strain. Preferably, the strain is a virulent strain, since those strains would be most likely to sustain an infection after the deletion is made. Preferred *M. tuberculosis* strains are the H37Rv and CDC1551 strain, because the genetics of those strains are very well known.

In some aspects of these embodiments, the deletion is of the RD1 region (see Example 1). Strains with these deletions can be determined by any means in the art, preferably by molecular genetic means, for example by hybridization methods (e.g., Southern blot using a probe from the RD1 region) or by amplification methods (e.g., PCR using primers to amplify a portion of the RD1 region). An example of an *M. tubercu-*

*losis* RD1 region (from H37Rv) is provided herein as SEQ ID NO:1. The skilled artisan could identify analogous RD1 regions from other *M. tuberculosis* complex mycobacteria without undue experimentation. Those RD1 regions would be expected to have strong homology to SEQ ID NO:1, at least 80% homologous to SEQ ID NO:1. However, it is to be understood that virulent *M. tuberculosis* can be rendered avirulent by deletions in a portion of the RD1 region. Therefore, non-naturally occurring *M. tuberculosis* that have a partial deletion in the RD1 region are envisioned as within the scope of the invention, provided the deletion can cause a virulent M tuberculosis to become avirulent. It is expected that such *M. tuberculosis* with partial RD1 deletions can still sustain an infection in a mammal and protect against challenge by a virulent *M. tuberculosis*.

In embodiments where the deletion is in a region controlling production of a vitamin, the deletion can be in any genetic element leading to loss of production of the vitamin, including structural genes for enzymes involved in the biosynthesis of the vitamin, and genetic control elements such as promoters, enhancers, etc.

Deletion of a region controlling production of any essential vitamin or the amino acids leucine or lysine or their precursors is contemplated as within the scope of the invention. As used herein, an essential vitamin is defined by its normal usage, that is, a small molecular weight compound that is required as a cofactor for the efficient function of an essential enzyme or enzymes. Nonlimiting examples include vitamin A, thiamin (B1), riboflavin (B2), nicotinic acid (niacin)/nicotinamide/nicotinamide adenine dinucleotide (NAD)/nicotinamide adenine dinucleotide phosphate (NADP/coenzyme II), pantothenate (pantothenic acid/B5), pyridoxine (B6), folic acid, B12, biotin, C, D, E and K. Preferred vitamin targets for deletion include nicotinamide and pantothenate (see Example 2). Methods for determining whether a mycobacterium has deletions leading to the loss of production of any of these vitamins are within the scope of the art.

Deletions leading to the loss of any of these vitamins or the amino acid leucine or lysine would be expected to lead to attenuated virulence of an otherwise virulent mycobacterium in the *M. tuberculosis* complex. Any of those strains would also be expected to sustain an infection in a mammal.

Preferred vitamin targets are pantothenate and nicotinamide adenine dinucleotide (NAD)(see Example 2). A preferred pantothenate deletion is of structural genes in the pantothenate biosynthetic operon, most preferably the panC and panD genes, the combined mutation being ΔpanCD. An example of a deletion of those genes is the deletion of the sequence from *M. tuberculosis* H37Rv provided herein as SEQ ID NO:2. Similarly, a preferred NAD deletion is in the structural genes of the NAD biosynthetic operon, most preferably the nad B and C genes, the combined mutation being ΔnadBC. An example of a deletion in those genes is the deletion of the sequence from *M. tuberculosis* H37Rv provided herein as SEQ ID NO:3.

In similar embodiments, the invention is directed to any of the above-described *M. tuberculosis* that are produced by deleting an RD1 region or a region controlling production of a vitamin or the amino acids leucine or lysine. The deletion can be made by serial in vitro passage of a virulent *M. tuberculosis* (as the well-known *M. bovis* BCG was made) and selection for the desired deletion. More preferably, however, the deletion is made by genetic engineering, since such genetic methods allow precise control of the deletion being made.

Various methods of making deletions in mycobacteria are known in the art. Nonlimiting examples include specialized transduction (see, e.g., U.S. Pat. No. 6,271,034, Example 1 and Example 2), and sequential two-step recombination (see Example 1). The latter method can usefully employ a sacB selective marker (Example 1).

Since, in preferred embodiments of the invention, the mycobacteria exhibit attenuated virulence and can sustain an infection in a mammal, these mycobacteria can usefully further employ a foreign DNA stably integrated into the genome of the mycobacteria, such that the mycobacteria can express a gene product coded by the foreign DNA. See, e.g., U.S. Pat. No. 5,504,005.

Thus, it is apparent that the present invention has wide applicability to the development of effective recombinant vaccines against bacterial, fungal, parasite or viral disease agents in which local immunity is important and might be a first line of defense. Non-limiting examples are recombinant vaccines for the control of bubonic plague caused by *Yersinia pestis*, of gonorrhea caused by *Neisseria gonorrhoea*, of syphilis caused by *Treponema pallidum*, and of venereal diseases or eye infections caused by *Chlamydia trachomatis*. Species of *Streptococcus* from both group A and group B, such as those species that cause sore throat or heart disease, *Neisseria meningitidis, Mycoplasma pneumoniae, Haemophilis influenzae, Bordetella pertussis, Mycobacterium leprae, Streptococcus pneumoniae, Brucella abortus, Vibrio cholerae, Shigella* spp., *Legionella pneumophila, Borrelia burgdorferi, Rickettsia* spp., *Pseudomonas aeruginosa*, and pathogenic *E. coli* such as ETEC, EPEC, UTEC, EHEC, and EIEC strains are additional examples of microbes within the scope of this invention from which foreign genes could be obtained for insertion into mycobacteria of the invention. Recombinant anti-viral vaccines, such as those produced against influenza viruses, are also encompassed by this invention. Recombinant anti-viral vaccines can also be produced against viruses, including RNA viruses such as Picornaviridae, Caliciviridae, Togaviridae, Flaviviridae, Coronaviridae, Rhabdoviridae, Filoviridae, Paramyxoviridae, Orthomyxoviridae, Bunyaviridae, Arenaviridae, Reoviridae or Retroviridae; or DNA viruses such as Hepadnaviridae, Paroviridae, Papovaviridae, Adenoviridae, Herpesviridae or Poxyiridae.

Recombinant vaccines to protect against infection by pathogenic fungi, protozoa or parasites are also contemplated by this invention.

The avirulent microbes of the present invention are also contemplated for use to deliver and produce foreign genes that encode pharmacologically active products that might stimulate or suppress various physiological functions (i.e., growth rate, blood pressure, etc.). In such microbes, the recombinant gene encodes said pharmacologically active products.

By immunogenic agent is meant an agent used to stimulate the immune system of an individual, so that one or more functions of the immune system are increased and directed towards the immunogenic agent. Immunogenic agents include vaccines.

An antigen or immunogen is intended to mean a molecule containing one or more epitopes that can stimulate a host immune system to make a secretory, humoral and/or cellular immune response specific to that antigen.

In preferred embodiments, the foreign DNA encodes an antigen, an enzyme, a lymphokine, an immunopotentiator, or a reporter molecule. Preferred examples include antigens from *Mycobacterium leprae, Mycobacterium tuberculosis*, malaria sporozoites, malaria merozoites, diphtheria toxoid, tetanus toxoids, *Leishmania* spp., *Salmonella* spp., *Mycobacterium africanum, Mycobacterium intracellulare, Mycobacterium avium, Treponema* spp., Pertussis, Herpes virus, Measles virus, Mumps virus, *Shigella* spp., *Neisseria* spp., *Borrelia* spp., rabies, polio virus, human immunodeficiency virus, snake venom, insect venom, and *Vibrio cholera*; steroid enzymes; interleukins 1 through 7; tumor necrosis factor α and β; interferon α, β, and γ; and reporter molecules luciferase, β-galactosidase, β-glucuronidase and catechol dehydrogenase.

The scope of the present invention includes novel mycobacteria in the *M. tuberculosis* complex that are genetically engineered to comprise a deletion of an RD1 region or a region controlling production of a vitamin or the amino acids leucine or lysine. The scope of the deletions and the characteristics of these mycobacteria are as with the *M. tuberculosis* mycobacteria described above. These mycobacteria include any in the *M. tuberculosis* complex, including *M. africanum*, *M. bovis* including the BCG strain and the subspecies *caprae*, *M. canettii*, *M. microti*, *M tuberculosis* and any other mycobacteria within the *M. tuberculosis* complex, now known or later discovered. Preferred species are *M. bovis*, including the BCG strain, and *M. tuberculosis*, since those species are the most important as causes of mammalian diseases, such as tuberculosis in humans and *M. bovis* infection in cows.

Also included as within the scope of the invention is any non-naturally occurring mycobacterium in the *M. tuberculosis* complex having a deletion of a region controlling production of a vitamin. These mycobacteria preferably are capable of sustaining an infection in a mammal. The scope of the deletions and the characteristics of these mycobacteria are as with the *M. tuberculosis* and other mycobacteria described above.

The inventors have also discovered that mycobacteria in the *M. tuberculosis* complex that are auxotrophic for leucine or lysine have attenuated virulence and protect a mammal from challenge by a virulent mycobacterium. See Example 5. Thus, in some embodiments, the invention is directed to non-naturally occurring mycobacteria in the *M. tuberculosis* complex that comprise a deletion of a region controlling production of leucine or lysine. These mycobacteria are capable of sustaining an infection in an immunocompetent mouse for at least 20 weeks. As with previously described embodiments, these mycobacteria can be any species in the *M. tuberculosis* complex. However, due to their importance as disease organisms, it is preferred mycobacteria are *M. tuberculosis* and *M. bovis*, e.g., *M. bovis* BCG.

These mycobacteria would also be expected to exhibit attenuated virulence in a mammal when compared to the mycobacteria without the deletion. Additionally, they would be expected to provide protection to a mammal from challenge by a virulent mycobacterium in the *M. tuberculosis* complex. A preferred deletion is a ΔleuD deletion or ΔlysA deletion, for example as provided herein as SEQ ID NO:5 and SEQ ID NO:4, respectively.

When constructing a live vaccine that is an attenuated pathogen due to a deletion, it is often desirable to include a second deletion, to better assure the safety of the vaccine. Second deletions in any of the above-described mycobacteria are thus contemplated as within the scope of the invention. The second deletion preferably can also attenuate virulence of an otherwise virulent mycobacterium in the *M. tuberculosis* complex. This second deletion can be the RD1 region if the first deletion is not. The second deletion can also be a deletion that would cause a prototrophic mycobacterium to be auxotrophic, or any other deletion that could improve the safety or efficacy of the mycobacterium in protecting against infection. Nonlimiting examples include deletions in a gene or genes controlling production of an amino acid or a nucleotide, or a vitamin not eliminated by the first mutation.

The inventors have also discovered that two attenuating deletions in a mycobacterium in the *M. tuberculosis* complex provides a high level of protection to a mammal from challenge by a virulent mycobacterium. See Example 6.

Thus, in some embodiments, the invention is directed to mycobacteria in the *M tuberculosis* complex which are genetically engineered to comprise two deletions. Preferably, each of the two deletions are capable of individually attenuating virulence when engineered into a virulent mycobacterium in the *M. tuberculosis* complex.

Preferred embodiments of these mycobacteria are as with the other mycobacteria of the invention, e.g., the mycobacterium is preferably a *Mycobacterium tuberculosis*; the mycobacterium is preferably capable of sustaining an infection in an immunocompetent mouse for at least 20 weeks; and the mycobacterium is capable of protecting the mammal from challenge by a virulent mycobacterium.

As with the other mycobacteria previously described, the two attenuating deletions can be any deletions that are individually capable of attenuating virulence of an otherwise virulent strain. Preferred deletions are deletions of an RD1 region (e.g., a deletion of SEQ ID NO:1), deletions of a region controlling production of a vitamin, or deletions of a region controlling the production of an amino acid, as previously discussed. A preferred deletion of a region controlling production of a vitamin is the ΔpanCD deletion, e.g., as disclosed in Examples 2 and 3, discussing attenuated strains having a deletion of SEQ ID NO:2. Preferred deletions of regions controlling production of amino acids are those regions controlling production of proline, tryptophan, leucine or lysine. See, also, Examples 5 and 6, describing strains having a ΔlysA deletion (SEQ ID NO:4), or two mutations including one with a ΔlysA deletion; and Example 7 describing strains having a ΔleuD deletion (SEQ ID NO:5), or two mutations including one with a ΔleuD deletion.

In additional embodiments, the invention is directed to tuberculosis vaccines made using any of the above described mycobacteria, in a pharmaceutically acceptable excipient. These vaccines are capable of protecting the mammal from challenge by a virulent *M. tuberculosis* complex mycobacteria. In some preferred embodiments, the mycobacterium is a *Mycobacterium bovis* and the mammal is a cow; in other preferred embodiments, the mycobacterium is *M. tuberculosis* and the mammal is a human, e.g., a human child.

By vaccine is meant an agent used to stimulate the immune system of an individual so that protection is provided against an antigen not recognized as a self-antigen by the immune system. Immunization refers to the process of inducing a continuing high level of antibody and/or cellular immune response in which T-lymphocytes can either kill the pathogen and/or activate other cells (e.g., phagocytes) to do so in an individual, which is directed against a pathogen or antigen to which the organism has been previously exposed. The phrase "immune system" refers herein to the anatomical features and mechanisms by which a mammal produces antibodies against an antigenic material which invades the cells of the individual or the extra-cellular fluid of the individual and is also intended to include cellular immune responses. In the case of antibody production, the antibody so produced can belong to any of the immunological classes, such as immunoglobulins, A, D, E, G or M. Immune responses to antigens are well studied and widely reported. A survey of immunology is provided in Elgert (1996) and Stites et al. (1991).

The pharmaceutical carrier or excipient in which the vaccine is suspended or dissolved may be any solvent or solid or encapsulating material. The carrier is non-toxic to the inoculated individual and compatible with the microorganism or antigenic gene product. Suitable pharmaceutical carriers are known in the art and, for example, include liquid carriers, such as normal saline and other non-toxic salts at or near physiological concentrations, and solid carriers, such as talc or sucrose. Gelatin capsules can serve as carriers for lyophilized vaccines. Adjuvants may be added to enhance the antigenicity if desired. When used for administering via the bronchial tubes, the vaccine is preferably presented in the form of an aerosol. Suitable pharmaceutical carriers and adjuvants and the preparation of dosage forms are described in, for example, Gennaro (1985).

Similarly, the invention is directed to methods of protecting a mammal from a virulent mycobacterium in the *M. tuberculosis* complex. The methods comprise treating the mammal with any of the above-described vaccines.

The vaccines can be administered by oral ingestion, gastric intubation, or broncho-nasal-ocular spraying, intravenous, intramuscular, intramammary, or, preferably, by subcutaneous or intradermal injection. The immunization dosages required can be determined without undue experimentation. One or two dosages of avirulent mycobacteria at $1-2 \times 10^6$ colony forming units (CFU) have previously been used, but other dosages are contemplated within the scope of the invention. Multiple dosages can be used as needed to provide the desired level of protection from challenge (see, e.g., Example 5).

The present invention is also directed to methods of preparing a tuberculosis vaccine. The methods comprise deleting an RD1 region or a region controlling production of a vitamin or the amino acids leucine or lysine from a mycobacterium in the *M. tuberculosis* complex to produce any of the mycobacteria previously described.

In further embodiments, the invention is directed to non-naturally occurring *Mycobacterium tuberculosis* auxotrophic for leucine and pantothenate. In these embodiments, the *M. tuberculosis* exhibits attenuated virulence in a mammal when compared to the *M. tuberculosis* without the leucine and pantothenate auxotrophy.

In these embodiments, the *M. tuberculosis* is preferably capable of protecting the mammal from challenge by a virulent *M. tuberculosis*. Additionally, the *M. tuberculosis* can be derived from any known *M. tuberculosis* strain, including an H37Rv strain (Example 7).

The leucine auxotrophy in these embodiments can be due to any deletion now known or later discovered to cause leucine auxotrophy. In some preferred embodiments, the leucine auxotrophy is due to a deletion in a leuD gene, for example where the deleted region of the leuD gene has at least 95% homology to SEQ ID NO:5.

Additionally, the pantothenate auxotrophy in these embodiments can be due to any deletion now known or later discovered to cause pantothenate auxotrophy. In some preferred embodiments, the pantothenate auxotrophy is due to a deletion in a panCD gene, for example where the deleted region of the panCD gene has at least 95% homology to SEQ ID NO:2.

In some preferred embodiments, the leucine auxotrophy is due to a deletion in a leuD gene and the pantothenate auxotrophy is due to a deletion in a panCD gene, for example where the deleted region of the leuD gene has at least 95% homology to SEQ ID NO:5 and the deleted region of the panCD gene has at least 95% homology to SEQ ID NO:2.

Tuberculosis vaccines comprising these *M. tuberculosis* in a pharmaceutically acceptable excipient are also envisioned as part of the present invention. In these embodiments, the vaccine is capable of protecting a mammal from challenge by a virulent *M. tuberculosis*. Methods of protecting a mammal from a virulent *Mycobacterium tuberculosis* are also envisioned. These methods comprise treating the mammal with the *M. tuberculosis* pan/leu auxotrophic vaccines.

The present invention is also directed to mycobacteria in the *Mycobacterium tuberculosis* complex. The mycobacteria of these embodiments are genetically engineered to comprise a deletion causing leucine auxotrophy and a deletion causing pantothenate auxotrophy. Preferably, the leucine auxotrophy is from a deletion from a leuD gene and the pantothenate auxotrophy is from a deletion from a panCD gene.

The mycobacterium in these embodiments preferably exhibits attenuated virulence in a mammal when compared to the mycobacterium without the deletion.

The mycobacterium in these embodiments can be any *Mycobacterium* spp. within the *M. tuburculosis* complex. In some preferred embodiments, the mycobacterium is a *Mycobacterium bovis* or a *Mycobacterium tuberculosis*.

The deletion causing leucine auxotrophy can be from any gene now known or later discovered to lead to leucine auxotrophy. Where the deletion is of a portion of a leuD gene, the deletion can from any portion of the leuD gene, provided the deletion causes leucine auxotrophy. In some embodiments, the deletion of the leuD gene has at least 95% homology to SEQ ID NO:5. Similarly, the deletion causing pantothenate auxotrophy can be from any gene now known or later discovered to lead to pantothenate auxotrophy. Where the deletion is of a portion of a panCD gene, the deletion can be from any portion of the panCD gene that causes pantothenate auxotrophy. In some embodiments, the deletion has at least 95% homology to SEQ ID NO:2. In related embodiments, the deletion of the leuD gene has at least 95% homology to SEQ ID NO:5 and the deletion of the panCD gene has at least 95% homology to SEQ ID NO:2.

Tuberculosis vaccines of these pan/leu mycobacteria in a pharmaceutically acceptable excipient are also envisioned as part of the present invention. In these embodiments, the vaccine is capable of protecting a mammal from challenge by a virulent mycobacterium. Methods of protecting a mammal from a virulent mycobacterium are also envisioned. These methods comprise treating the mammal with the pan/leu auxotrophic vaccines.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1989); "Current Protocols in Molecular Biology" Volumes I-IV (Ausubel, R. M., ed. (1997); and "Cell Biology: A Laboratory Handbook" Volumes I-III (J. E. Celis, ed. (1994).

EXAMPLE 1

*Mycobacterium Tuberculosis* Having an RD1 Deletion has Attenuated Virulence and Protects Against Tuberculosis This example describes experimental methods and results that establish that deleting the RD1 region from a virulent *M.* tuberculosis attenuates the virulence of the *M. tuberculosis* in both immunocompetent and immunocompromised mice, and protects against subsequent challenge by a virulent *M. tuberculosis*.

Materials and Methods

Media and Cultures. The mycobacterial strains *M. tuberculosis* H37Rv, *M tuberculosis* Erdman and *M. bovis* BCG Pasteur were obtained from the Trudeau Culture Collection (Saranac Lake, N.Y.). They were cultured in Middlebrook 7H9 broth and 7H10 agar supplemented with 10% OADC, 0.5% glycerol, and 0.05% Tween 80. Cyclohexamide, which does not affect mycobacterial growth, was added to the 7H10 agar medium at 0.1% to avoid fungal contamination. To examine the colony morphology of mycobacteria, Tween 80 was not added to 7H10 agar medium. The acriflavin resistant strain (Hepper and Collins, 1984) of *M tuberculosis* Erdman grew in the presence of 20 µg of acriflavin per ml of medium.

DNA manipulation and construction of *M tuberculosis* ΔRD1. The following four primers were used to amplify upstream and downstream flanking sequences (UFS and DFS, respectively) for the construction of the RD1 deletion mutants. UFS was amplified using TH201: GGGGGCG-CACCTCAAACC (SEQ ID NO:5) and TH202: ATGTGC-CAATCGTCGACCAGAA (SEQ ID NO:6). DFS was amplified using TH203: CACCCAGCCGCCCGGAT (SEQ ID NO:7), and TH204: TTCCTGATGCCGCCGTCTGA (SEQ ID NO:8). Recognition sequences for different restriction enzymes were included at the ends of each primer to enable easier manipulation.

The unmarked deletion mutant of *M. tuberculosis* H37Rv, mc²4004, was generated by transformation (Snapper et al., 1988) using a sacB counterselection (Pelocic et al., 1996; Pavelka and Jacobs, 1999). Specifically, the plasmid pJH508 was created by first cloning UFS into KpnI and XbaI sites, then cloning DFS into EcoRI and HindIII sites of pJH12, a pMV261-derived *E coli-Mycobacteria* shuttle plasmid, to create pJH506 in which UFS and DFS flanked a green fluorescent protein gene (GFPuv, Clonetech) whose expression was driven by the *M. leprae* promoter 18 Kd. The UFS-gfp-DFS cassette was sub-cloned into the EcoRV site of plasmid pYUB657 to create pJH508. The first homologous recombination involved the identification of hygromycin resistant colonies, resulting from the transformation of *M. tuberculosis* with pJH508. Southern analysis of the NcoI digested DNA isolated from hygromycin resistant colonies probed with UFS or DFS, confirmed the presence of a single copy of pJH508 inserted into the *M. tuberculosis* genome. The transformant identified was then grown in 7H9 broth to saturation, to allow the second homologous recombination to occur, resulting in recombinants that could be selected by plating the culture on 7H10 plates, supplemented with 3% sucrose. Both Southern analysis and PCR of the DNA isolated from sucrose resistant colonies confirmed the RD1 deletion.

Specialized transduction (Bardarov and Jacobs, 1999), a mycobacteriophage-based method for the delivery of homologous DNA constructs using conditionally replicating shuttle phasmids (Jacobs et al, 1987; Bardarov and Jacobs, 1999; Carriere et al., 1997), has been used successfully for *M. tuberculosis* (Glickman et al., 2000; Glickman et al., 2001; Raman et al., 2001). Specifically, a transducing phage phAEKO1 was constructed by inserting UFS and DFS into pJSC347, flanking a hygromycin cassette, to create pJH313. pJH313 was digested with PacI and ligated to phAE159, a temperature sensitive mycobacteriophage derived from TM4. The transduction was performed by growing *M. tuberculosis* to an O.D.$_{600}$ of 0.8, washing twice with MP buffer, re-suspending into an equal volume of MP buffer and mixing with the transducing phage phAEKO1 at an MOI of 10. The mixtures were incubated at 37° C. overnight, then plated on 7H10 plates supplemented with hygromycin at 50 µg/ml. Hygromycin resistant colonies were analyzed by PCR and Southern hybridization, as described above, to confirm the deletion of RD1.

Complementation analyses was performed using the integration proficient cosmids (Pascopella et al., 1994; Lee et al., 1991) pYUB412 made by S. Bardarov, a library made by F. Bange, and cosmid identified and generously provided by S. T. Cole.

Results

Genetic engineering of *M. tuberculosis* mutants with RD1 deletions. The RD1 (region of difference) region has been defined as the specific 9454 bp of DNA that is present in virulent *M. tuberculosis* and *M. bovis*, but absent in BCG (Mahairas et al., 1996). The annotation of RD1 predicts that the deletion would disrupt 9 genes encoding ORF s (Id.; Cole et al., 1998). Five of the 9 ORF s have no known functions (Rv3871, Rv3876, Rv3877, Rv3878 and Rv3879c), two genes encode members of the PE/PPE family (Rv3872/Rv3873), and two genes encode the secreted proteins Cfp10 (Berhet et al., 1998) and Esat6 (Andersen et al., 1991) (Rv3875) (FIG. 1). To test if the RD1 region is essential for virulence in *M. tuberculosis*, it was necessary to 1) delete the RD1 region from virulent *M. tuberculosis* strains, 2) demonstrate loss of virulence and 3) restore virulence by complementation with the RD1 DNA. The RD1 deletion (ΔRD1) was successfully introduced into *M. tuberculosis* by two different techniques, utilizing both a plasmid that allows two-step sequential recombination to make an unmarked deletion, and specialized transduction (FIG. 1a-c). For both methods, the same 1200 bp on each side of the RD1 deletion were cloned into the appropriate plasmid or phage vector and then introduced into *M. tuberculosis* H37Rv by transformation or phage infection. An unmarked RD1 deletion mutant of *M tuberculosis* H37Rv, mc²4004, was constructed, purified, and has the advantage that additional mutations can be readily added to it. In addition, the RD1 deletion was successfully engineered in the H37Rv and Erdman strains of *M. tuberculosis* using a specialized transducing phage. Since TM4 phages have been shown to infect over 500 clinical *M. tuberculosis* isolates (Jacobs et al., 1987), it should be possible to introduce the RD1 deletion into any *M. tuberculosis* isolate of interest.

*M. tuberculosis* H37Rv ΔRD1 is attenuated for virulence. To test if the RD1 deletion causes an attenuating phenotype in *M. tuberculosis*, the *M. tuberculosis* H37Rv ΔRD1 (mc²4004) was introduced into immunocompromised mice possessing the SCID (severe combined immunodeficiency) mutation. Groups of ten mice were injected intravenously with either 2×10⁶ *M. tuberculosis* H37Rv or *M. tuberculosis* H37Rv ΔRD1 and three mice per group were sacrificed 24 hours later to verify the inoculation doses. All of the SCID mice infected with the parental *M. tuberculosis* H37Rv strain died within 14 to 17 days post infection (FIG. 2a). In contrast, the SCID mice infected with the same dose of *M. tuberculosis* H37Rv ΔRD1 were all alive at 35 days post-infection demonstrating a marked attenuation of the strain. To prove that the attenuation was due to the RD1 deletion, mc²4004 was transformed with an integrating plasmid containing the RD1 region from *M. tuberculosis* H37Rv. SCID mice injected intravenously with 2×10⁶ of the transformed strain died 13 to 16 days post-infection (FIG. 2a), thereby, establishing that the genes in the RD1 deletion complemented the attenuating phenotype.

Figure 2B:
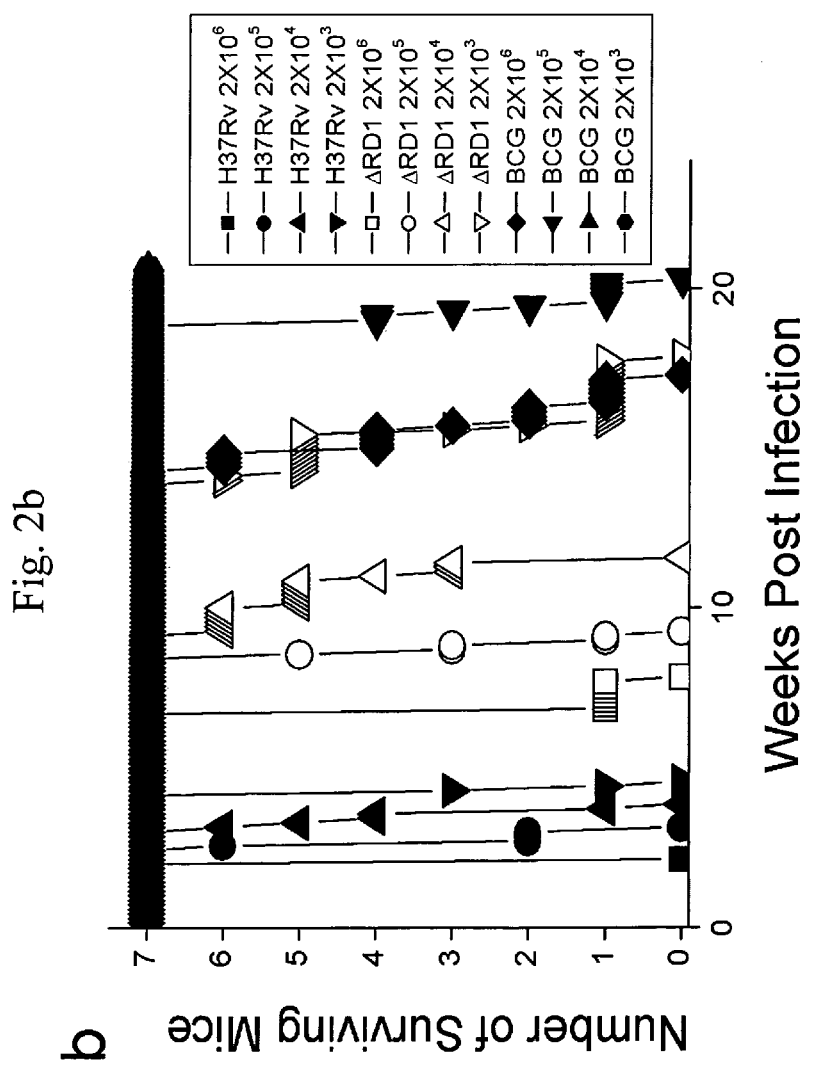

To further characterize the attenuating phenotype of the RD1 deletion in mc²4004, we compared the virulence of M. tuberculosis H37Rv and BCG-Pasteur to M. tuberculosis H37Rv ΔRD1 with time-to-death experiments in SCID mice following injections with 10-fold varying inocula. Groups of 10 mice were injected intravenously, each mouse receiving from $2\times10^3$ to $2\times10^6$ CFU. FIG. 2b shows that the SCID mice succumbed to the infection with all three mycobacterial strains. However, the SCID mice succumbed to an M. tuberculosis H37Rv intravenous infection within 2 to 5 weeks, in a dose dependent manner. In the same time frame, the SCID mice did not succumb to infection with M. tuberculosis H37Rv ΔRD1 until week 7, and only then, with the high dose of $2\times10^6$ CFU. Mice receiving $2\times10^3$ CFU M. tuberculosis H37Rv ΔRD1 survived longer than 14 weeks post infection, the survival rate of which coincided with the mice receiving $2\times10^6$ CFU of M. bovis BCG. Thus, these experiments established that M. tuberculosis H37Rv ΔRD1 was significantly more attenuated than its parent, but not as attenuated as BCG-Pasteur in the immunocompromised mice.

Figure 3:
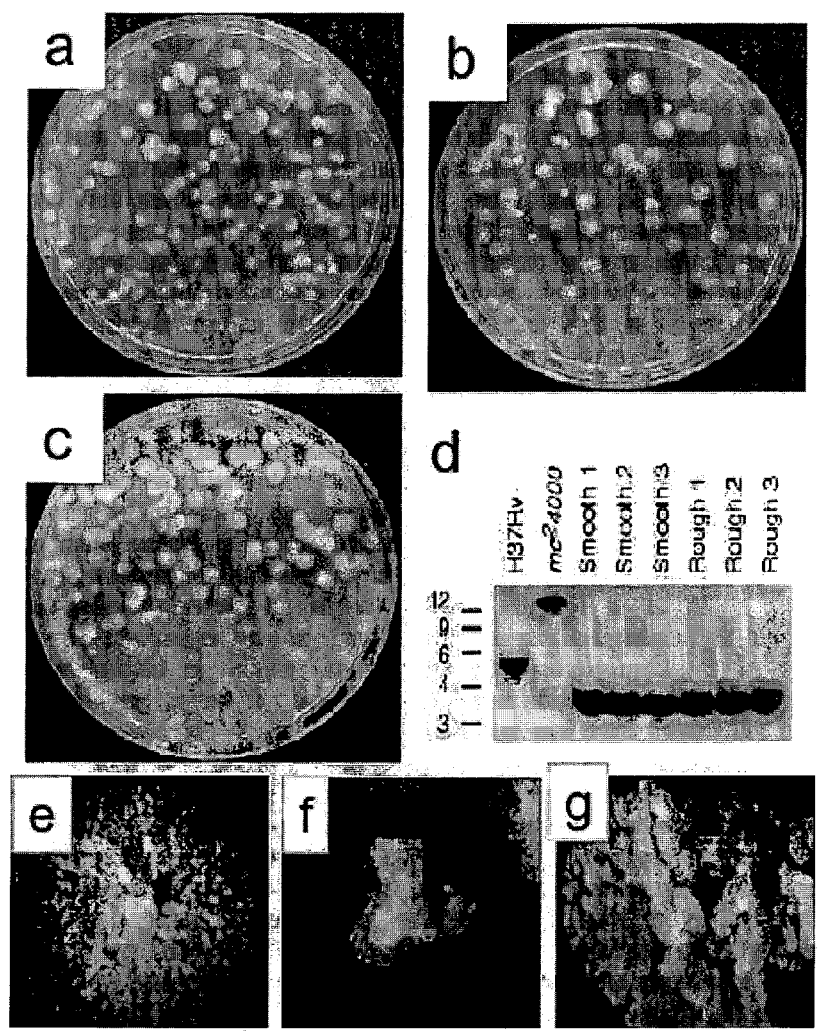

Colonial morphotypes of M. tuberculosis H37Rv ΔRD1. The M. tuberculosis H37Rv ΔRD1 mutant was generated independently three times from the single crossover construct (mc²4000) and upon subculturing, consistently yielded a 20 to 50% mixture of two colonial morphotypes on Middlebrook medium without Tween 80 (FIG. 3a). One morphotype was a smooth (S) phenotype that was flat and corded (like the parental M. tuberculosis H37Rv strain) and the second was a rough and raised (R) phenotype. Repeated subculturing of either the R or S colonies continued to yield both colonial morphotypes, but with a distribution of approximately 80% smooth and 20% rough colonies. The distinction of these two types of morphology could be noted even when the colonies were less than two weeks old as the rough colonies were constricted and elevated with only a small portion of the base of the colony attached to the agar, while the smooth colonies tends to be flattened and spread out. When colonies grew older, e.g. 6 weeks old, the rough colonies remained more constricted compared to those of smooth colonies. The rough colonies exhibited large folds on the surface (FIG. 3f, g), as compared to those of the smooth colonies that exhibited small wrinkles (FIG. 3e).

Interestingly, in 1929, Petroff et al. reported a similar property for an early-derived BCG strain (Petroff et al., 1929) and proposed that the attenuation phenotype of BCG was not stable. Calmette disputed that the avirulent phenotype reverted and postulated that Petroff et al. had acquired a contaminating virulent strain. Southern analysis of R and S colonies revealed each morphotype has the same RD1-deleted genotype (FIG. 3d). Furthermore, complementation of M. tuberculosis H37Rv ΔRD1 with the RD1 region restored the mutant phenotype back to the homogenous parental S phenotype (FIG. 3a-c). These results suggest that the variable morphotypes resulted directly from the RD1 deletion thus dissociating a direct correlation of virulence with morphotype.

Figure 4:
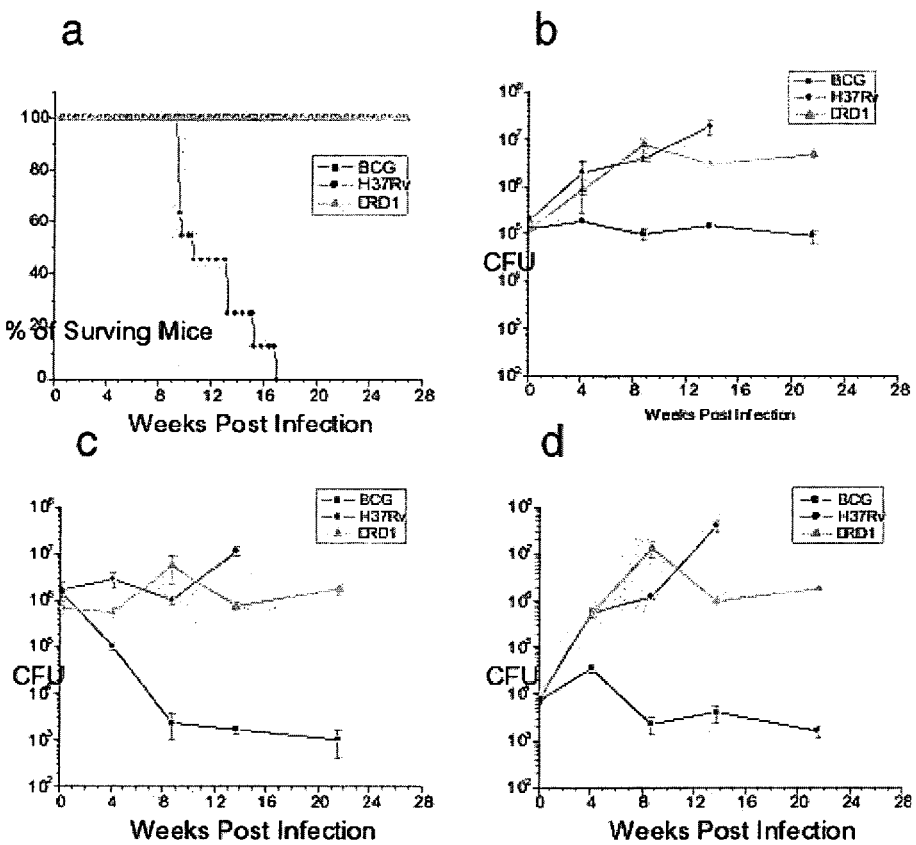

The M. tuberculosis H37Rv ΔRD1 is highly attenuated in immunocompetent BALB/c mice. To further assess the pathogenicity, survival, growth kinetics, and the histopathological analysis of the M. tuberculosis H37Rv ΔRD1 mutant, we compared the parental M. tuberculosis H37Rv to BCG-Pasteur strains in BALB/c mice. In survival studies, greater than 50% BALB/c mice had died at 14 weeks post i.v. infection with $2\times10^6$ CFUs of M. tuberculosis H37Rv strain (FIG. 4a). In contrast, all mice infected with a similar dose of either BCG or M. tuberculosis H37Rv ΔRD1 survived for longer than 22 weeks. These results were substantiated in a separate experiment in which a group of 11 BALB/c mice were infected with $1\times10^5$ CFU of M. tuberculosis H37Rv ΔRD1 and 9 of 11 mice (81%) survived greater than 9 months post-infection (data not shown). While BCG and M. tuberculosis H37Rv ΔRD1 showed similar survival results, the growth relative kinetics in mouse organs differed substantially. BCG grew in a limited fashion in lungs, liver and spleen in BALB/c mice and was cleared to undetectable levels by week 12 (FIG. 4b-d). In contrast, the M. tuberculosis H37Rv ΔRD1 strain grew in a fashion indistinguishable from the parental M. tuberculosis H37Rv in all mouse organs for the first 8 weeks. Thereafter, mice infected with the parental M. tuberculosis failed to contain the infection leading to mortality. Strikingly, mice infected with the M. tuberculosis H37Rv ΔRD1 showed a definite control over infection resulting in significantly prolonged survival of mice (FIG. 4b-d).

Figure 5:
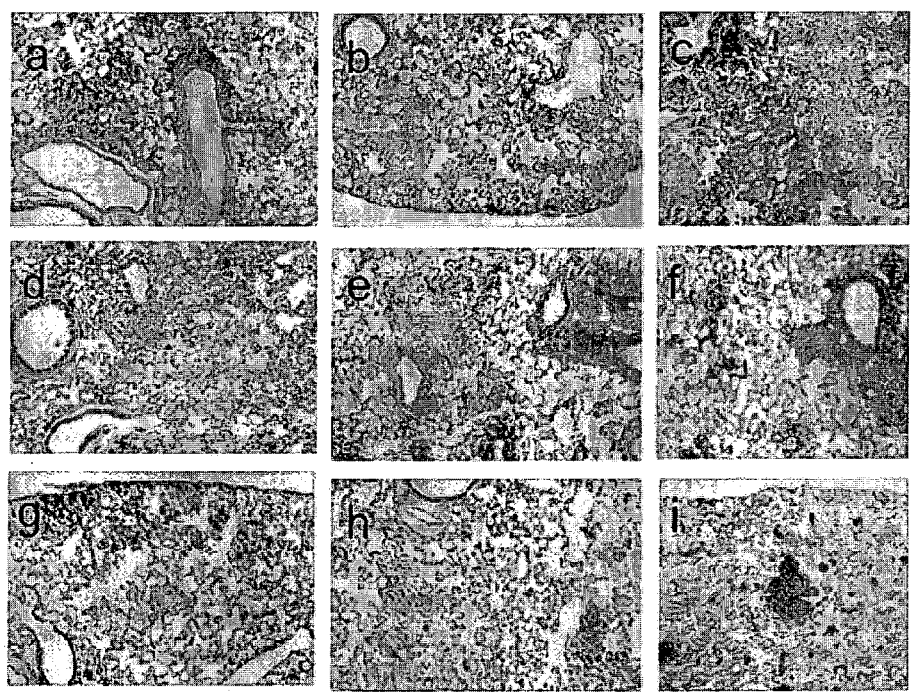

The differing survival data of the three strains was clearly substantiated by histopathological analysis. M. tuberculosis H37Rv ΔRD1 caused less severe organ damage in the lung, liver and spleen than the highly virulent parent strain M. tuberculosis H37Rv. M. bovis BCG was the least virulent of the three strains. Based on histopathological evaluation, the mortality in mice infected with the wild type M. tuberculosis H37Rv (documented above and in FIG. 4a) was caused by worsening pneumonia, hepatitis and splenitis (FIG. 5a-c). Mice examined at 14 weeks post-infection had developed severe lobar granulomatous pneumonia. Acid fast staining demonstrated large numbers of M. tuberculosis H37Rv, often in clumps, throughout the lung. The livers and spleens showed a severe diffuse granulomatous inflammation.

Histopathological examination further demonstrated that M. tuberculosis H37Rv ΔRD1 was attenuated in virulence compared to the parent strain M. tuberculosis H37Rv (FIG. 5d-f). In contrast to the rapidly progressive infection with the parent strain M. tuberculosis H37Rv, the lung lesions caused by M. tuberculosis H37Rv ΔRD1 were maximal in mice examined at 8 weeks post-infection. Consolidating granulomatous pneumonia involved an estimated 25-30% of the lung in these mice. Numerous organisms were demonstrated by acid fast staining. The pneumonia subsequently underwent partial resolution. By 14 weeks, and again at 22 weeks post-infection, the lungs showed peribronchial and perivascular inflammatory cell accumulations and focal, generally non-confluent, granulomas now with a prominent lymphocytic infiltration. The numbers of acid-fast organisms were reduced. Liver lesions consisted of low numbers of scattered granulomas. Spleens were smaller, with persistent granulomas in the red pulp.

Mice infected with M. bovis BCG showed mild lesions in the lung, liver and spleen at all time points (FIG. 5g-i). At longer time intervals post-infection the lesions were fewer in number, smaller with prominent lymphocytic infiltrations. At 14 weeks post-infection, M bovis BCG was below the level of detection by acid fast staining. In summary, whereas M tuberculosis H37Rv ΔRD1 initially grew in a manner similar to the parental M. tuberculosis H37Rv, this RD1 mutant was limited in the extent of spread of infection, particularly in the lung. This contrasted to the extensive and severe damage caused by the parent strain. The subsequent resolving granulomas, localization of the lesions and changes in the composition of the inflammatory cell infiltrations suggested that the mice mounted an effective immune response to combat M. tuberculosis H37Rv ΔRD1 infection and thereby reduced the numbers of viable organisms.

*M. tuberculosis* H37Rv ΔRD1 protects mice against aerosolized *M. tuberculosis* challenge. To test the potential of *M. tuberculosis* H37Rv ΔRD1 to immunize mice and protect against tuberculous challenge, we used the model of subcutaneous immunization followed by aerosol challenge with virulent *M. tuberculosis*. Our initial studies in C57BL/6 mice monitored the growth the *M. tuberculosis* H37Rv ΔRD1 strain over an 84-day period. Groups of mice (5 mice per group) were vaccinated subcutaneously (sc) either once or twice, 6 weeks apart, with $10^6$ CFU *M. tuberculosis* H37Rv ΔRD1 organisms. Additional mice were infected intravenously (iv) with the same dose of the RD1-deleted strain in order to examine the pathogenicity in C57BL/6 mice.

As seen in Table 1, *M. tuberculosis* H37Rv ΔRD1 persisted in the lungs, liver, and spleen for 3 months at moderate levels of infection but the organisms failed to grow substantially in the lungs and spleens of mice that had been inoculated iv. In contrast, reduced persistence and decreased concentrations of *M. tuberculosis* H37Rv ΔRD1 organisms were detected in organ homogenates prepared from mice that had been vaccinated sc. For the groups of mice that had been immunized with only one dose sc., low levels of *M. tuberculosis* H37Rv ΔRD1 bacilli were recovered from the spleen after 28 and 56 days post-vaccination; however, no splenic mycobacteria were detected 84 days after the sc. injection. Importantly, the concentration of *M. tuberculosis* H37Rv ΔRD1 organisms in the lungs after the sc. immunizations was below the threshold of detection (<100 CFUs per organ) for the CFU assay at nearly all time points during the three-month study.

TABLE 1

Growth kinetics in C57BL/6 mice.

| Weeks | Lung (Log CFU) | | | Spleen (Log CFU) | | |
|---|---|---|---|---|---|---|
| | i.v. | s.c. | s.c. (2X) | i.v. | s.c. | s.c. (2X) |
| 4 | 5.86 ± 0.10 | <2 | not done | 5.73 ± 0.05 | 2.41 ± 0.26 | not done |
| 8 | 5.79 ± 0.07 | <2 | 2.52 ± 0.34 | 5.37 ± 0.04 | 3.12 ± 0.40 | 3.62 ± 0.29 |
| 12 | 5.61 ± 0.09 | <2 | <2 | 5.40 ± 0.05 | <2 | 3.52 ± 0.22 |

Mice were infected with $10^6$ *M. tuberculosis* H73Rv ΔRD1 by different routes. The data are presented as mean ± standard error of the mean.

Three months after the sc. vaccinations with the ΔRD1 strain, groups of mice were challenged aerogenically with a low dose (50 CFUs) of an acriflavin-resistant strain of *M. tuberculosis* Erdman. The use of a drug-resistant challenge strain permitted the differentiation of the challenge organisms from the sensitive vaccine population. As controls, other groups of mice were immunized sc. with $10^6$ CFUs of BCG Pasteur. The protective responses induced by the *M tuberculosis* H37Rv ΔRD1 vaccination were evaluated by assessing the relative growth of the acriflavin-resistant challenge organisms in naïve, BCG vaccinated, and *M. tuberculosis* H37Rv ΔRD1 immunized mice and by comparing the relative post-challenge lung pathology in the experimental groups and the naive controls. As seen in Table 2, the growth of the drug-resistant challenge organisms was substantially lower in the lungs of animals vaccinated with BCG or the *M. tuberculosis* H37Rv ΔRD1 vaccine. Significant reductions in the lung CFU values in the vaccinated animals (relative to naive controls) could be detected both 28 and 56 days after the challenge. Dissemination to the spleen was also significantly limited in all of the vaccination groups with the most substantial differences (−1.4 $\log_{10}$ CFUs compared to the naives) being detected during the first month post-challenge. While significant differences in the growth of the mycobacterial challenge was identified between unvaccinated and vaccinated mice, the rate of proliferation of the acriflavin-resistant challenge strain in all the experimental groups (BCG sc or *M. tuberculosis* H37Rv ΔRD1 1 or 2 doses sc) was nearly identical and not statistically different.

TABLE 2

*M. tuberculosis* ΔRD1 and BCG protect C57BL/6 mice from areosol challenge with *M. tuberculosis* Erdman

| | Lung (Log CFU) | | Spleen (Log CFU) | |
|---|---|---|---|---|
| | Day 28 | Day 56 | Day 28 | Day 56 |
| Naive | 4.77 ± 0.06 | 4.11 ± 0.05 | 3.57 ± 0.21 | 3.20 ± 0.16 |
| BCG (1X) | 3.96 ± 0.20 | 3.80 ± 0.08 | 2.18 ± 0.18 | 2.48 ± 0.23 |
| ΔRD1 (1X) | 3.97 ± 0.39 | 3.71 ± 0.06 | 2.12 ± 0.12 | 2.60 ± 0.25 |
| ΔRD1 (2X) | 3.96 ± 0.15 | 3.66 ± 0.09 | 2.21 ± 0.15 | 2.22 ± 0.16 |

Immunizations were performed subcutaneously once (1X) or twice (2X) with 2 × $10^6$ CFUs of the vaccinating strains. Three months later, vaccinated animals were aerogenically challenged with 50 CFUs/mouse of acriflavin resistant *M. tuberculosis* Erdman. The growth of the bacterial challenge was monitored 28 and 56 days post infection by plating on Middlebrook 7H11 plates containing 20 μg/ml acriflavin and using procedures previously described (Delogu et al., 2002).

Discussion

The *M. tuberculosis* H37Rv ΔRD1 mutant strain shares significant properties with BCG including: 1) a significant attenuation of virulence in mice, 2) the ability to generate variable colonial morphotypes, and 3) the ability to protect mice against aerogenic tuberculosis challenge. These properties, and the observation that RD1 is the only deletion common to all BCG substrains, makes it likely that the RD1 deletion is the primary attenuating mutation. It remains to be determined if a single gene or a number of genes in this region causes the attenuated phenotype. The variable colonial morphotype switch does suggest that a protein regulating cell wall biogenesis is affected. Notably, defined mutations affecting the cyclopropanation of mycolic acids (Glickman et al., 2000) or the synthesis or export of phthiocerol dimycoseroate (Cox et al., 1999) have been found to correlate with decreased virulence and altered colony morphotypes in *M. tuberculosis* and thus represent attractive candidate genes that might be regulated by an RD1-encoded gene. The *M. tuberculosis* ΔRD1 mutant provides a precisely defined background strain by which to determine virulence and colony morphology related genes.

BCG is currently the only antituberculous vaccine available for use in humans. In many animal models, BCG has been shown to induce protective immunity against *M. tuberculosis* challenge (Opie and Freund, 1937; Hubbard et al., 1992; Baldwin et al., 1998) and in addition, has demonstrated protection against the most severe and fatal form of TB in children (Rodrigues et al., 1991). However, BCG has shown variable efficacy in protecting adults from pulmonary TB (Tuberculosis Prevention Trial, 1980; Hart and Sutherland, 1977; Bloom and Fine, 1994). Due to the uncertain efficacy of BCG, particularly in TB-endemic countries, the development of improved tuberculosis vaccines has become an international research priority.

Our challenge studies have demonstrated that the protective immune responses elicited by immunization with *M. tuberculosis* H37Rv ΔRD1 in mice are at least as strong as the protective responses induced by vaccination with BCG. The *M. tuberculosis* H37Rv ΔRD1 mutant also retains the BCG-associated property of limited spread to the lung following subcutaneous immunization. Restricted dissemination of the ΔRD1 mutant to the lung suggests it should have a favorable overall safety profile. Also, the unmarked mutant of *M. tuber-* culosis H37Rv ΔRD1 provides a single deletion strain whereby other attenuating mutations can be readily engineered. Since the risk of reversion to wild-type virulence decreases substantially with each additional attenuating mutation, *M. tuberculosis* mutants harboring deletions in two or three separate genetic loci should provide a much safer vaccine for long term use.

*M. tuberculosis* mutants with RD1 deletions represent attractive candidates as novel vaccines for TB prevention. These mutants, derived from a single mutagenic event from the parental *M. tuberculosis* strain, replicate more efficiently in vivo than BCG, especially early in infection. This enhanced rate of proliferation for the RD1-deleted strains, relative to BCG, may lead to the induction of increased protective immunity in humans, after vaccination with *M. tuberculosis* H37Rv ΔRD1. Moreover, they could also be more immunogenic as there exist at least 129 ORFs present in *M. tuberculosis* H37Rv that are absent from *M. bovis* (Behr et al., 1999). Since some of these ORFs are likely to encode regulatory proteins affecting the expression of other genes, there could be hundreds of antigens expressed in *M. tuberculosis*-infected cells that are absent from BCG-infected cells. Thus, RD1 deletion mutants constructed from human tubercle bacilli could protect humans against disease substantially better than BCG.

EXAMPLE 2

Vitamin Auxotrophs of *Mycobacterium Tuberculosis* are Attenuated and Protect Against Tuberculosis This example describes experimental methods and results that establish that deleting genes that control vitamin production in a virulent *M. tuberculosis* causes the *M. tuberculosis* to become avirulent and sustain an infection in mammals, and protect the mammal against challenge with a virulent *M. tuberculosis*.

Given the importance of NAD and nicotinamide (vitamin B3) and pantothenate (vitamin B5) as cofactors involved in carbon utilization, energy transduction (Abiko, 1975; Jackowski, 1996) and the biosynthesis of the complex lipid cell wall of *M. tuberculosis*, we hypothesized that mutations in the biosynthetic pathways for NAD and pantothenate could lead to the generation of mutant strains that retain a limited ability to replicate and subsequently get cleared within the host tissues. In *M. tuberculosis*, the nadABC operon controls the de novo biosynthesis of NAD. Similarly, the panC and panD genes that are organized in an operon control the rate-limiting step in the de novo biosynthesis of pantothenate. We constructed deletion mutants of *M. tuberculosis* in the nadBC and panCD genes using specialized transduction, as described in Example 1. The mutant strains mc$^2$3122 (ΔnadBC) and mc$^2$6001 (ΔpanCD) were auxotrophic for nicotinamide and pantothenate respectively. The in vitro reversion frequencies of the respective mutations were found to be less than $10^{-10}$ events per generation.

Figure 6:
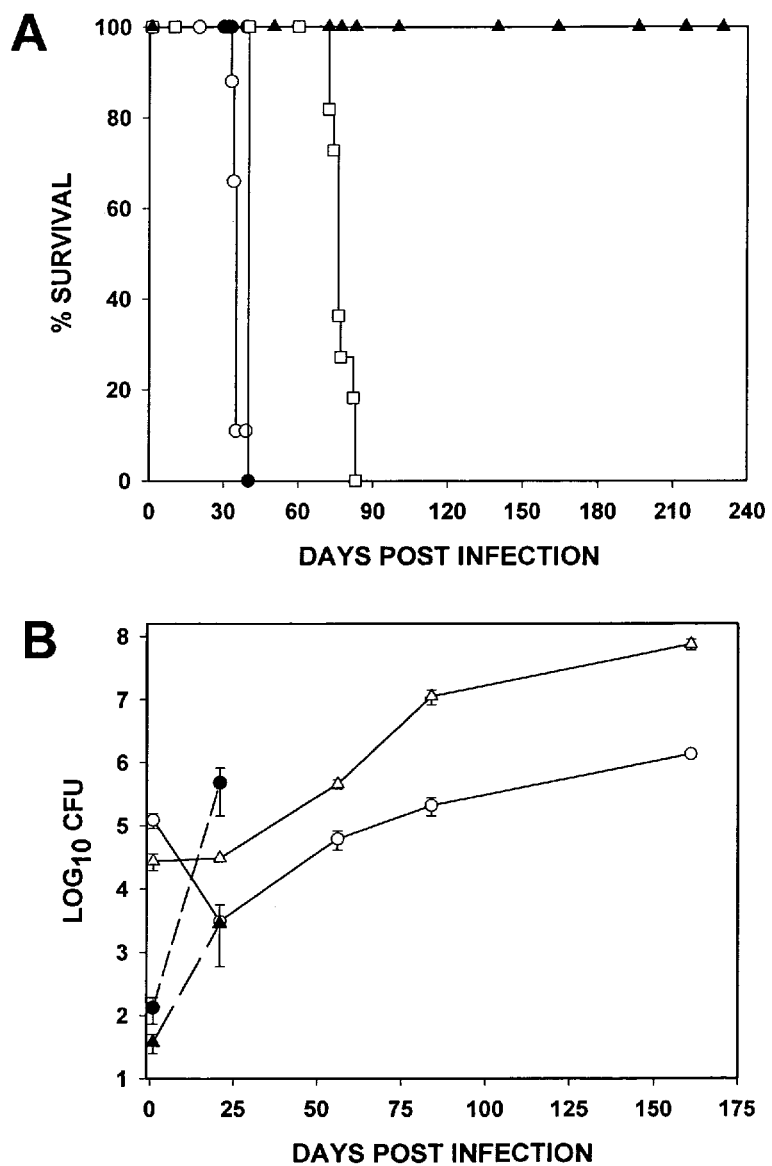

The safety and attenuation of ΔnadBC and ΔpanCD auxotrophic mutants were assessed by infection of immune-compromised SCID mice. SCID mice infected with wild-type *M. tuberculosis* and the ΔnadBC mutant succumbed to infection in about 5 weeks (data not shown). This result clearly indicates that in the absence of T-cell immunity, intermediates of NAD biosynthetic pathway, such as nicotinamide, are readily available in the macrophages to support the growth of the ΔnadBC mutant. In contrast all mice infected with the ΔpanCD mutant survived longer than 30 weeks, demonstrating the severe attenuation of this mutant strain. The full virulence phenotype was restored when the panCD wild type alleles were integrated into the chromosome of the ΔpanCD mutant in single copy, suggesting the observed attenuation in ΔpanCD to be due to the requirement of pantothenate for growth and not due to polar effects of the mutation on downstream genes. SCID mice infected with the same dose of conventional BCG-Pasteur vaccine strain succumbed to infection within 80 days (FIG. 6A) in accordance with earlier reports (Guleria, 1996). Enumeration of bacterial burdens in SCID mice infected with wild type *M. tuberculosis* H37Rv and the complementing strain (panCD in single copy integrated into the chromosome) showed a rapid increase in bacterial numbers in spleen, liver and lung before they succumbed to infection. In contrast, mice infected with ΔpanCD mutant, showed an initial drop in bacterial numbers in spleen and liver followed by a steady increase to reach $10^8$ in the lungs at 160 days, at which time all mice were still alive (FIG. 6B).

Figure 7:
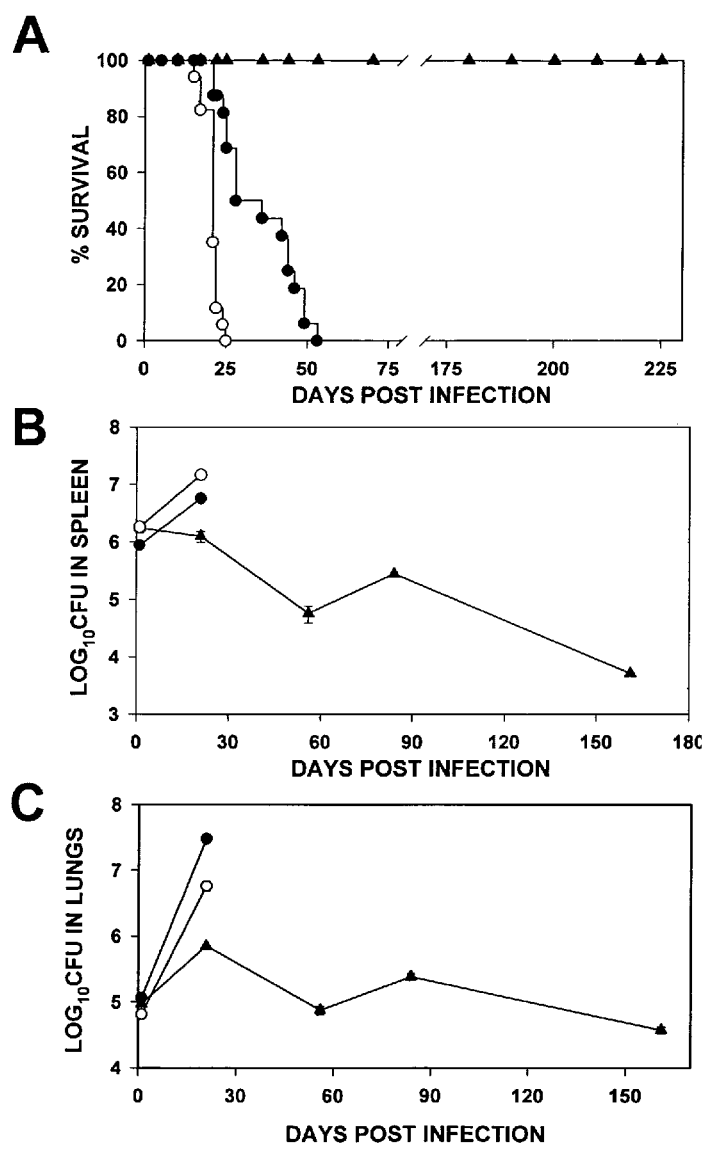

Having demonstrated the significant attenuation of ΔpanCD mutant, we sought to address the in vivo growth characteristics of this mutant in immune-competent BALB/c mice. All BALB/c mice infected with H37Rv succumbed to infection by day 25 with a MST of 22 days. Similarly, mice infected with the panCD-complemented strain were highly virulent with 100% mortality between 3-8 weeks post-infection similar to the wild type strain, with a MST of 28 days. In contrast, all mice infected with ΔpanCD mutant survived for over 33 weeks demonstrating the severe attenuation phenotype of this mutant in immune-competent mice (FIG. 7A). Interestingly, bacterial enumeration at three weeks post infection showed 1 log increase in the ΔpanCD numbers in lungs followed by a state of persistence with the onset of adaptive immune response. This growth characteristic was observed only in the lung but not in spleen or liver (FIG. 7B,C). A desirable trait of an effective live attenuated vaccine strain is its ability to grow within the host in a limited fashion in order to produce in vivo all the important protective antigens (McKenney, 1999; McKenny, 2000; Kanai, 1955). The ΔpanCD mutant exhibits this characteristic in the lung, which is the primary site of infection in humans and does not get cleared over a prolonged period in all the three organs. The earlier auxotrophs of *M. tuberculosis* failed to grow in any of the organs and hence failed to adequately protect against experimental challenge in guinea pigs (Jackson, 1999), or mice.

The ability of the ΔpanCD mutant to exhibit limited growth in the lung until the onset of adaptive immune response suggests that an unidentified putative pantothenate permease is able to transport this nutrient into resting macrophages, as in the SCID mice. A sodium-dependent pantothenate permease actively transports pantothenate into the cell of *Escherichia coli* (Vallari and Rock, 1985; Jackowski and Alix, 1990), *Plasmodium falciparum* (Saliba and Kirk, 2001) and mammals. Subsequent activation of macrophages leads to restricted supply of this nutrient within the phagosome resulting in growth arrest of the mutant. Pantothenic acid or its derivatives have been reported to confer resistance to radiation and oxidative stress by virtue of their role in biosynthesis of CoA and also by indirectly increasing the cellular supply of glutamate, a precursor of glutathione (Slyshenkov, 1995). Pantothenate kinase (PanK) mutants of *Drosophila* display membrane defects and improper mitosis and meiosis due to decreased phospholipid biosynthesis (Afshar et al., 2001). The disruption of de novo pantothenate biosynthesis causes an increased susceptibility of the ΔpanCD mutant to reactive oxygen and nitrogen intermediates that are released within activated macrophages.

Figure 8:
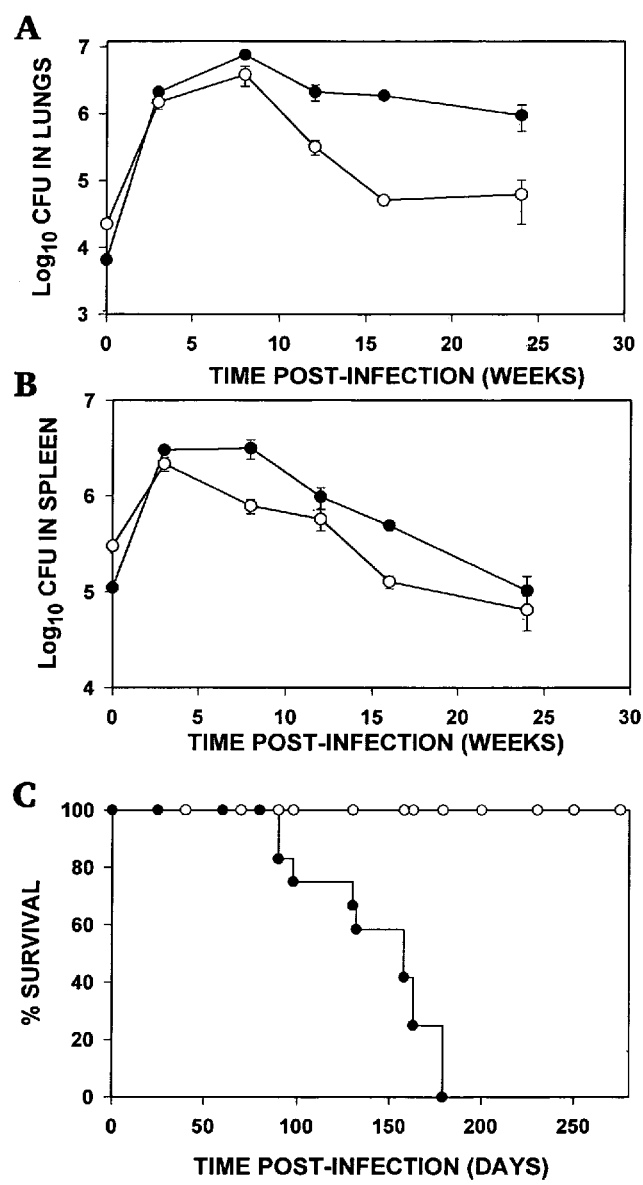

Having observed the ΔnadBC mutant to be non-attenuated in SCID mice, we chose to study the in vivo growth kinetics of this mutant in the more resistant C57BL/6 mice background. During the first three weeks of infection, the number of wild type and mutant bacteria recovered from all three organs showed little or no difference. Their numbers gradually increased in the lungs to reach $10^6$. However, with the onset of adaptive immune response at three weeks, when the growth of bacteria in the lungs of mice infected with H37Rv became constant and tightly controlled, bacterial load in the lungs of mice infected with ΔnadBC mutant showed a constant tendency for clearance to reach more than 1.5 log drop in the bacterial numbers compared to mice infected with wild type strain (FIG. 8A). This difference was preserved up to 24 weeks following infection.

The reduced ability of the ΔnadBC mutant to sustain an infection was accompanied by attenuated virulence clearly seen from the survival experiment (FIG. 8C). While all mice infected with the wild type strain succumbed to infection between day 90 and 179 (MST 116 days) all mice infected with the ΔnadBC mutant (n=12) remain alive for a period of more than 8 months (FIG. 8C).

Our observation of the attenuation phenotype of ΔnadBC mutant became obvious only after the onset of immune response, suggesting that once the macrophages become activated, they restrict the amount of available NAD or NAD intermediates causing a restricted growth of the mutant strain. This would be in agreement with the recently reported observations that a significant part of antimicrobial function of the macrophages could be attributed to the IFN-γ promoted enhanced expression of indolamine 2-oxygenase (IDO), the inducible enzyme controlling L-tryptophan catabolic pathway causing an almost complete depletion of L-tryptophan pool. The enhanced catabolism of L-tryptophan leads to increased de novo biosynthesis of NAD needed to protect the cells from the free radicals formed as a result of macrophage activation. Recently, several studies have demonstrated the involvement of the tryptophan catabolism in the antimicrobial mechanisms of the activated macrophages. Induction of IDO was found responsible for the inhibition of intracellular growth of *Toxoplasma, Leishmania, Legionella* and *Chlamydia*. The restricted intracellular growth of ΔnadBC mutant could be explained with the very little amount of free NAD or NAD intermediates available within the activated macrophages.

Having established the safety and persistence of ΔpanCD and ΔnadBC in immunocompetent mice, the protective efficacy of these mutants were evaluated using an aerosol challenge model with virulent *M. tuberculosis*, using the methods described in Example 1. The aerosol route of infection was chosen, as this is the natural route of infection in humans. To assess the capacity of the auxotrophic vaccines to restrict growth of virulent *M. tuberculosis* in the organs of infected mice, bacterial numbers were enumerated one month post-infection in lung and spleen. See Table 3. In the unimmunized controls, bacterial numbers rose rapidly in the spleen and lungs, in contrast mice infected with a single dose of ΔpanCD displayed significant reduction in bacterial numbers in the spleen and lung ($p<0.05$, in comparison to unimmunized controls). Mice given two doses of ΔpanCD displayed a statistically significant reduction in the bacterial numbers to 4.5 log units in the lung ($p<0.01$) and 3.7 log units in the spleen ($p<0.05$). Mice vaccinated with BCG showed comparable reduction in bacterial burden in the lung and spleen to 3.3 log units and 4.7 log units respectively ($p<0.01$). Mice immunized with one or two doses of ΔnadBC mutant conferred statistically significant protection ($p<0.01$ in comparison to unimmunized group) that is comparable to the protection afforded by BCG vaccination. Interestingly, mice immunized with the ΔnadBC mutant showed no detectable CFUs in the spleen suggesting that the vaccination completely prevented the hematogenous spread of wild type *M. tuberculosis* following aerosol challenge.

TABLE 3

| Experimental Group | Lung CFUs ($\log_{10}$) | Spleen CFUs ($\log_{10}$) |
|---|---|---|
| | A | |
| Naive | 4.05 ± 0.21 | 3.94 ± 0.21 |
| ΔnadBC (1 × sc) | 3.37 ± 0.40** | <2** |
| ΔnadBC (2 × sc) | 3.6 ± 0.35** | <2** |
| BCG (1 × sc) | 3.46 ± 0.19** | <2** |
| | B | |
| Naive | 5.56 ± 0.05 | 4.35 ± 0.21 |
| ΔpanCD (1 × sc) | 4.99 ± 0.17 (−0.57)* | 3.65 ± 0.15 (−0.70)* |
| ΔpanCD (2 × sc) | 4.55 ± 0.09 (−1.01)** | 3.73 ± 0.21 (−0.62)* |
| BCG (1 × sc) | 4.71 ± 0.21 (−0.85)** | 3.35 ± 0.20 (−1.00)** | p < 0.05 compared to naive,
**p < 0.01 compared to naive

Table 3. The attenuated *M. tuberculosis* ΔnadBC and ΔpanCD mutants protect against aerogenic challenge with *M. tuberculosis* Erdman. Groups of C57BL/6 mice (5 mice per group) were vaccinated subcutaneously either once or twice (6 weeks apart) with $10^6$ CFUs of mutant strains. Control mice were vaccinated subcutaneously with $10^6$ CFUs of BCG-Pasteur. Three months after the initial immunization with either ΔnadBC or ΔpanCD mutant or BCG, the mice were aerogenically challenged with approximately 100 CFUs of acriflavin-resistant *M. tuberculosis* Erdman ($Ac^rMTB$) strain as described earlier (Collins, 1985). After 28 days, the challenged mice were sacrificed, and the lungs and spleens of individual mice were removed aseptically and homogenized separately in 5 ml of Tween 80-saline using a Seward stomacher 80 blender (Tekmar, Cincinnati, Ohio). The homogenates were diluted serially in Tween 80 saline and plated on Middlebrook 7H11 agar with or without appropriate supplements as required. Samples from the BCG-vaccinated controls were plated on 7H11 agar containing 2 mg of thiophenecarboxylic acid hydrazide (Sigma Chemical Co., St Louis, Mo.) per ml to inhibit growth of any residual BCG. The CFU results were evaluated using the one-way ANOVA analysis of the Graph Pad InStat program. The numbers in paranthesis represent the differences between naive and vaccinated organ CFUs.

In order to test the ability of the auxotrophic mutants to confer long lasting immunity, mice were challenged 7 months after an initial subcutaneous immunization with the ΔnadBC mutant. See Table 4. Mice immunized with ΔnadBC displayed significantly reduced numbers of the challenge organism in the lungs and no detectable numbers in the spleen comparable to the numbers seen in the BCG vaccinated mice. The results suggest that the ΔnadBC vaccine strain is able to persist within the mouse organs sufficiently long to mount a long lasting immunity to control subsequent infection.

TABLE 4

| Experimental Group | Lung CFUs ($\log_{10}$) | Spleen CFUs ($\log_{10}$) |
|---|---|---|
| Naive | 4.61 ± 0.07 | 4.07 ± 0.20 |
| BCG | 4.00 ± 0.13* | 2 |
| NAD (1 × iv) | 3.28 ± 0.15** | <2 |
| NAD (2 × iv) | 2.95 ± 0.14** | <2 |

TABLE 4-continued

| Experimental Group | Lung CFUs (log$_{10}$) | Spleen CFUs (log$_{10}$) |
|---|---|---|
| NAD (1 × sc) | 4.05 ± 0.12* | <2 |
| NAD (2 × sc) | 3.94 ± 0.13* | <2 |

*P < 0.05;
**P < 0.01 by Dunnett's Multiple Comparison Test

Table 4. Immunizations with the ΔnadBC mutant confer long-term protection against an aerosol challenge. Groups of C57BL/6 mice (5 mice per group) were vaccinated subcutaneously or intravenously either once or twice (6 weeks apart) with 10$^6$ CFUs of ΔnadBC mutant. Control mice were vaccinated subcutaneously with 10$^6$ CFUs of BCG-Pasteur. Seven months after the initial immunization with either ΔnadBC mutant or BCG, the mice were aerogenically challenged with approximately 50 CFUs of acriflavin-resistant M. tuberculosis Erdman (Ac$^r$MTB) strain and the bacterial numbers at 28 days post challenge enumerated as described in Table 1.

To the best of our knowledge this is the first report of any M. tuberculosis auxotrophic vaccines administered subcutaneously to confer protection comparable to the conventional BCG vaccine strain in a mouse model of infection. Mice vaccinated with the ΔpanCD and ΔnadBC survived for over one year following the aerosol challenge indicating the protection and safety of these vaccine strains.

EXAMPLE 3

A Pantothenate Auxotroph of *Mycobacterium Tuberculosis* is Highly Attenuated and Protects Mice Against Tuberculosis This Example is published as Sambandamurthy et al., 2002.

Example Summary.

With the advent of HIV and the widespread emergence of drug resistant strains of *Mycobacterium tuberculosis*, newer control strategies in the form of a better vaccine could decrease the global incidence of tuberculosis. A desirable trait in an effective live attenuated vaccine strain is its ability to persist within the host in a limited fashion in order to produce important protective antigens in vivo (Kanai and Yanagisawa, 1955; McKenney et al., 1999). Rationally attenuated *M. tuberculosis* vaccine candidates have been constructed by deleting genes required for growth in mice (Jackson et al., 1999; Hondalus et al., 2000; Smith et al., 2001). These candidate vaccines failed to elicit adequate protective immunity in animal models, due to their inability to persist sufficiently long within the host tissues. Here we report that an auxotrophic mutant of *M. tuberculosis* defective in the de novo biosynthesis of pantothenic acid (vitamin B5) is highly attenuated in immunocompromised SCID mice and in immunocompetent BALB/c mice. SCID mice infected with the pantothenate auxotroph survived significantly longer than mice infected with either BCG vaccine or virulent *M. tuberculosis* (250 days, vs. 77 days, vs. 35 days). Subcutaneous immunization with this auxotroph conferred protection in C57BL/6J mice against an aerosol challenge with virulent *M. tuberculosis*, which was comparable to that afforded by BCG vaccination. Our findings highlight the importance of de novo pantothenate biosynthesis in limiting the intracellular survival and pathogenesis of *M. tuberculosis* without reducing its immunogenicity in vaccinated mice.

Materials and Methods

Media and Strains. *M. tuberculosis* H37Rv, *M. tuberculosis* Erdman and *M. bovis* BCG Pasteur were obtained from the Trudeau Culture Collection (Saranac Lake, N.Y.) and cultured in Middlebrook 7H9 broth and 7H11 agar supplemented with 10% OADC, 0.5% glycerol, and 0.05% Tween 80. When required, pantothenate (24 μg/ml), hygromycin (50 μg/ml) or kanamycin (25 μg/ml) was added. Stock strains were grown in Middlebrook 7H9 broth in roller bottles and harvested in mid-logarithmic growth phase, before being stored in 1 ml vials at −70° C. until required.

Disruption of panCD genes in *M. tuberculosis*. Specialized transduction was employed to disrupt the chromosomal copy of the panCD genes as described (U.S. Pat. No. 6,271,034). Briefly, the 823 bp region upstream to the panC gene was amplified using primers Pan1 (5'-GTGCAGCGCCATCTCTCA-3') (SEQ ID NO:9) and Pan2 (5'-GTTCACCGGGATGGAACG -3') (SEQ ID NQ:10). A 716 bp region downstream to the panD gene was amplified using primers Pan3 (5'-CCCGGCTCGGTGTGGGAT-3') (SEQ ID NO:11) and Pan4 (5'-GCGCGGTATGCCCGGTAG-3') (SEQ ID NO:12). PCR products were cloned with the TOPO TA cloning kit (Invitrogen, Calif.), and sequenced. PCR products were subsequently cloned into pJSC347, flanking a hygromycin cassette to create pSKV1. PacI digested pSKV1 was ligated into the temperature-sensitive mycobacteriophage phAE159 derived from TM4 and transduced as described earlier (Glickman et al., 2000; Raman et al., 2001). Genomic DNAS from hygromycin-resistant and pantothenate—requiring colonies were digested with BssHII, and probed with a 716 bp downstream region, flanking the *M. tuberculosis* panCD operon to confirm the deletion. For complementation, the *M. tuberculosis* panCD operon was amplified by PCR from genomic DNA with its putative promoter, cloned with TA cloning kit, sequenced, and subcloned into pMV306kan, a site-specific integrating mycobacterial vector.

Animal infections. C57BL/6, BALB/cJ and BALB/c SCID mice (6-8 weeks old) were purchased from Jackson Laboratories and were infected intravenously through the lateral tail vein. For time-to-death assays, BALB/c SCID mice were infected intravenously with $1\times10^2$ CFU of *M. tuberculosis* H37Rv, $1\times10^2$ CFU of panCD-complemented strain, $1\times10^5$ CFU of ΔpanCD mutant, or $1\times10^5$ CFU of *M. bovis* BCG-P. For mouse organ CFU assays, BALB/cJ mice were infected with $1\times10^6$ CFU of *M. tuberculosis* H37Rv or the panCD-complemented strain or the ΔpanCD mutant. At appropriate time points, groups of 4-5 mice were sacrificed and the selected organs were homogenized separately in PBS/0.05% Tween 80, and colonies were enumerated on 7H11 plates grown at 37° C. for 3-4 weeks (see McKinney et al., 2000). Pathological examination was performed on tissues fixed in 10% buffered formalin. The CFU results were evaluated using the one-way ANOVA analysis of the Graph Pad InStat program. All animals were maintained in accordance with protocols approved by the Albert Einstein College of Medicine Institutional Animal Care and Use Committee.

Vaccination Studies. Groups of C57BL/6 mice (5 mice per group) were vaccinated subcutaneously either once or twice (6 weeks apart) with $1\times10^6$ CFU of the ΔpanCD mutant strain. Control mice were vaccinated subcutaneously with $1\times10^6$ CFU of *M. bovis* BCG-P. Three months after the initial immunization with either the ΔpanCD mutant or BCG, the mice were aerogenically challenged with approximately 50-100 CFU of *M. tuberculosis* Erdman strain as described earlier. At 28 days following aerosol challenge, the challenged mice were sacrificed; the lungs and spleens of individual mice were removed aseptically and homogenized separately in 5 ml of Tween 80-saline using a Seward Stomacher 80 blender (Tekmar, Cincinnati, Ohio). The homogenates were diluted serially in Tween 80 saline and plated on Middlebrook 7H11 agar with or without appropriate supplements as required. Samples from the BCG-vaccinated controls were plated on 7H11 agar containing 2 mg/ml of thiophene-2-carboxylic acid hydrazide (Sigma) to inhibit growth of any residual BCG.

Results and Discussion.

Lipid biosynthesis and metabolism have been shown to play a pivotal role in the intracellular replication and persistence of *M. tuberculosis* (Cox et al., 1999; Camacho et al., 1999; Glickman et al., 2000; De Voss et al., 2000; Manca et al., 2001; McKinney et al., 2000). Therefore, we sought to globally impair the ability of this bacterium to synthesize lipids. Pantothenic acid (vitamin B5) is an essential molecule required for the synthesis of coenzyme A (CoA) and acyl carrier protein (ACP), that play important roles as acyl group carriers in fatty acid metabolism, the tricarboxylic acid cycle, biosynthesis of polyketides and several other reactions associated with intermediary metabolism (Jackowski, 1996). Bacteria, plants and fungi synthesize pantothenate from amino acid intermediates, whereas it is a nutritional requirement in higher animals (FIG. 9*a*).

Figure 9:
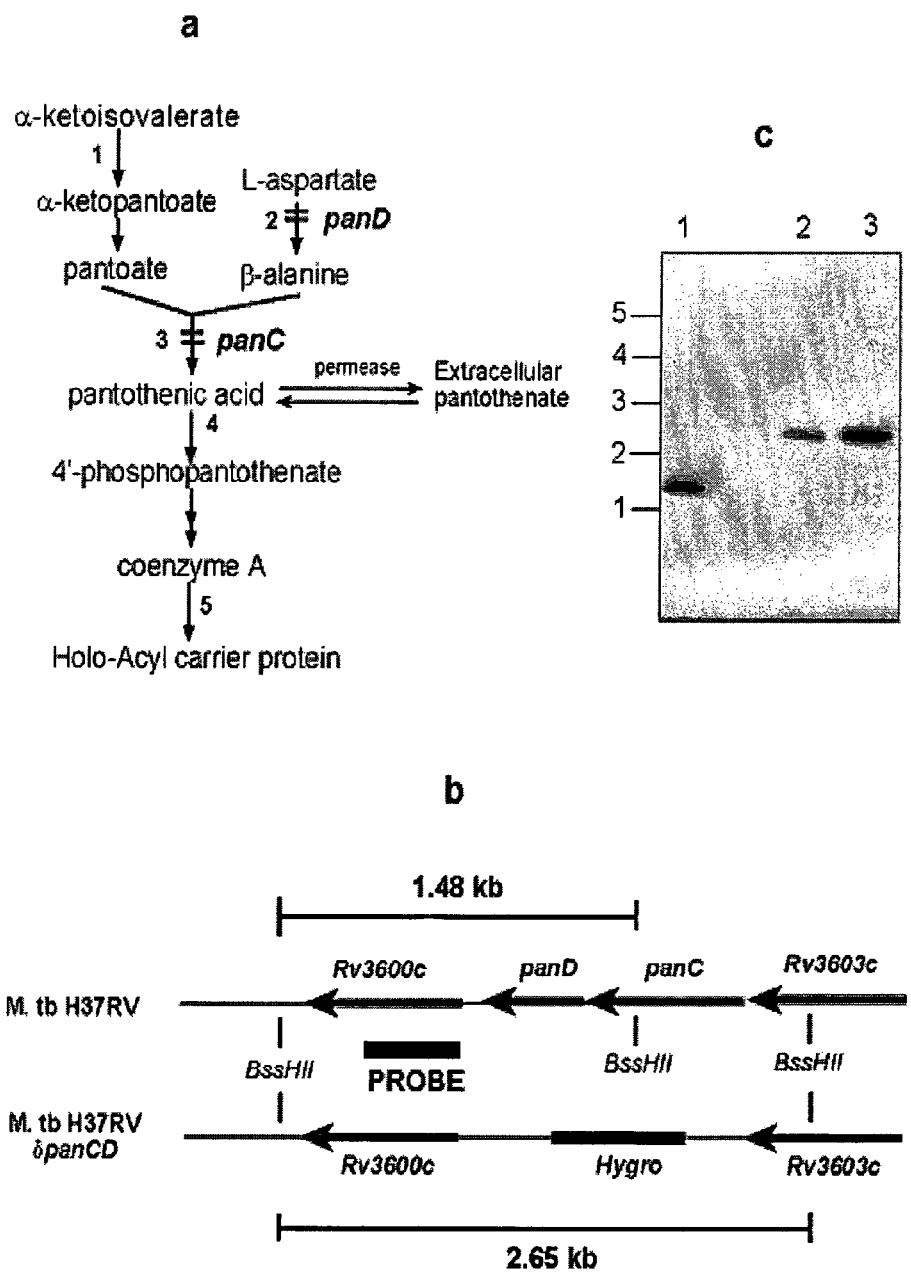
Figure 10:
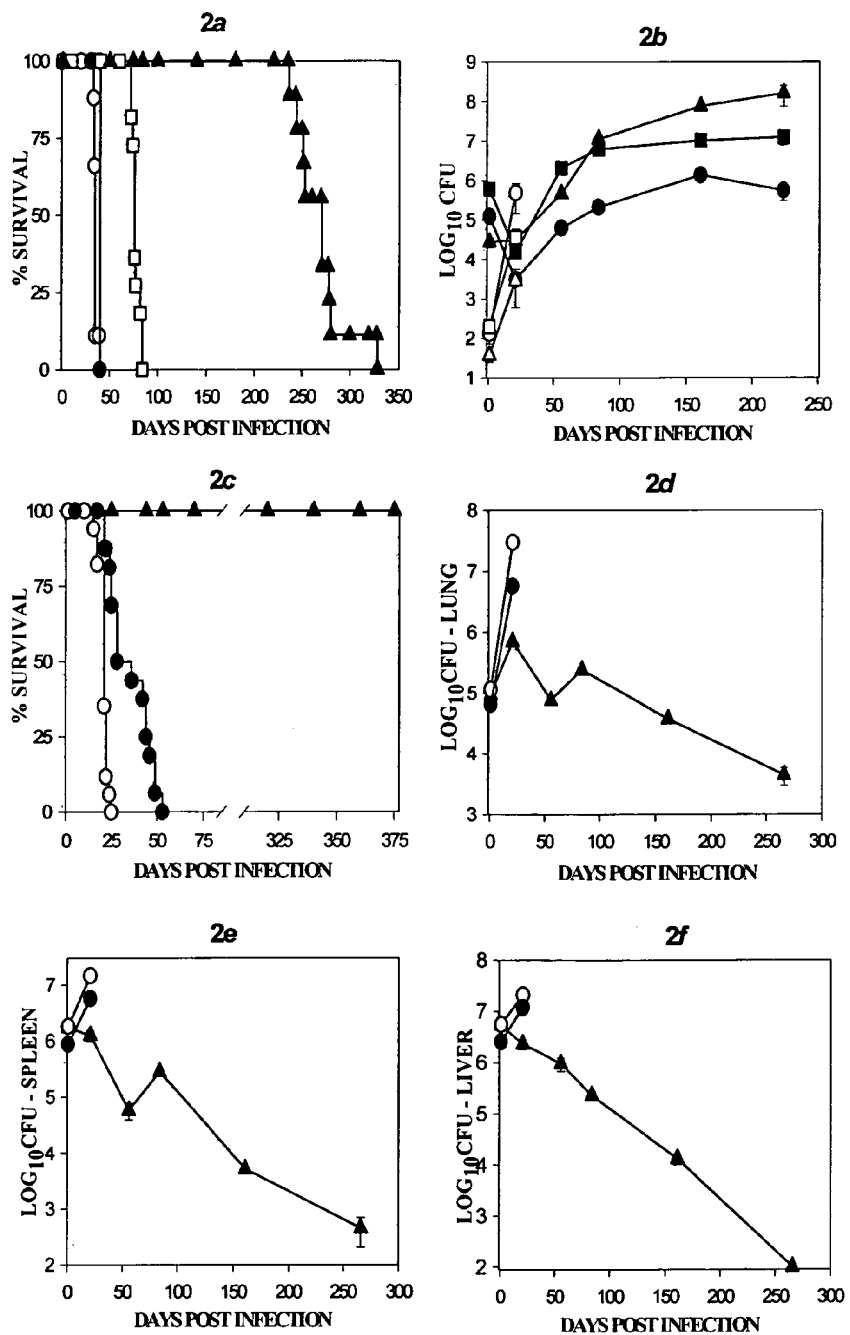
Figure 11:
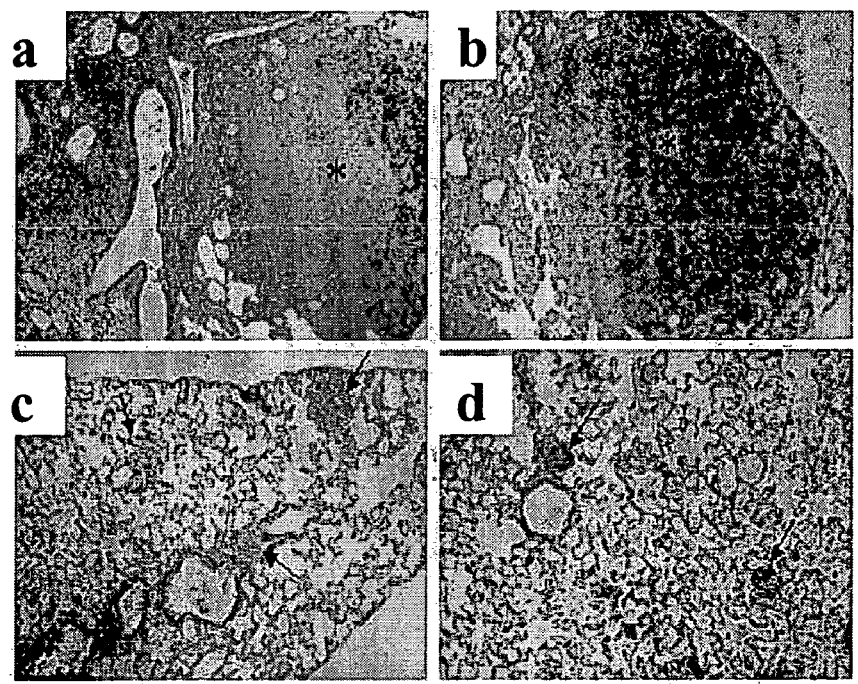
Figure 11:
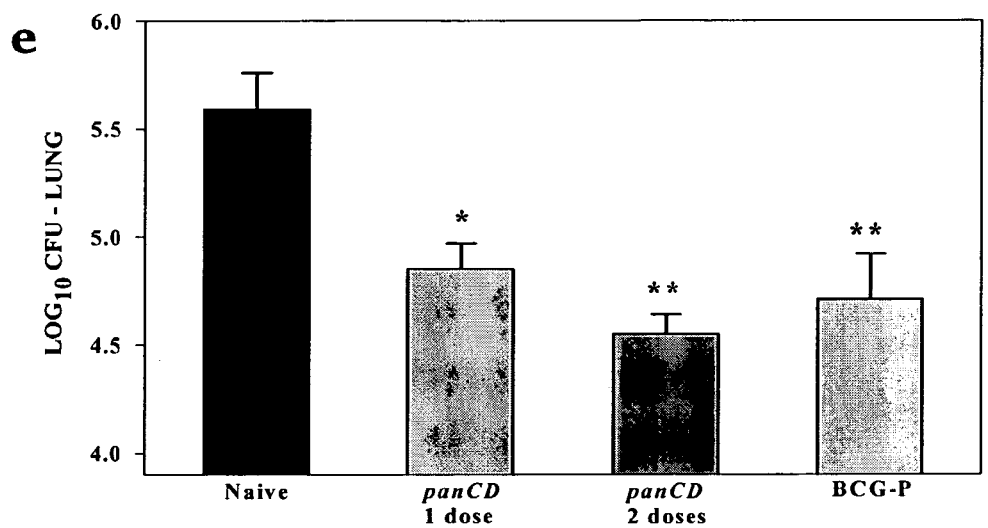
Figure 11:
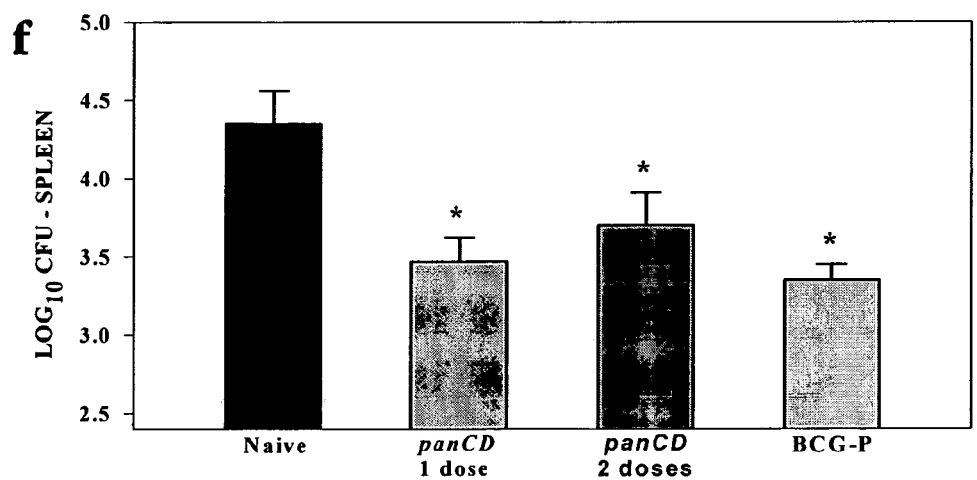

We constricted a double deletion mutant of *M. tuberculosis* in the panC and panD genes that are involved in the de novo biosynthesis of pantothenate (FIG. 9*b,c*). The ΔpanCD mutant was found to be auxotrophic for pantothenate with no detectable reversion to prototrophy when $1\times10^{10}$ cells were plated on minimal medium. The growth rate of the mutant was identical to wild type H37Rv in broth cultures in the presence of exogenous pantothenate (data not shown). The attenuation of the ΔpanCD mutant was assessed by infection of immunocompromised SCID mice. SCID mice infected intravenously with H37Rv succumbed to the resulting infection in about 5 weeks. In contrast, all mice infected with the ΔpanCD mutant survived for more than 36 weeks (average, 253 days) (FIG. 10*a*). This attenuation is due to pantothenate auxotrophy as the full virulence phenotype was restored when the panCD wild type genes were integrated into the chromosome of the ΔpanCD mutant in single copy. Enumeration of bacterial burdens in SCID mice infected with H37Rv and the ΔpanCD-complemented strain showed a rapid increase in bacterial numbers in the spleen, liver and lung, until they succumbed to infection. In contrast, mice infected with the ΔpanCD mutant showed an initial drop in bacterial numbers in the spleen and liver followed by a gradual increase in the number of viable bacteria, reaching $1\times10^{6}$ colony-forming units (CFU) by day 224 (FIG. 10*b*). Notably, the CFU values increased to $1\times10^{8}$ in the lungs of the infected mice. The ability of ΔpanCD-infected SCID mice to survive despite a substantial bacterial burden in their lungs emphasizes the extent of attenuation in this mutant and compares with the phenotype observed with the *M. tuberculosis* whiB3 and sigH mutants described recently (Steyn et al., 2000; Kaushal, 2000). Notably, SCID mice infected with bacille Calmette-Guerin-Pasteur (BCG-P) strain succumbed to infection by 83 days (Weber et al., 2000) in contrast to the prolonged survival observed in ΔpanCD-infected mice.

Studies in immunocompetent mice further demonstrate the attenuation of the ΔpanCD mutant. Survival studies showed that BALB/c mice infected with H37Rv succumbed to infection by day 25 (average, 21 days) and mice infected with an identical dose of the panCD-complemented strain succumbed to infection between days 21 to 53 (average, 37 days). Importantly, all mice infected with $1\times10^{6}$ CFU of the ΔpanCD mutant survived 375 days, when the experiment was terminated (FIG. 10*c*). At 3 weeks post infection, in contrast to the H37Rv strain, BALB/c mice infected with ΔpanCD mutant showed a 10-fold increase in bacterial numbers in the lungs followed by a gradual decline in viable numbers over the next 38 weeks of infection (FIG. 10*d*) and the bacterial burden gradually declined in the spleen and liver throughout the course of infection (FIG. 10*e*). Histopathologic examination of the lungs from mice infected with either H37Rv or the ΔpanCD-complemented strain, showed severe, diffuse lobar granulomatous pneumonia (FIG. 11*a,b*). The pneumonia affected more than 50% of the lung, and was pyogranulomatous with marked necrosis in the advanced consolidated areas, particularly in the lungs of mice challenged with H37Rv. Both of these strains caused severe granulomatous splenitis and widespread granulomatous hepatitis. At 3 weeks post-infection with the ΔpanCD mutant, low to moderate numbers of focal infiltrates of mononuclear cells scattered throughout the lung were seen (FIG. 11*c*). The spleen was moderately enlarged with scattered granulomas. Similarly, the liver showed numerous focal granulomas. At 24 weeks post-infection, consistent with the bacterial numbers, histological examination of the lungs from mice infected with the ΔpanCD mutant showed only occasional focal mild infiltrations, predominately lymphocytic (FIG. 11*d*). The spleen showed only mild histiocytic hyperplasia and there were fewer, focal, predominately lymphocytic accumulations in the liver.

The mechanisms that allow the persistence of the ΔpanCD mutant bacteria for over 8 months in the SCID mouse model remain unclear. We speculate the functional role of an unidentified permease in transporting adequate amount of pantothenate in the ΔpanCD mutant that allows its persistence but not the ability to cause disease. A pantothenate permease that transports pantothenate has been described in *Plasmodium falciparum* and *Escherichia coli* (Saliba and Kirk, 2001; Jackowski and Alix, 1990). In the lungs of immunocompetent mice, an initial growth of the ΔpanCD mutant during the first 3 weeks is followed by a steady decline in bacterial numbers following the onset of an adaptive immune response. The intracellular lifestyle of *M. tuberculosis* poses significant challenges to the bacterium in acquiring essential nutrients. Pantothenic acid or its derivatives have been shown to confer resistance to oxidative stress (Slyshenkov et al., 1996) and lack of pantothenate biosynthesis in the ΔpanCD mutant may render it more susceptible to such adverse effects. Likewise, a pantothenate kinase (panK) mutant of *Drosophila* was shown to display membrane defects and improper mitosis and meiosis due to decreased phospholipid biosynthesis (Afshar et al., 2001). Therefore, it is plausible that the pantothenate salvage pathway is inadequate in restoring full virulence of the ΔpanCD mutant in the absence of a functional de novo biosynthetic pathway.

As a test of vaccine potential, immunized mice were challenged with virulent *M. tuberculosis* Erdman by the aerosol route (Collins, 1985). Following subcutaneous immunization, the ΔpanCD mutant could not be detected in the spleens or lungs of mice at 8 and 12 weeks. In the naive controls, the bacterial CFU values increased 10,000-fold in the lung during the first month after challenge. Similarly, substantial dissemination and growth in the spleen was detected within one month of the challenge in naive controls. In contrast, mice immunized with single or double doses of the ΔpanCD mutant displayed statistically significant reductions ($P<0.05$) in lung and spleen CFU values relative to naive controls. Mice vaccinated with BCG showed similar reduction in organ bacterial burdens compared to the nonimmunized controls (FIG.

11e,f). In these aerogenic challenge studies, no significant differences were detected in the lung and spleen CFU values for mice vaccinated with either the ΔpanCD mutant strain or with BCG. At 28 days after the aerogenic challenge with virulent M. tuberculosis, histopathological examination of lungs of ΔpanCD immunized mice revealed a less severe infection relative to the unvaccinated control mice. In controls, severe bronchitis, moderate pneumonia, and spread of the infection to the adjacent lung parenchyma was observed. By comparison, the ΔpanCD vaccinated mice had milder bronchitis and smaller areas of mild interstitial pneumonitis, with localized areas of granulomatous pneumonia in some mice. Importantly, no lung pathology was detected in vaccinated mice at the time of challenge (data not shown). Two groups of mice that were vaccinated with one or two doses of the ΔpanCD mutant and then challenged with M. tuberculosis Erdman were active and healthy for more than one year following the virulent challenge. Histopathological analysis of lung sections from these mice showed only mild inflammation and fibrosis despite the chronic infection.

By creating a M. tuberculosis strain that is defective in pantothenate biosynthesis, we have taken a critical step in the rational development of an attenuated M. tuberculosis vaccine strain. We have shown that a functional pantothenate biosynthetic pathway, which is required for the synthesis of complex mycobacterial lipids, is essential for the virulence of M. tuberculosis. Although the precise mechanism of the reduced virulence is unclear, it is reasonable to speculate that this could be due to reduced synthesis of toxic polyketides and secreted lipids or a general slow down of metabolism. Tubercle bacilli lacking the two genes required to synthesize pantothenate failed to revert and were highly attenuated and less virulent than BCG vaccine when tested in the rigorous SCID mouse model of infection. Despite the reduced virulence associated with the deletion of the panCD genes, these vitamin auxotrophs remain persistent in vivo as shown by their ability to survive for at least eight months in immunocompetent mice. The persistence of this mutant strain undoubtedly contributes to the substantial immunogenicity seen in the mouse tuberculous challenge model. Overall, the ΔpanCD mutant has many of the characteristics necessary for a live vaccine candidate strain: it is attenuated by a non-reverting mutation and essentially avirulent while being persistent and immunogenic. Given the genetic differences between M. bovis and M. tuberculosis (Behr et al., 1999), one would predict that a rationally attenuated M. tuberculosis strain would have a more relevant repertoire of species-specific antigens and thus should elicit, in humans, more effective protective immune responses against tuberculous infections than BCG.

EXAMPLE 4

The Primary Mechanism of Attenuation of BCG is a Loss of Invasiveness Due to Host Cell Lysis Example Summary.

Tuberculosis remains a leading cause of death worldwide, despite the availability of effective chemotherapy and a vaccine. BCG, the tuberculosis vaccine, is an attenuated mutant of M. bovis that was isolated following serial subcultivations, yet the basis for this attenuation has never been elucidated. A single region (RD1), deleted in all BCG substrains, was deleted from virulent M. bovis and M. tuberculosis strains and the resulting three ΔRD1 mutants were significantly attenuated for virulence in both immunocompromised and immunocompetent mice. Like BCG, M. tuberculosis ΔRD1 mutants protect mice against aerosolized M. tuberculosis challenge and these mutants also consistently display altered colonial morphotypes. Interestingly, the ΔRD1 mutants failed to cause necrosis, via lysis, of pneumocytes, a phenotype that had been previously used to distinguish virulent M. tuberculosis from BCG. We conclude that the primary attenuating mechanism of BCG is the loss of cytolytic activity, resulting in reduced invasiveness.

Introduction.

BCG (bacille Calmette and Guerin), was first isolated from M. bovis following serial subculturing of M. bovis in 1908 (Calmette and Guerin, 1909). Drs. Calmette and Guerin set out to test the hypothesis that a bovine tubercle bacillus could transmit pulmonary tuberculosis following oral administration (Calmette and Guerin, 1905; Gheorghiu, 1996) and developed a medium containing beef bile that enabled the preparation of fine homogenous bacillary suspensions. After the 39th passage, the strain was found to be unable to kill experimental animals (Calmette and Guerin, 1909). Between 1908 and 1921, the strain showed no reversion to virulence after 230 passages on bile potato medium (Gheorghiu, 1996), which is consistent with the attenuating mutation being a deletion mutation. In the animal studies that followed, BCG was shown to be attenuated, but it also protected animals receiving a lethal challenge of virulent tubercle bacilli (Calmette and Guerin, 1920). BCG was first used as a vaccine against tuberculosis in a child in 1921 (Weill-Halle and Turpin, 1925). From 1921 to 1927, BCG was shown to have protective efficacy against TB in a study on children (Id.; Calmette and Plotz, 1929) and was adopted by the League of Nations in 1928 for widespread use in the prevention of tuberculosis. By the 1950's, after a series of clinical trials, the WHO was encouraging widespread use of BCG vaccine throughout the world (Fine and Rodrigues, 1990). Although an estimated 3 billion doses have been used to vaccinate the human population against tuberculosis; the mechanism that causes BCG's attenuation remains unknown.

Mahairas et al. (1996) first compared the genomic sequences of BCG and M. bovis using subtractive hybridization and found that there were three Regions of Difference (designated RD1, RD2, and RD3) present in the genome of M. bovis, but missing in BCG. Behr et al. (Behr et al., 1999) and others (Gordon et al., 2001) later identified 16 large deletions, including RD1 to RD3, present in the BCG genome but absent in M. tuberculosis. Eleven of these 16 deletions were unique to M. bovis, while the remaining 5 deletions were unique to BCG. One of these 5 deletions, designated RD1 (9454 bp), was absent from all of the BCG substrains currently used as TB vaccines worldwide and it was concluded that the deletion of RD1 appeared to have occurred very early during the development of BCG, probably prior to 1921 (Behr et al., 1999). It is reasonable to hypothesize that RD1 was the primary attenuating mutation first isolated by Calmette and Guerin to generate BCG from M. bovis. Attempts to restore virulence to BCG with RD1-complementing clones have been unsuccessful (Mahairas et al., 1996).

Results.

RD1 deletions of M. bovis and M. tuberculosis are attenuated for virulence in immunocompromised mice. To test if RD1 is essential for virulence in M. bovis and M. tuberculosis, it was necessary to delete the RD1 (FIG. 1a) from virulent strains, demonstrate loss of virulence, and then restore virulence by complementation with the RD1 DNA. Since the original M. bovis parent of BCG was lost in World War I (Grange et al., 1983), we initiated studies with virulent M.

Figure 12:
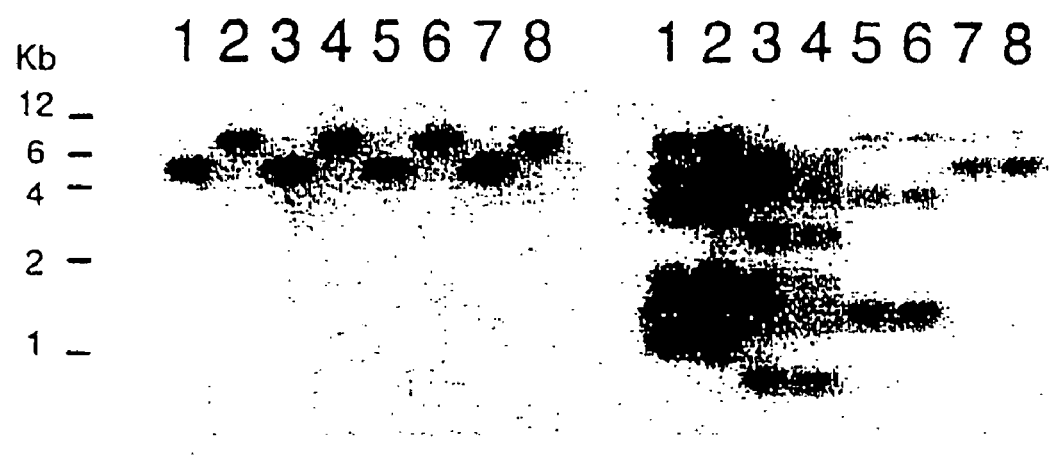

*bovis* Ravenel and a variety of virulent *M. tuberculosis* strains. Despite success in generating an unmarked deletion mutant of RD1 in *M. tuberculosis* with a plasmid transformation system 2, over 100 independent transformations failed to yield an RD1 deletion in *M. bovis*. As an alternative strategy, specialized transduction (Bardarov et al., 2002)$_3$ was successfully used to generate RD1 deletion mutants not only in *M. bovis* Ravenel, but also the H37Rv, Erdman, and CDC1551 strains of *M. tuberculosis* (FIG. 12). This deletion represents the largest deletion mutation generated by a targeted disruption in *M. tuberculosis* or *M. bovis* made to date and demonstrates the utility of the specialized transduction system. Moreover, since the parental specialized transducing phage has been shown to infect over 500 clinical *M. tuberculosis* isolates (Jacobs et al., 1987), it should be possible to introduce the RD1 deletion into any *M. tuberculosis* or *M. bovis* isolate of interest.

To determine if the RD1 deletion causes an attenuating phenotype in *M. bovis* and *M. tuberculosis*, the *M. tuberculosis* H37Rv ΔRD1 was inoculated intravenously into immunocompromised mice possessing the SCID (severe combined immunodeficiency) mutation. Groups of ten mice were injected intravenously with either $2\times10^6$ wild type or ΔRD1 strain of *M. tuberculosis* and *M. bovis*, and three mice per group were sacrificed 24 hours later to verify the inoculation doses. All of the SCID mice infected with the parental *M. tuberculosis* or *M. bovis* strain died within 14 to 16 days post-infection (FIG. 12A). In contrast, the SCID mice infected with equal doses of the ΔRD1 strains of *M. tuberculosis* or *M. bovis* were all alive at 25 to 41 days post-infection, demonstrating a highly significant attenuation of the virulence of both strains. It is important to note that BCG-Pasteur kills SCID mice approximately 70 days post-infection (FIG. 13B), suggesting that BCG substrains have acquired additional attenuating mutations which are consistent with the deletion analysis of BCG strains (Behr et al., 1999) and the previous failures to restore virulence with the RD1 region (Mahairas et al., 1996).

Figure 13:
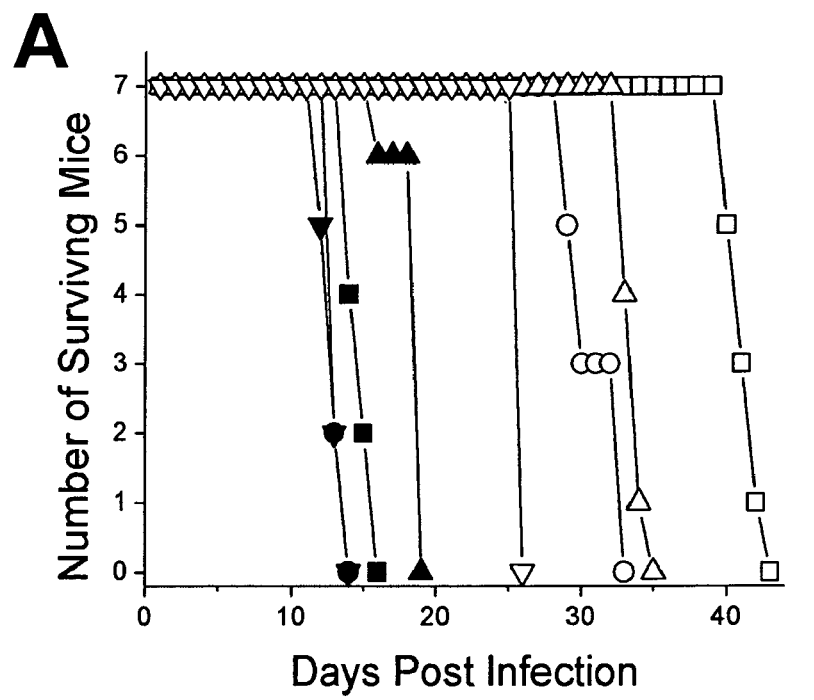
Figure 13:
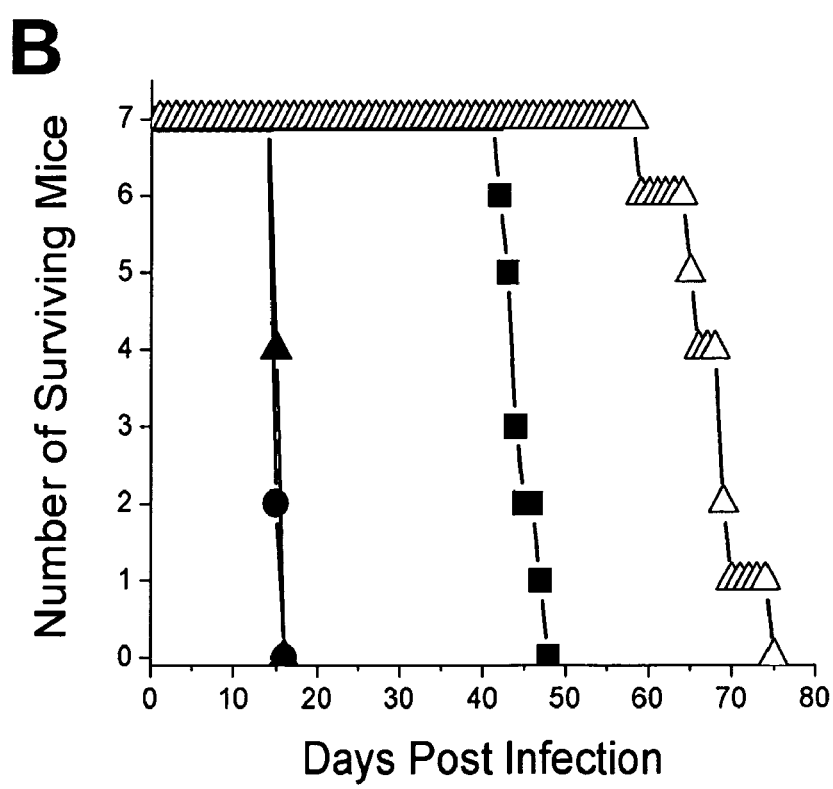
Figure 14:
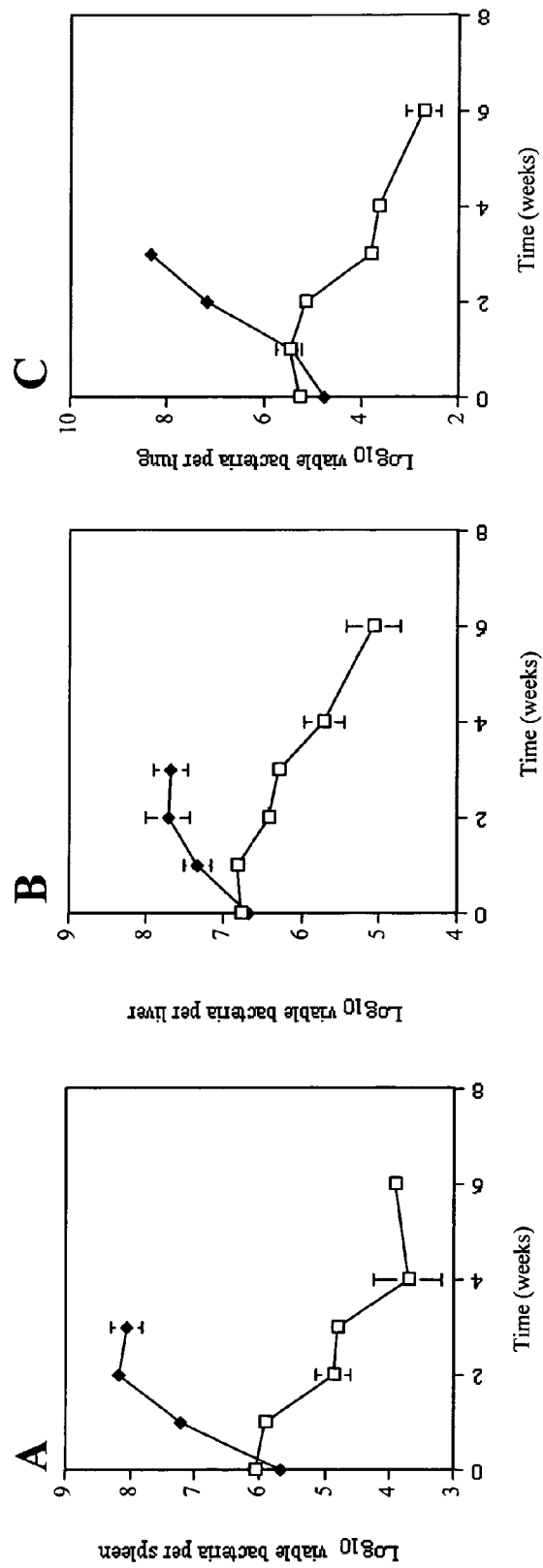

To prove that the attenuation of virulence was due to the RD1 deletion, the *M. tuberculosis* ΔRD1 was transformed with an integrating cosmid, 2F9, containing the RD1 region from *M. tuberculosis* H37Rv$^4$. SCID mice were infected as described above and the attenuation for virulence was restored to the parental virulent phenotype (FIG. 13B). These results strongly suggest that the genes deleted from the RD1 region contribute to the virulence phenotype.

The *M. tuberculosis* ΔRD1 is highly attenuated in immunocompetent BALB/c mice. The virulence of the *M. tuberculosis* ΔRD1 mutant was further assessed by intravenous inoculation of immunocompetent BALB/c mice. While the virulent parent *M. tuberculosis* strain killed the BALB/c mice in 10 to 17 weeks post-infections, 100% of mice were alive at 48 weeks and 43 weeks post-infections in two independent experiments (FIG. 13C).

While infection with BCG and *M. tuberculosis* ΔRD1 yielded similar survival results in BALB/c mice, there were substantial differences in the growth kinetics in mice. BCG grew in a limited fashion in lungs, liver and spleen in BALB/c mice during the 22 weeks of the experiment (FIG. 4B-D). In contrast, the *M. tuberculosis* ΔRD1 strain grew in a fashion indistinguishable from the parental *M. tuberculosis* H37Rv in all mouse organs for the first 8 weeks. Thereafter, mice infected with the parental *M. tuberculosis* failed to contain the infection leading to mortality. Strikingly, mice infected with the *M. tuberculosis* ΔRD1 showed a definite control over infection resulting in significantly prolonged survival of mice (FIG. 4B-D).

Histopathological examination further demonstrated that the mutant was attenuated in virulence compared to the parent strain H37Rv (FIG. 5D-F). In contrast to the rapidly progressive infection with the parent strain, the lung lesions caused by the mutant were maximal in mice examined at 8 weeks post-infection. Consolidating granulomatous pneumonia involved an estimated 25-30% of the lung in these mice. Numerous organisms were demonstrated by acid fast staining. The pneumonia subsequently underwent partial resolution. By 14 weeks, and again, at 22 weeks post-infection, the lungs showed peribronchial and perivascular inflammatory cell accumulations and focal, generally non-confluent, granulomas now with a promiment lymphocytes infiltration. The numbers of acid fast bacilli were reduced. Liver lesions consisted of low numbers of scattered granulomas. Spleens were smaller, with persistent granulomas in the red pulp. Mice infected with *M. bovis* BCG showed mild lesions in the lung, liver and spleen at all time points (FIG. 5G-I). At longer time intervals post-infection the lesions were fewer in number, and smaller with prominent lymphocytic infiltrations. At 14 weeks post-infection, *M. bovis* BCG was below the level of detection by acid fast staining. In summary, whereas *M. tuberculosis* ΔRD1 initially grew in a manner similar to the parental *M. tuberculosis* H37Rv, this RD1 mutant was limited in the extent of spread of infection, particularly in the lung. This contrasts the extensive and severe damage caused by the parent strain. The subsequent resolving granulomas, localization of the lesions and changes in the composition of the inflammatory cell infiltrations suggested that the mice mounted an effective immune response to combat *M. tuberculosis* ΔRD1 infection and thereby reduced the numbers of viable organisms.

Early BCG properties: Altered colonial morphotypes and long-term immunogenicity. While frozen stocks of the original BCG stain do not exist, written records do exist describing the early BCG stains, as Dr. Calmette sent the stains to many laboratories. In a study published in 1929, Petoff and colleagues reported that BCG displayed two distinct colony types (Petroff et al., 1929). One morphotype was a smooth (S) phenotype that was flat and corded (like the parental virulent strain) and the second was a rough and raised (R) phenotype. The *M. tuberculosis* ΔRD1 mutant was generated independently four times and consistently yielded a 20 to 50% mixture of two colonial morphotypes on Middlebrook medium without Tween 80 (FIG. 3*b*). The distinction of these two types of morphology could be noted even when the colonies were less than two weeks old, as the rough colonies were constricted and elevated with only a small portion of the base of the colony attached to the agar, while the smooth colonies tended to be flattened and spread out. When colonies grew older, e.g. 6 weeks old, the rough colonies remained more constricted compared to those of smooth colonies. The rough colonies exhibited large folds on the surface (FIG. 3*f-g*), as compared to those of the smooth colonies that exhibited small wrinkles (FIG. 3*e*).

The generation of two distinct colonial morphotypes must be a phenotypic change induced by the deletion of RD1. The morphotypes could not be cloned, as repeated subculturing of either the R or S colonies continued to yield both colonial morphotypes. Moreover, Southern analysis of R and S colonies revealed each morphotype had the same RD1-deleted genotype (FIG. 3*d*). Furthermore, complementation of *M. tuberculosis* ΔRD1 with the RD1 region restored the mutant phenotype back to the homogenous parental S phenotype (FIG. 3*a-c*). These results suggest that the variable morphotypes resulted directly from the RD1 deletion. It can therefore be postulated that a regulator of colonial morphology is affected by one or more of the deleted genes.

One of the hallmark characteristics of BCG is its ability to provide protection against aerosolized challenge with virulent *M. tuberculosis*. To test the potential of *M. tuberculosis* ΔRD1 to immunize and protect mice against tuberculous challenge, we used the model of subcutaneous immunization of C57BL/6 mice followed by an aerogenic challenge with virulent *M. tuberculosis* (McGuire et al., 2002). Groups of mice were vaccinated subcutaneously with either 1×10⁶ BCG 9 or 1×10⁶ *M. tuberculosis* ΔRD1. Eight months following vaccination, the mice were all healthy, thereby demonstrating attenuation in a third mouse strain. Vaccinated and unvaccinated mice were aerogenically challenged with 200 CFU of the acriflavin-resistant strain of *M. tuberculosis* Erdman. Twenty-eight days after the challenge, the mice were sacrificed and the bacterial burden in the lungs and spleens were determined (see Table 5). Naive mice served as controls. While the acriflavin-resistant *M. tuberculosis* grew to $6.61 \pm 0.13$ ($\log^{10}$ CFU) in lungs of naive mice, both the BCG-vaccinated and *M. tuberculosis* ΔRD1-vaccinated mice exhibited greater than 1 log protection in lungs with CFU values of $5.07 \pm 0.10$ ($p<0.001$ relative to controls) and $5.11 \pm 0.14$ ($p<0.001$), respectively, detected at the four week time point. The *M. tuberculosis* ΔRD1 also protected against hematogenous spread; CFU values in the spleen were $5.26 \pm 0.11$ for the controls, $4.00 \pm 0.33$ ($p<0.01$) for the *M. tuberculosis* ΔRD1 immunized mice, and $3.85 \pm 0.17$ ($p<0.01$) for the BCG vaccinated animals. Thus, the *M. tuberculosis* ΔRD1 shares long-term immunogenicity like BCG.

TABLE 5

Bacterial burden of virulent *M. tuberculosis* in uninoculated mice and mice inoculated with BCG and H37Rv ΔRD1.

| Vaccination strain | Lung ($\log_{10}$CFU) | Spleen (log10CFU) |
|---|---|---|
| — | $6.61 \pm 0.13$ | $5.26 \pm 0.11$ |
| BCG | $5.07 \pm 0.10$*** | $3.85 \pm 0.17$** |
| H37Rv ΔRD1 | $5.11 \pm 0.14$*** | $4.00 \pm 0.33$** |

**$p < 0.01$;
***$p < 0.001$.

Discussion

BCG is a mutant of *M. bovis* that was isolated over 94 years ago and characterized for its attenuation for virulence in animals. For over 80 years, BCG has been used as a tuberculosis vaccine having been given to 3 billion humans. It is currently the only anti-tuberculous vaccine available for use in humans, yet its precise attenuating mutations and mechanisms of attenuation have never been determined. Previous studies had identified regions of the *M. bovis* chromosome that were absent from BCG, but present in virulent *M. bovis* and *M. tuberculosis* strains (Mahairas et al., 1996; Gordon et al., 2001). An elegant microarray analysis has also demonstrated that there was only one deletion common to all BCG strains; the authors hypothesized this was the primary attenuating mutation in the original BCG strain isolated by Drs. Calmette and Guerin (Behr et al., 1999).

Using a combination of targeted deletion mutagenesis, virulence assays, and complementation analysis, we have been able to unambiguously prove that RD1 is required for virulence for *M. tuberculosis*, and by analogy for *M. bovis*, for the first time.

Moreover, the combination of phenotypes associated with the early BCG strains: i) the attenuation for virulence, ii) the altered colonial morphotypes, and iii) the ability to confer long-term immunogenicity in animals allow us to conclude that the RD1 deletion was the primary attenuating mutation in the original BCG isolate.

With regards to the ΔRD1 mutant histology, at 22 weeks post infection, it was noted that the mutant was limited in the extent of the spread of infection, in contrast to the extensive damage caused by the parental strain. Interestingly, Pethe et al. (2001) determined that *M. tuberculosis* needs to bind and/or invade epithelial cells in order to disseminate and cause widespread destruction of the lung, whilst another study reported that pulmonary M cells can act as a portal of entry to the lung for the tubercle bacilli (Teitelbaum, 1999). In relation to in vitro analyses, studies utilizing a model of the alveolar barrier, consisting of pneumocytes and monocytes, described how *M. tuberculosis* infection of the pneumocytes resulted in cytolysis, which disrupted the barrier and allowed more efficient translocation of intracellular bacilli (Bermudez et al., 2002).

Example Notes

[1]The following four primers were used to amplify upstream and downstream flanking sequences (UFS and DFS, respectively) for the construction of the RD1 deletion mutants. UFS was amplified using TH201: GGGGGCG-CACCTCAAACC (SEQ ID NO:5) and TH202: ATGTGC-CAATCGTCGACCAGAA (SEQ ID NO:6). DFS was amplified using TH203: CACCCAGCCGCCCGGAT (SEQ ID NO:7, and TH204: TTCCTGATGCCGCCGTCTGA (SEQ ID NO:8). Recognition sequences for different restriction enzymes were included at the ends of each primer to enable easier manipulation.

[2]The unmarked deletion mutant of *M. tuberculosis* H37Rv, mc² 4002, was generated by transformation using a sacB counterselection (Snapper et al., 1988; Pelicic et al., 1996; Pavelka et al., 1999). Specifically, the plasmid pJH508 was created by first cloning UFS into KpnI and XbaI sites, then cloning DFS into EcoRI and HindIII sites of pJH12, a pMV261-derived *E. coli*-Mycobacteria shuttle plasmid, to create pJH506 in which UFS and DFS flanked a green fluorescent protein gene (GFPuv, Clonetech) whose expression was driven by the *M. leprae* 18 Kd promoter. The UFS-gfp-DFS cassette was sub-cloned into the EcoRV site of plasmid pYUB657 to create pJH508. The first homologous recombination involved the identification of hygromycin resistant colonies, resulting from the transformation of *M. tuberculosis* with pJH508. Southern analysis of the NcoI-digested DNA isolated from hygromycin resistant colonies probed with UFS or DFS, confirmed the presence of a single copy of pJH508 inserted into the *M. tuberculosis* genome. The transformant (mc²4000) identified was then grown in 7H9 broth to saturation, to allow the second homologous recombination to occur, resulting in recombinants that could be selected by plating the culture on 7H10 plates, supplemented with 3% sucrose. Both Southern analysis and PCR of the DNA isolated from sucrose resistant colonies confirmed the RD1 deletion.

[3]Specialized transduction is a mycobacteriophage-based method for the delivery of homologous DNA constructs using conditionally replicating shuttle phasmids (Jacobs et al., 1987; Bardarov et al., 1997; Carriere et al., 1997) has been used successfully for *M. tuberculosis* (Glickman et al., 2000, 2001; Raman et al., 2001). Specifically, a transducing phage phAEKO1 was constructed by inserting UFS and DFS into pJSC347, flanking a hygromycin cassette, to create pJH313. pJH313 was digested with PacI and ligated to phAE159, a temperature-sensitive mycobacteriophage derived from TM4. The transduction was performed by growing *M. tuberculosis* to an O.D.$_{600}$ of 1.0, washing twice with MP buffer (50 mM Tris pH 7.6, 150 mM NaCl, 10 mM $MgCL_2$, 2 mM $CaCl_2$), resuspending into an equal volume of MP buffer and mixing with the transducing phage phAEKO1 at an MOI of 10. The mixtures were incubated at 37° C. overnight, then plated on 7H10 plates supplemented with hygromycin at 50 μg/ml. Hygromycin resistant colonies were analyzed by PCR and Southern analysis, as described above, to confirm the deletion of RD1.

[4]Complementation analyses was performed using the integration proficient cosmids (Skjot et al., 2000; van Pinxteren et al., 2000) pYUB412 made by S. Bardarov, a library made by F. Bange, and cosmid identified and generously provided by S.T. Cole.

EXAMPLE 5

Vaccine Efficacy of a Lysine Auxotroph of *M. Tuberculosis*

Figure 15:
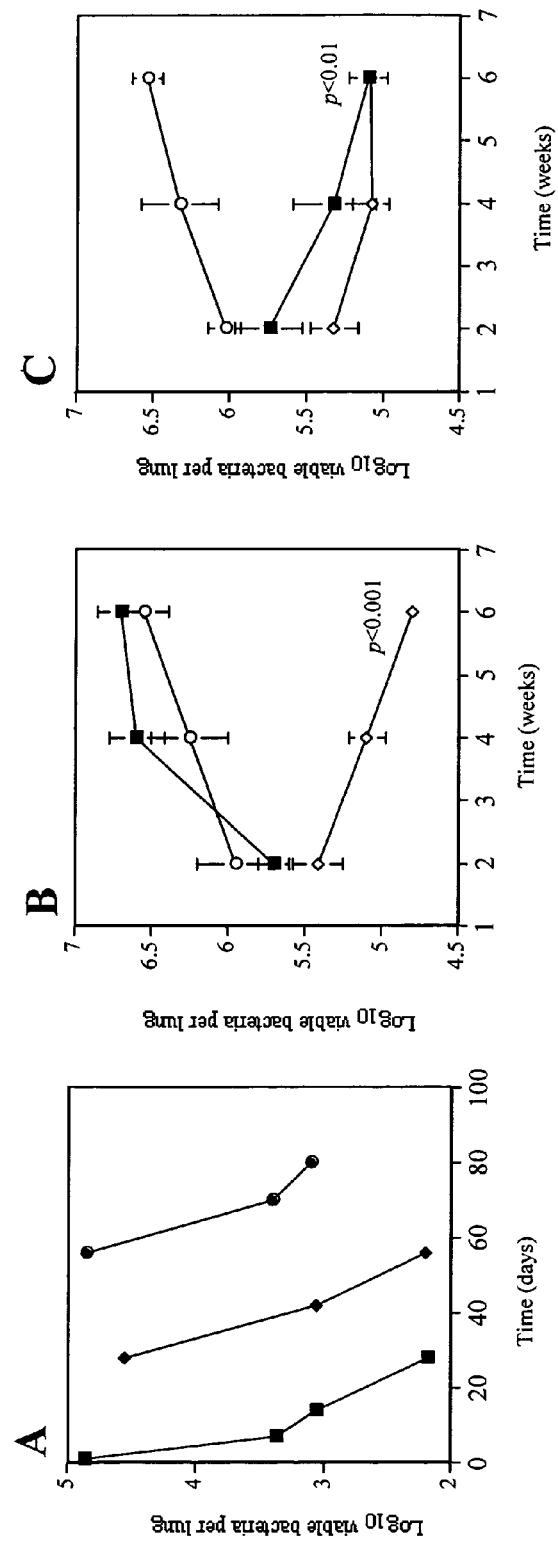
Figure 16:
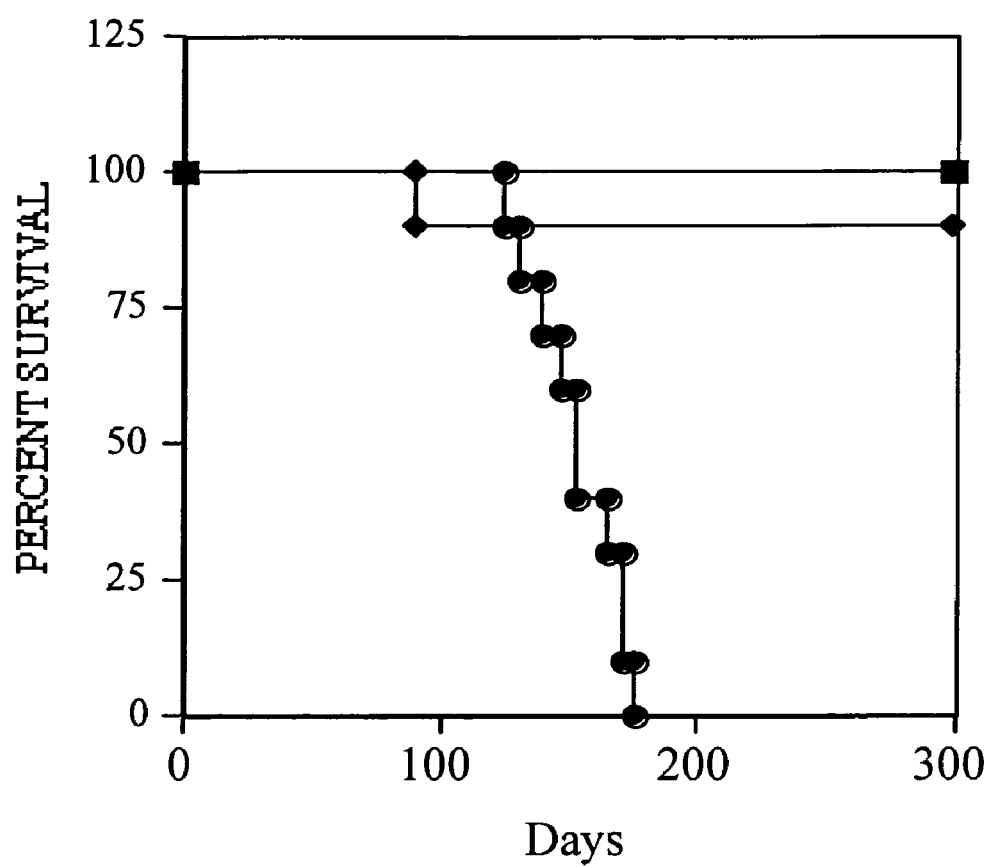

In this Example, we describe the in vivo growth phenotype and vaccine efficacy of a lysine auxotrophic mutant of *Mycobacterium tuberculosis* strain H37Rv. An immunization experiment using the mouse model with an aerosol challenge showed that two doses of the *M. tuberculosis* mutant were required to generate protection equivalent to that of the BCG vaccine.

Despite the existence of anti-microbial drugs and a widely used vaccine, *Mycobacterium tuberculosis* remains the primary cause of adult death due to a bacterial agent (Dolin et al., 1994). The emergence of multi-drug resistant strains of *M. tuberculosis*, the variable efficacy of the current vaccine, the bacille-Calmette and Geurin (BCG), and the HIV pandemic have all contributed to a growing global tuberculosis problem.

Several studies have described the development of attenuated auxotrophic strains of BCG and/or *M. tuberculosis* (Guleria et al., 1996); Hondalus et al., 2000; Jackson et al., 1999; Smith et al. 2001). All of these studies utilized single immunization protocols and demonstrated differences in the protective responses thus elicited. In this study, we describe the in vivo growth characteristics of a previously described lysine auxotroph of *M. tuberculosis* H37Rv (Pavelka and Jacobs, 1999), and evaluate the vaccine potential of this mutant by a multiple immunization protocol in a mouse model of the human disease, using an aerosol challenge.

Clearance of the *M. tuberculosis* lysine auxotroph in SCID mice. Female SCID mice were bred at the animal facility of the Albert Einstein College of Medicine. The animals were maintained under barrier conditions and fed sterilized commercial mouse chow and water ad libitum. The *M. tuberculosis* strains Erdman, $mc^2$3026 (ΔlysA::res) (Id.), and $mc^2$3026 bearing pYUB651 (expressing the wild-type lysA gene) were grown in Middlebrook 7H9 broth (Difco) supplemented with 0.05% Tween-80, 0.2% glycerol, 1×ADS (0.5% bovine serum albumin, fraction V (Roche); 0.2% dextrose; and 0.85% NaCl) or on Middlebrook 7H10 or 7H11 solid medium (Difco) supplemented with 0.2% glycerol and 10% OADC (Becton Dickinson). Culture media for the lysine auxotroph were supplemented with 1 mg/ml of L-lysine (for both liquid and solid media), and 0.05% Tween-80 was also added to solid medium. Liquid cultures were grown in 490 $cm^2$ roller bottles (Corning) at 4-6 rpm. Plates were incubated for 3-6 weeks in plate cans. All cultures were incubated at 37° C.

Titered frozen stocks of the bacteria were thawed and diluted appropriately in phosphate buffered saline containing 0.05% Tween-80 (PBST). The bacterial suspensions were plated at the time of injection to confirm the number of viable bacteria. Intravenous injections were given via a lateral tail vein. At various time points post-injection (24 hours, then once weekly), 3 mice were sacrificed, and the lungs, liver, and spleen removed and homogenized separately in PBST using a Stomacher 80 (Tekmar, Cincinnati, Ohio). The homogenates were diluted in PBST and plated to determine the number of CFU/organ. Note that mice were sacrificed at 24 hours post-injection in order to compare the bacterial colony forming units recovered from the mice with the colony forming units in the suspensions at the time of injection. Thus the bacterial counts reported at time zero actually represent the viable bacteria recovered from the mice at 24-hours post-injection.

The lysine auxotrophic strain was cleared from and did not appear to grow in the examined organs of the SCID mice, while the complemented strain multiplied extensively (FIG. 14). Interestingly, the auxotrophic inoculum was cleared from the spleens and lungs but persisted somewhat longer in the liver (FIG. 14B). The mice receiving the complemented *M. tuberculosis* mutant died within three weeks of challenge, while the mice given the auxotrophic *M. tuberculosis* mutant did not display any gross organ pathology and survived for at least the duration of the experiment.

Two immunizations with the *M. tuberculosis* lysine auxotroph $mc^2$3026 are required to match the efficacy of vaccination with BCG-Pasteur. We tested the vaccine potential of the lysine auxotroph $mc^2$3026 in the mouse model by means of a virulent aerosol challenge. Female, pathogen-free C57BL/6 mice (Jackson Laboratories, Bar Harbor, Me.) were vaccinated intravenously with ca. $1\times10^6$ CFU of the *M. tuberculosis* lysine auxotroph or BCG-Pasteur suspended in 0.2 ml PBST. Mice vaccinated with $mc^2$3026 were revaccinated at 4 week intervals and the number of viable organisms in the lungs and spleens determined weekly throughout the vaccination period, as described above for the SCID mouse experiments. Five mice were examined at each time point.

Immunized mice were challenged 3 months after the initial vaccination. A frozen aliquot of a *M. tuberculosis* Erdman stock was thawed and diluted in PBST to ca. $1\times10^6$ CFU/ml and 10 ml was introduced into the nebulizer of a Middlebrook aerosol chamber (Glas-Col, Terre Haute, Ind.). The mice were exposed to the infectious aerosol for 30 minutes, inhaling 50-100 CFU into their lungs over this period. Five mice were sacrificed immediately following the challenge period and the lung homogenates were plated to check the amount of the challenge inoculum actually reaching the lungs. Groups of vaccinated and control mice were sacrificed 14, 28, and 42 days later and the lung and spleen homogenates plated to determine the number of viable colony forming units of *M. tuberculosis* Erdman present. Data were analyzed using the Student's t-test and an analysis of variance between several independent means, using the In Stat Statistics program (GraphPad Software, San Diego).

A preliminary experiment demonstrated that a single intravenous immunization of immunocompetent C57BL/6 mice with the *M. tuberculosis* mutant did not generate a significant protective response to the subsequent aerosol challenge with virulent *M. tuberculosis* Erdman. In that experiment, the *M. tuberculosis* auxotroph was rapidly cleared from the mice (FIG. 15A), and the single immunization with the auxotroph was insufficient to reduce the bacterial burden in the lungs and spleens relative to a single immunization with BCG (FIG. 15B).

The failure of the auxotroph to confer protection might have been due to the inability of the mutant to persist long enough, or to synthesize enough antigen to induce an immune response that could significantly restrict the growth of the challenge organisms. One way to circumvent this problem is to give multiple doses of vaccine (Collins, 1991; Homchampa et al., 1992). To this end, mice were intravenously immunized two or three times at four-week intervals with the *M. tuberculosis* lysine auxotroph. In both cases, the vaccine strain was cleared from the lungs and spleens of all the mice at rates similar to that seen with the single immunization experiment (FIG. 15A). Three months after the first immunization the mice were challenged with *M. tuberculosis* Erdman by the aerosol route and the bacterial counts in the lungs and spleens were determined and compared to a BCG-Pasteur immunized control, as well as the sham immunized controls. As seen in FIG. 15C, double immunization with the *M. tuberculosis* lysine auxotroph induced a protective response that was equivalent to that of the BCG control. The reduction in counts in the lung and spleen was equivalent to a 100-fold reduction in bacterial counts compared to the unvaccinated control (FIG. 15C). The results from the triple immunization experiment were essentially similar as those from the double immunization experiment described above (data not shown). Furthermore, mice that were immunized with three doses of the *M. tuberculosis* lysine auxotroph and challenged with virulent *M. tuberculosis* Erdman survived at least as long as the BCG-immunized control mice (FIG. 16).

Several studies have described the development and vaccine efficacy of attenuated mutant strains of *M. tuberculosis* (Jackson et al., 1999; Hondalus et al., 2000; Smith et al., 2001). The first study reported that a purine auxotroph of *M. tuberculosis* was unable to grow in macrophages and was attenuated for growth in both mice and guinea pigs (Jackson et al., 1999). A guinea pig vaccination experiment determined that a single immunization with the auxotroph allowed the animals to restrict the growth of virulent *M. tuberculosis* in the lungs as well as a single immunization with wild-type BCG, following aerosol challenge. However, the reduction in growth of the challenge organism in the spleen afforded by the auxotroph was not as extensive as that afforded by BCG. Another study reported that a leucine auxotroph of *M. tuberculosis* H37Rv cannot grow in macrophages and is avirulent to immunocompromised SCID mice (Hondalus et al., 2000). Immunocompetent mice vaccinated once with a *M. tuberculosis* leucine mutant did not significantly restrict the growth of the virulent challenge organism in the lungs or spleen as much as the control mice vaccinated with BCG (Id.). However, the mice immunized with the leucine auxotroph survived as long as the BCG immunized controls and exhibited a decreased histopathology relative to that seen in the non-immunized controls (Id.). A third study showed that *M. tuberculosis* proline and tryptophan auxotrophs were attenuated and a single immunization of mice with either of these mutants afforded protection against an intravenous challenge with virulent *M. tuberculosis*, comparable to that for BCG, as indicated by the mean survival times (Smith et al., 2001). In those experiments, mice immunized with pro or trp mutants could restrict the growth of the challenge organisms to the same extent as mice immunized with BCG, although the magnitude of protection in either case (*M. tuberculosis* auxotrophs or BCG) was not as extensive as that seen in the other studies (Id.).

In the present study we have demonstrated that a single immunization of mice with the avirulent *M. tuberculosis* lysine auxotroph did not generate an immune response capable of significantly restricting the growth of virulent *M. tuberculosis* Erdman following an aerogenic challenge. However, administration of a second or a third dose of this vaccine increased protection substantially, as measured by the number of viable bacteria per organ, to a level similar to that achieved with single dose of BCG-Pasteur. This level of protection did not seem to be greatly increased by a third dose of vaccine, although the triply immunized mice survived as long as the control mice immunized with a single dose of BCG-Pasteur. Mice that were immunized twice were not followed to determine mean survival time, but comparing the growth curves of the challenge bacteria following the double and triple immunizations, it seems likely that the survival time for the doubly immunized mice would be much the same as that for the triple-immunized mice.

The previous studies using *M. tuberculosis* auxotrophs as vaccine strains showed substantial variations in their effectiveness. This variability is likely to be due to a number of factors, including the different *M. tuberculosis* background strains used to construct the mutants, different mouse strains used in the various protection studies, and the different challenge organisms and challenge routes used. There was also considerable variation in the protective efficacy of the different vaccines compared to that observed in controls using BCG immunization. These differences pose a number of questions concerning the best indicators of protection, especially in the long term. Should viable bacterial counts or survival be the primary indicator of protection or should both be given equal weight? The results of this study indicate that more than one immunization with a *M. tuberculosis* lysine auxotroph did generate a significant protective response as indicated by both criteria. We believe it is important that multiple immunization protocols be considered in the further development of attenuated *M. tuberculosis* strains as potential human vaccines.

This is the first study demonstrating that a multiple immunization protocol using an auxotroph of *M. tuberculosis* can protect against a highly virulent aerosol challenge compared to that seen for BCG. Since BCG vaccines have shown variable efficacy when tested in humans, an auxotrophic *M. tuberculosis* vaccine might represent an attractive booster vaccine with which to augment childhood BCG immunization.

EXAMPLE 6

Mutants of *Mycobacterium Tuberculosis* Having Two Attenuating Mutations are Safe and Provide Protection in Mammals Against Challenge from Virulent Mycobacteria The experiments described in this Example employ materials and methods described in the other Examples.

Construction and characterization of *M. tuberculosis* ΔRD1ΔpanCD (mc$^2$6030). A pantothenate auxotroph of *M. tuberculosis* ΔRD1 was generated by specialized transduction and the strain designated mc$^2$6030. No CFU were detected on 7H11 when 5×10 0 CFU were plated (repeated twice), suggesting the reversion frequency to be below $10^{-11}$.

Figure 17:
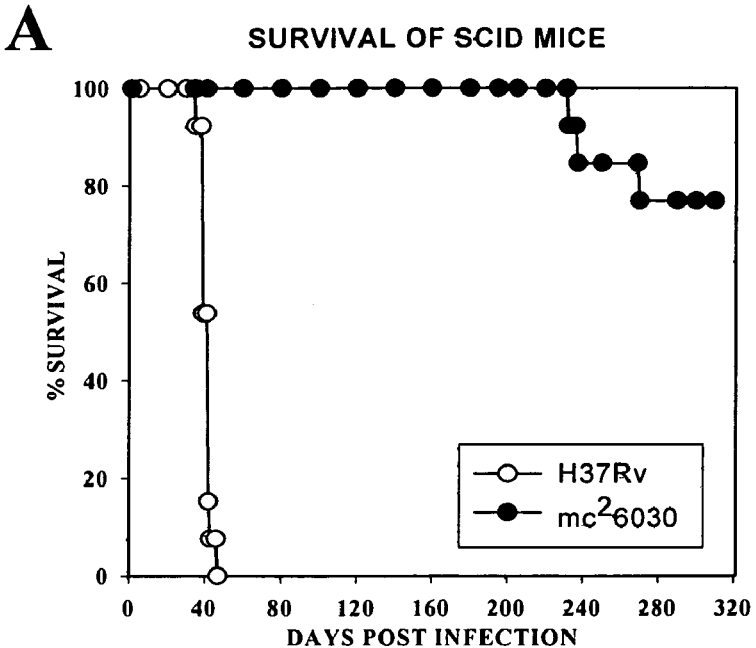
Figure 17:
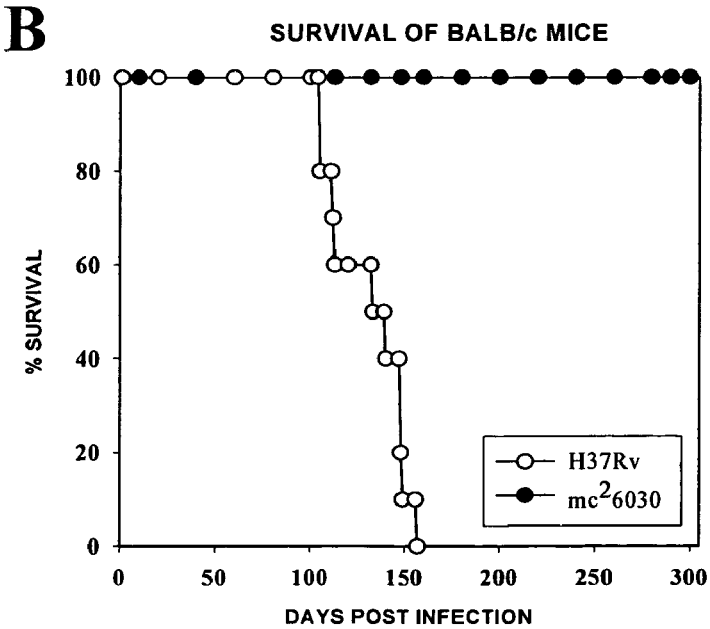
Figure 18:
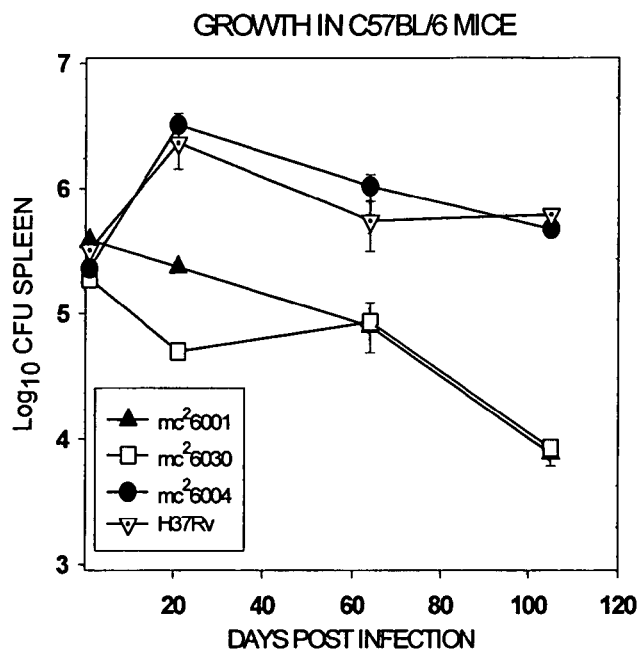
Figure 18:
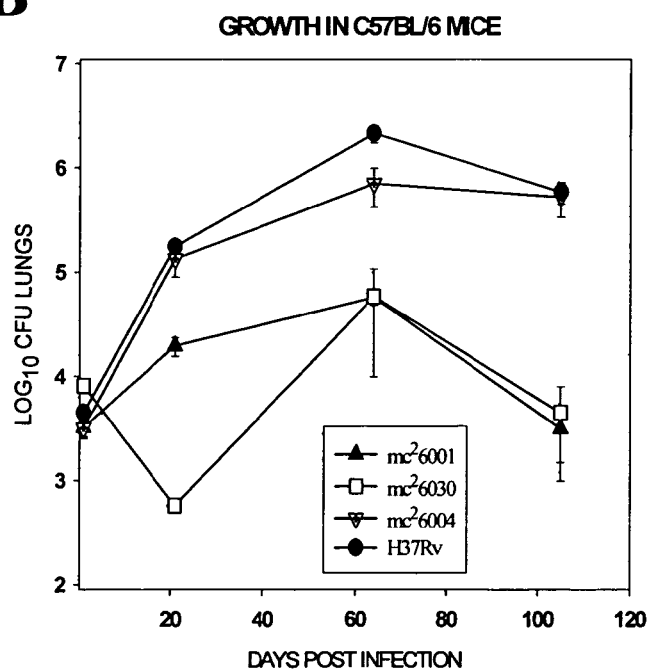
Figure 20:
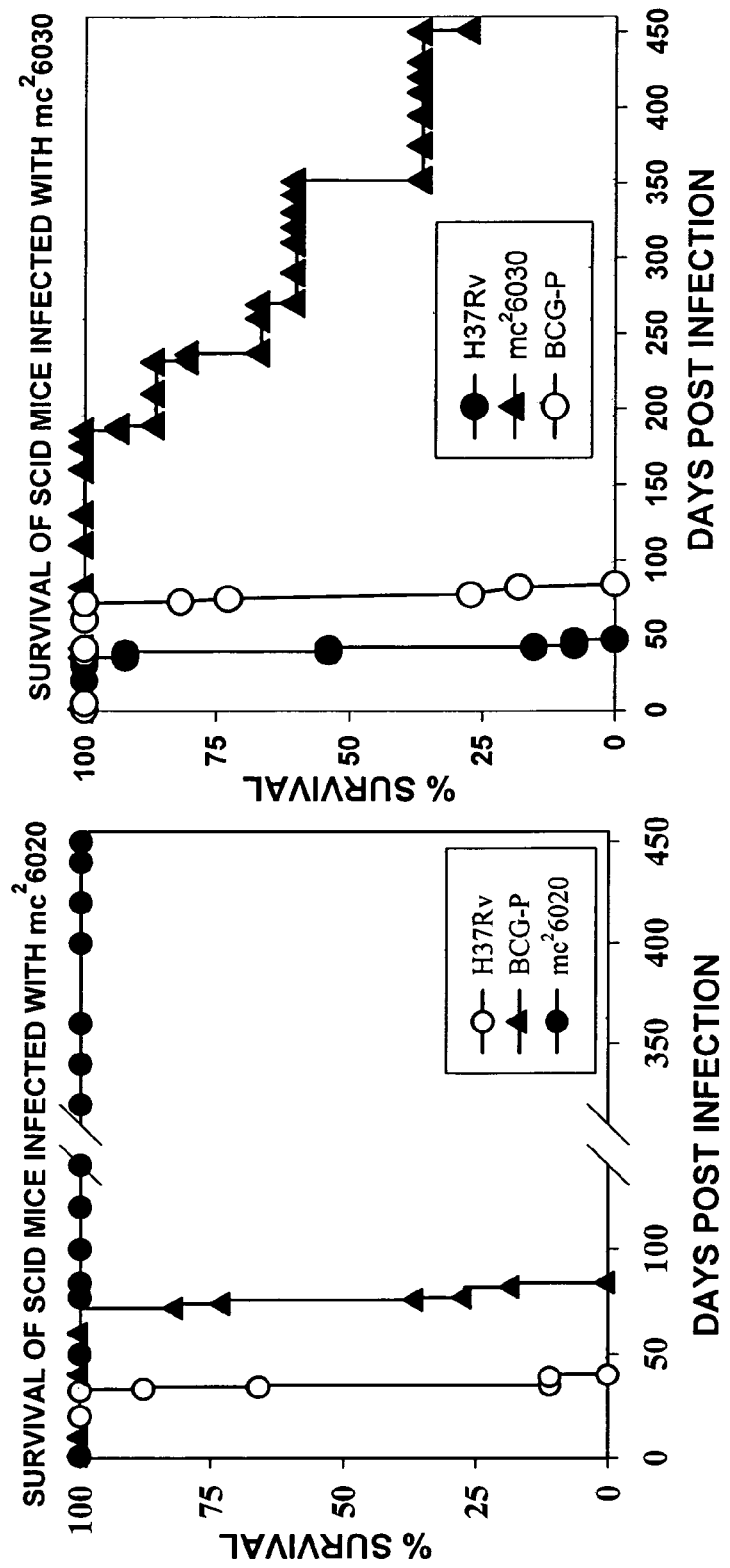
Figure 21:
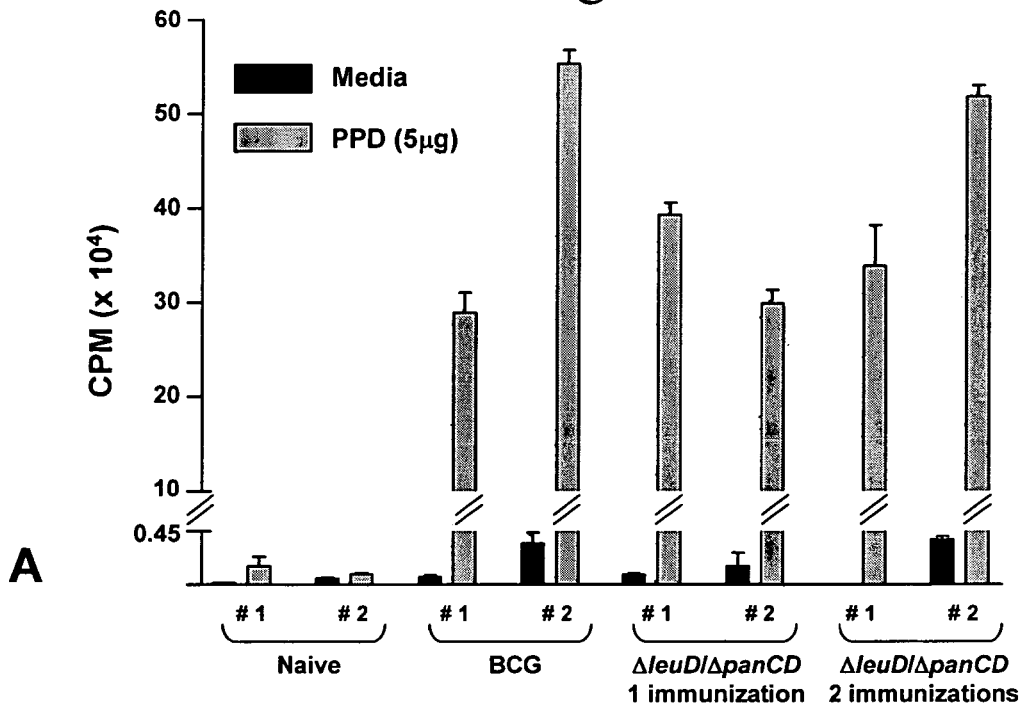
Figure 21:
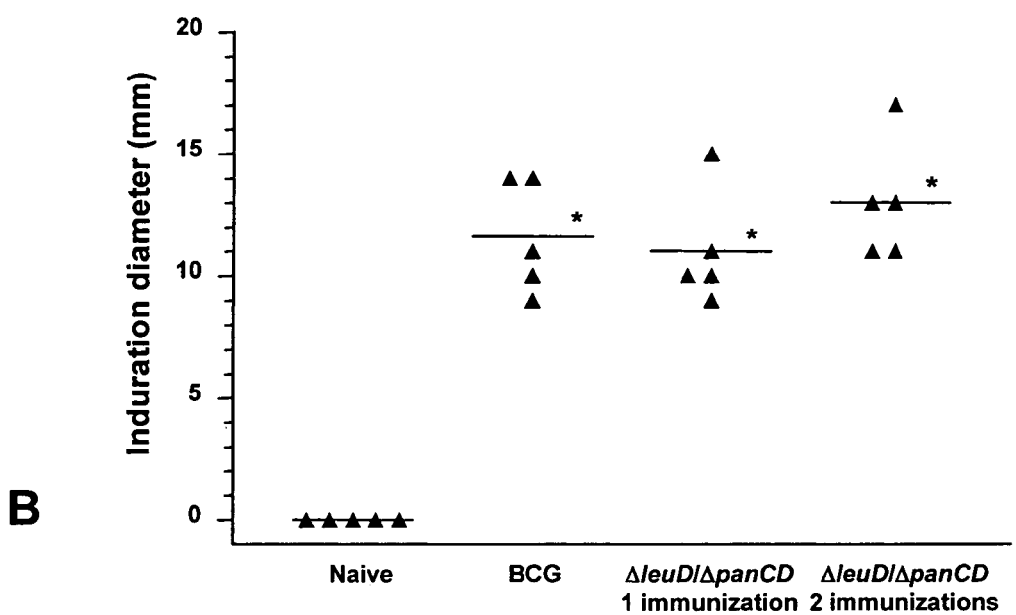
Figure 22:
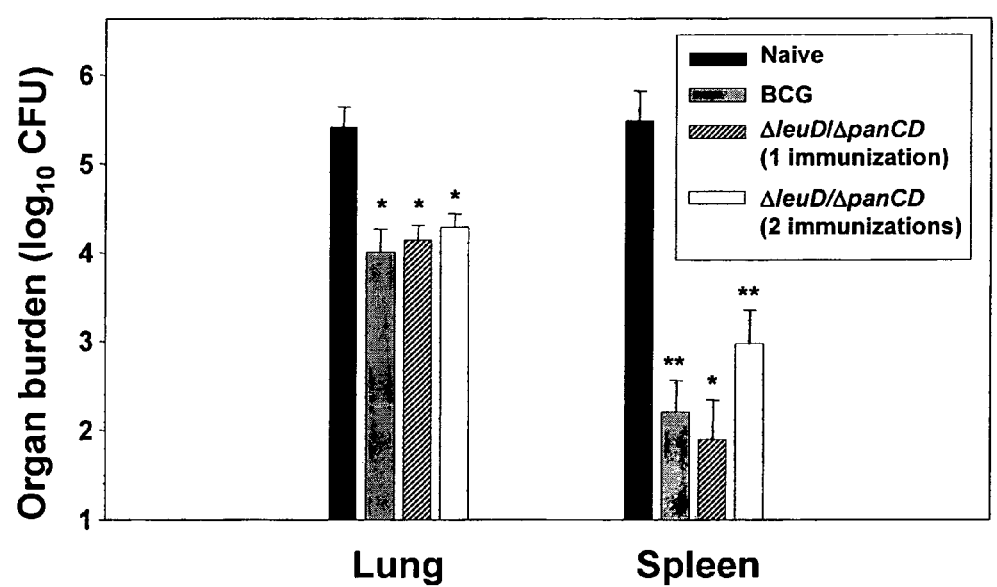
Figure 23:
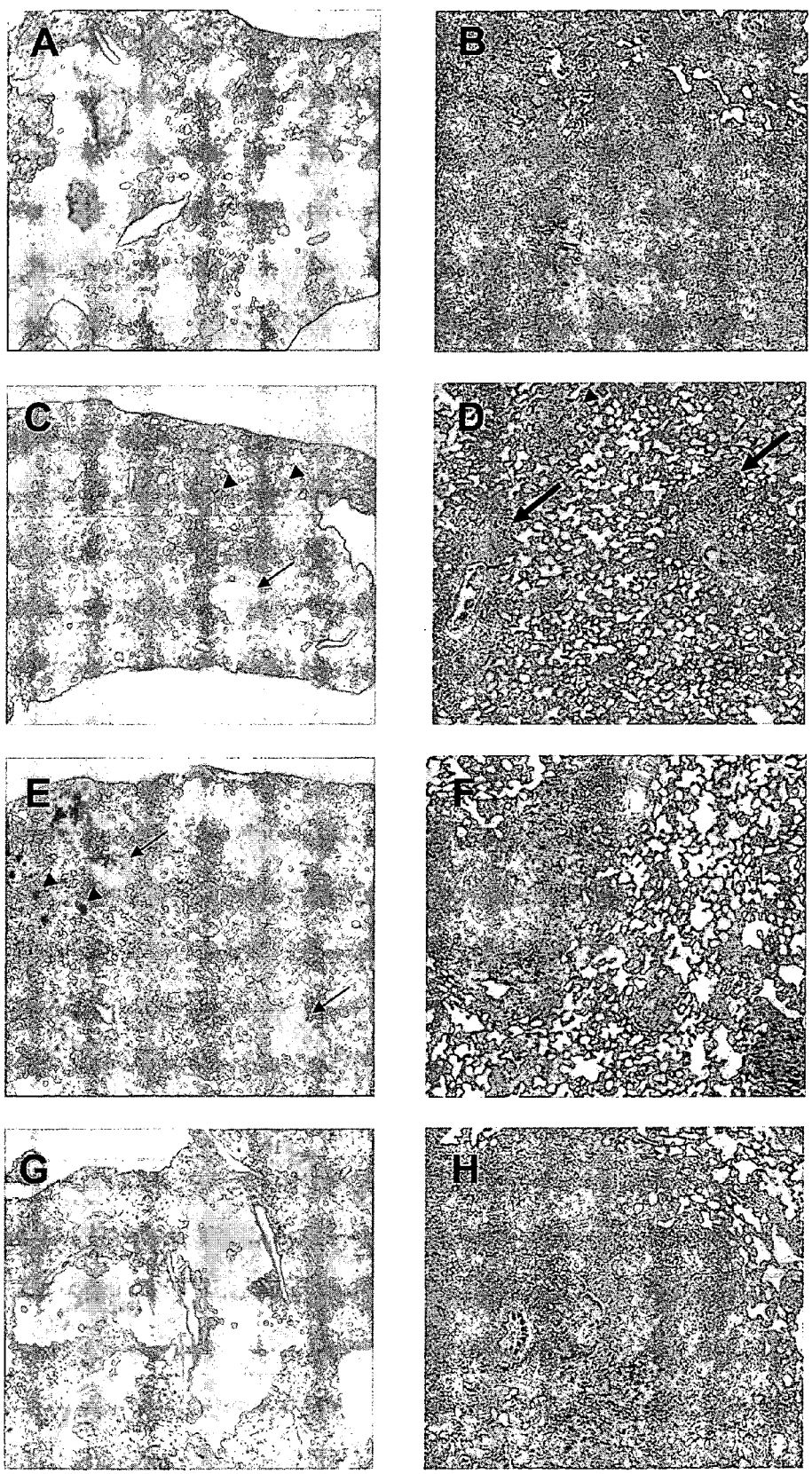

SCID mice infected with 1×10$^2$ CFU H137Rv succumbed to infection in 6 weeks, whereas the mice infected with 1×10$^6$ mc$^2$6030 survived significantly longer with more than 75% of mice surviving for more than 300 days (FIG. 17A). Bacteria isolated from mc$^2$6030-infected mice before they died were all auxotrophs, confirming that there were no revertants under in vivo conditions. In order to assess the safety of mc$^2$6030 in immunocompetent BALB/c mice, we infected mice intravenously with 1×10$^6$ mc$^2$6030 or 1×10$^6$ of wild-type H37Rv. All mice infected with H37Rv succumbed to infection by 150 days, whereas mice infected with mc$^2$6030 survived for more than 300 days (FIG. 17B). In an effort to understand the role of immune responses in controlling infection with the pantothenate mutants, we infected immunocompetent C57B1/6 with 1×10$^6$ CFU of mc$^2$6001 (ΔRD1), mc$^2$6004 (complementing strain), mc$^2$6030 (ΔRD1ΔpanCD) or wild-type H37Rv. Mice infected with H37Rv and mc$^2$6004 showed progressive growth in all the three organs, whereas mice infected with mc$^2$6030 showed a drop in growth during the first 3 weeks in the lungs and spleen (FIG. 18). Following 3 weeks of infection, the growth pattern of both mc$^2$6001 and mc$^2$6030 were identical in the spleen and lungs. Mice immunized subcutaneously with one or two doses of mc$^2$6030 demonstrated protection against aerosol challenge with virulent *M. tuberculosis*, which was comparable to the protection afforded by BCG vaccination (Table 6). No pantothenate auxotrophs were recovered from spleen or lungs of mice at 1, 2 or 3 months following subcutaneous immunization.

TABLE 6

Bacterial burden of virulent *M. tuberculosis* in uninoculated mice and mice inoculated with BCG or one or two doses of ΔRD1ΔpanCD.

| Experimental Group | Lung CFUs ($log_{10}$) | Spleen CFUs (log10) |
|---|---|---|
| Naive | 5.99 ± 0.09 | 4.94 ± 0.06 |
| ΔRD1ΔpanCD (1 dose) sc | 5.22 ± 0.10* | 4.04 ± 0.15* |
| ΔRD1ΔpanCD (2 doses) sc | 4.86 ± 0.14** | 3.58 ± 0.11** |
| BCG (1 dose) sc | 4.79 ± 0.19** | 3.73 ± 0.27** |

*$p < 0.01$ relative to controls;
**$p < 0.001$ relative to controls

Construction and characterization of *M. tuberculosis* ΔlysAΔpanCD ($mc^2$6020). A pantothenate auxotroph of *M. tuberculosis* ΔlysA was generated by specialized transduction and the strain designated $mc^2$6020. No CFU were detected on 7H11 when $5\times10^{10}$ CFU were plated, suggesting the reversion frequency to be below $10^{-11}$. This double mutant is auxotrophic for both lysine and pantothenate. SCID mice infected with $1\times10^2$ CFU H37Rv succumbed to infection in 6 weeks, whereas the mice infected with $1\times10^6$ $mc^2$6020 survived for more than 400 days with no mortality. In order to assess the safety and growth kinetics of $mc^2$6020 in immunocompetent BALB/c mice, we infected mice intravenously with $1\times10^6$ $mc^2$6020 or $1\times10^6$ of wild-type H37Rv. All mice infected with H37Rv succumbed to infection by 150 days, whereas mice infected with $mc^2$6020 survived for more than 400 days. After 3 weeks following intravenous infection, no colonies of $mc^2$6020 could be recovered from spleen, liver or lungs of infected mice. Interestingly, mice immunized subcutaneously with one or two doses of $mc^2$6020 demonstrated protection against aerosol challenge with virulent *M. tuberculosis*, which was comparable to the protection afforded by BCG vaccination (Table 7). No pantothenate and lysine requiring auxotrophs were recovered from spleen or lungs of mice at 1, 2 or 3 months following subcutaneous immunization. Other studies established that both $mc^2$6020 and $mc^2$6030 protects the a level of protection of mice against TB equivalent to the protection afforded by BCG (FIG. 19).

TABLE 7

Bacterial burden of virulent *M. tuberculosis* in uninoculated mice and mice inoculated with BCG or one or two doses of $mc^2$6020 (ΔlysAΔpanCD) sc or one dose of $mc^2$6020 iv.

| Experimental group | Lung CFUs ($log_{10}$) | Spleen CFUs ($log_{10}$) |
|---|---|---|
| naive | 6.03 ± 0.05[a] | 4.84 ± 0.27 |
| BCG (1 dose) sc | 4.76 ± 0.19*** | 3.95 ± 0.18* |
| $mc^2$6020 (1 dose) sc | 5.05 ± 0.06*** | 4.02 ± 0.11* |
| $mc^2$6020 (2 doses) sc | 5.09 ± 0.05*** | 4.06 ± 0.27 |
| $mc^2$6020 (1 dose) iv | 5.06 ± 0.11*** | 4.00 ± 0.15* |

[a]Mean ± SEM
$p < 0.001$ =***;
$p < 0.05$ =*

These data clearly demonstrate the safety and immunogenicity of these two double mutants of *M. tuberculosis* in mice.

The double deletion mutant $mc^2$6030 (ΔRD1ΔpanCD) immunizes and protects SCID mice from aerosolized *M. tuberculosis* challenge. The double deletion mutants were safer than BCG in SCID mice, where all of the SCID mice died before 100 days when inoculated with BCG, 100% and 25% of the mice survived inoculation with $mc^2$6020 and $mc^2$6030, respectively (FIG. 20).

EXAMPLE 7

Protection Elicited by a Double Leucine and Pantothenate Auxotroph of *Mycobacterium Tuberculosis* in Guinea Pigs Example Summary.

We have developed a live, fully attenuated *Mycobacterium tuberculosis* vaccine candidate strain with two independent attenuating auxotrophic mutations in leucine and pantothenate biosynthesis. The ΔleuD/ΔpanCD double auxotroph is fully attenuated in the SCID mouse model, and highly immunogenic and protective in the extremely sensitive guinea pig tuberculosis model, reducing both bacterial burden and disease pathology.

This example is published as Sampson et al., 2004.

The rising worldwide incidence of tuberculosis (TB) caused by *Mycobacterium tuberculosis* (MTB) infection, coupled with the concurrent HIV/AIDS epidemic, has created the need for improved TB therapies and a more effective preventative vaccine. The effectiveness of the currently available vaccine, Bacille Calmette-Guèrin (BCG), derived by many passages from a *Mycobacterium bovis* isolate, has varied enormously in different parts of the world. Furthermore, BCG vaccination has not provided adequate protection against pulmonary disease in adults (Baily, 1980). The reasons for the variability in efficacy of BCG remain unresolved (Bloom and Fine, 1994). Exposure to environmental mycobacteria may provide some protection against MTB, thereby masking the effects of BCG immunization, or alternatively interfere with the initial replication of the BCG vaccine strain (Brandt et al., 2000; Hernandez-Pando et al., 1997; Palmer and Long, 1966). Another reason that BCG may not be optimally protective is that it known to lack between 100 and 150 genes that are present in the *M. tuberculosis* genome (Behr et al., 1999), some of which encode immunologically important antigens (Behr and Small, 1997; Behr er al., 1999), including ESAT-6 (Harboe et al., 1996), a protein that has been identified as a protective antigen in various animal immunization studies (Baldwin et al., 1998; Brandt et al., 2000; Pym et al., 2003; Skinner et al., 2003). In considering vaccine development, it is important to bear in mind that the target population in the developing world will certainly include immunocompromised individuals infected with HIV, for whom even a live attenuated vaccine such as BCG presents a risk. Since the HIV-infected population is particularly vulnerable to mycobacterial disease (Dye et al., 1999), it is critical that any novel TB vaccine demonstrate safety in the setting of compromised immunity and previous MTB exposure. Importantly, BCG immunization has been reported to be harmful in immunocompromised individuals, and a number of cases of disseminated BCG infection in HIV-positive children and adults have been documented (Armbruster et al., 1990; Besnard et al., 1993; Houde and Dery, 1988; O'Brien et al., 1995; Reynes et al., 1989; Talbot et al., 1997).

Figure 24:
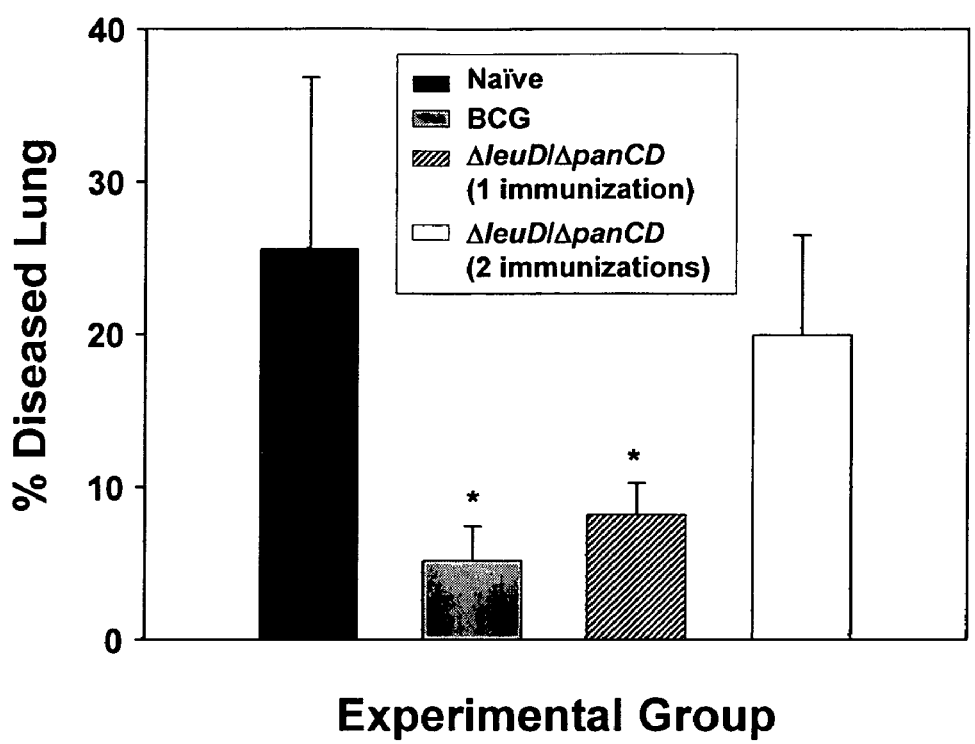
Figure 25:
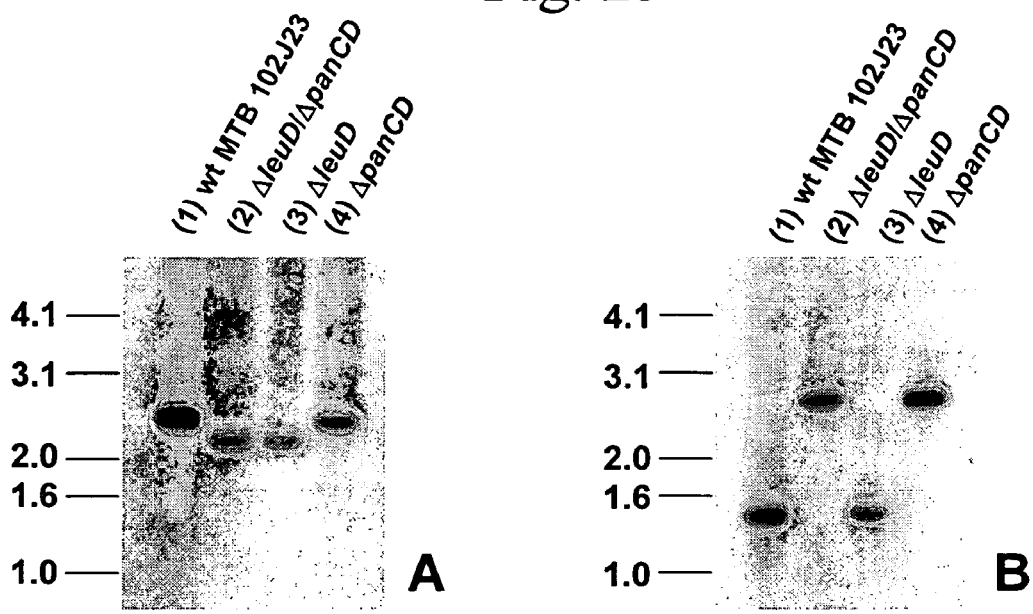
Figure 26:
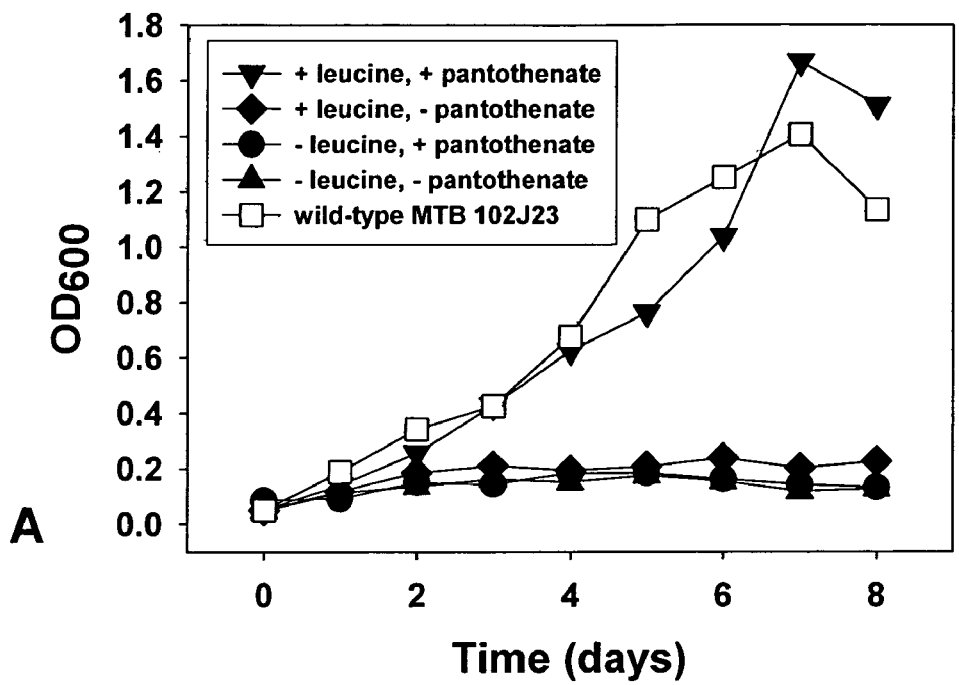
Figure 26:
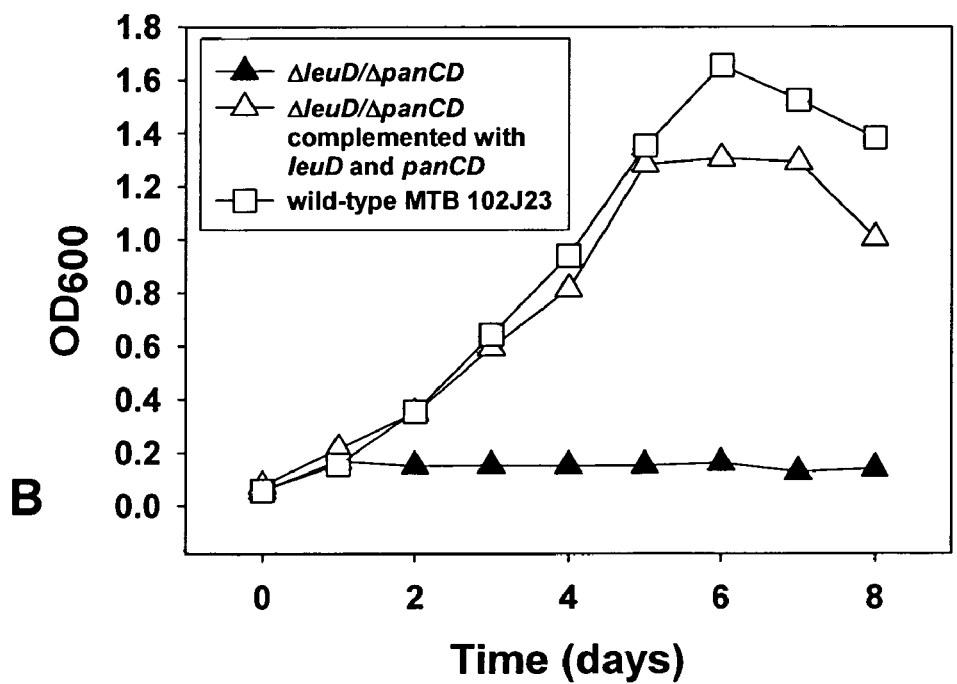
Figure 27:
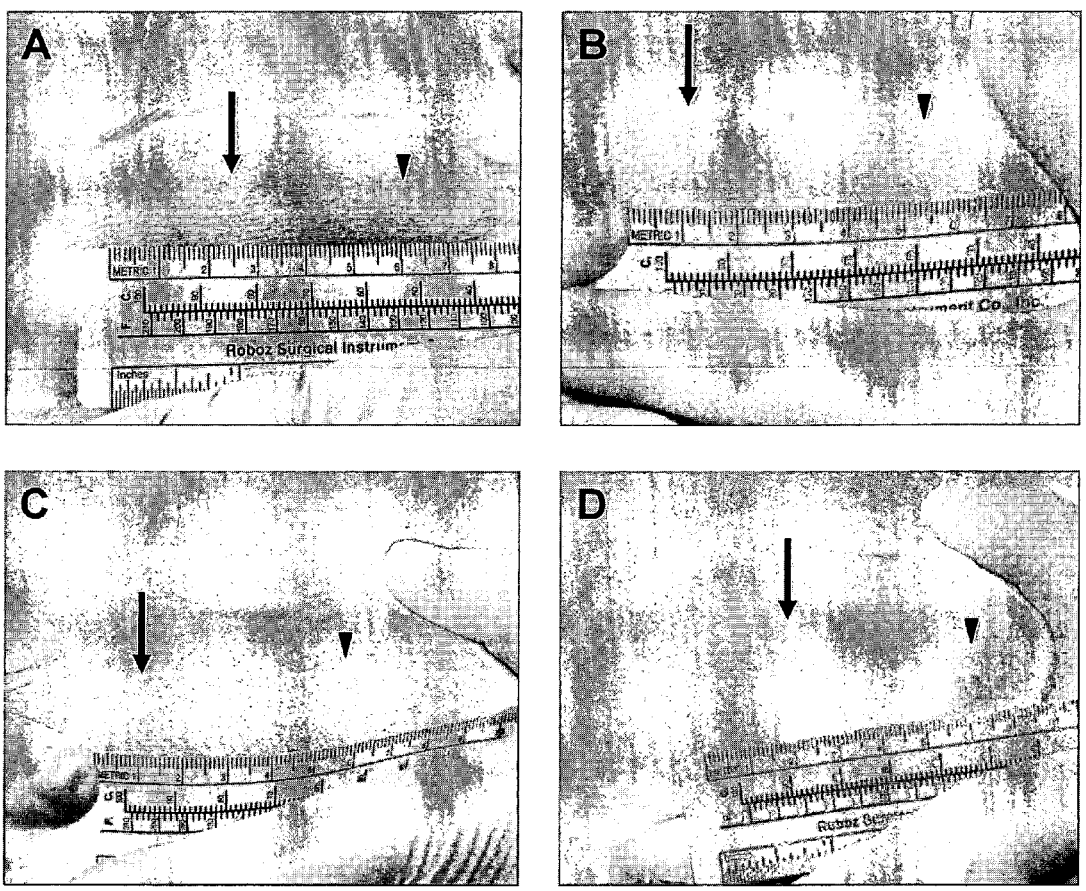

Of the several approaches being applied to the development of new TB vaccines (Young, 2003), we have used strategies to create live, non-replicating attenuated strains of MTB. The advantage of this approach has been demonstrated by evidence that live vaccines are usually able to elicit a superior, longer-term memory immune response than non-living vaccines (Opie and Freund, 1937; Smith, 1917). In addition, vaccines derived from MTB, which includes more than 100 genes deleted from BCG, express more MTB-specific antigens. Previously, we demonstrated the feasibility of this approach by the creation of independent leucine and pantothenate auxotrophic mutants that elicited protective immunity in a murine model of MTB infection (Hondalus et al., 2000; Sambandaburthy et al., 2002). Importantly, we showed that leucine auxotrophy alone rendered MTB incapable of replicating in macrophages in vitro, and furthermore we observed no increase in bacterial numbers over time in the organs of immunocompetent and immunocompromised SCID mice challenged with the MTB leucine auxotroph (Hondalus et al., 2000; unpublished). The apparent lack of in vivo replication associated with leucine auxotrophy seemingly indicates that host leucine is inaccessible to the MTB mutant, thus impairing its ability to replicate in the host. In this study, we now describe the combination of two independent, attenuating, non-revertible mutations, with deletions in the essential leuD (Rv2987c) and panCD (Rv3602c and Rv3601c) loci in MTB, creating a strain that is highly attenuated in vivo, and auxotrophic for both leucine and pantothenate. The rationale for combining two mutations was to ensure the safety of the strain, in the unlikely occurrence of a second site suppressor mutation or a recombination event leading to loss of auxotrophy at one or other of the loci. In order to facilitate downstream development and testing of the double auxotroph as a potential vaccine candidate, additional in vitro and in vivo safety aspects were addressed. Finally, we chose to test the immunogenic and protective capacities of this strain in the highly susceptible guinea pig model, in which a very few bacilli represent a lethal dose (McMurray, 1994).

Results

Construction of ΔleuD/ΔpanCD double auxotroph of *M. tuberculosis* H37Rv. For reasons of safety and in consideration of future clinical vaccine development, the ΔleuD/ΔpanCD mutant was created using good laboratory practice for documentation of step-wise attenuation of the parent strain *M. tuberculosis* H37Rv 102J23. This parent strain (obtained from Frank Collins, formerly of the FDA, Rockville, Md.) had not been previously cultured in medium containing bovine serum albumin. All subsequent culture steps were performed with documented lots of OADC (Becton, Dickinson and Company, Sparks, Md.), so that the country of origin for the bovine-derived components could be established to exclude the possibility of contamination with Bovine Spongiform Encephalopathy (BSE) prions. The first step in the construction of the double auxotroph was to generate an unmarked leuD deletion mutant using a suicide vector approach similar to that which we previously described (Pavelka and Jacobs, 1999). Subsequently, the panCD locus in the ΔleuD strain was deleted and marked with a hygromycin resistance ($hyg^R$) cassette by using specialized phage transduction (Sambandamurthy et al., 2002). Southern blot and PCR analysis confirmed that the final strain had undergone allelic replacement at the leuD and panCD loci (FIG. 25), removing 359 bp of leuD and 1298 bp of panCD.

As predicted, the ΔleuD/ΔpanCD strain failed to grow on minimal media (7H9, 10% OADC, 0.2% glycerol, 0.05% Tween 80), or when singly supplemented with either leucine (50 μg/ml) or pantothenate (24 μg/ml). Growth could only be restored in the presence of both leucine and pantothenate (FIG. 26) confirming that the strain was auxotrophic for these two compounds. The growth rate of ΔleuD/ΔpanCD in minimal medium supplemented with both leucine and pantothenate was similar to that of wild-type MTB in minimal medium (FIG. 25). The ΔleuD/ΔpanCD strain was complemented with both leuD and panCD (under the control of the mycobacterial hsp60 promoter) in single copy integrated at the att site, abrogating the requirement for exogenous leucine and pantothenate, and confirming that the observed auxotrophy was due solely to the mutation of these two loci.

Because further development of the ΔleuD/ΔpanCD strain as a potential vaccine candidate would require large-scale GMP production, involving serial passage in vitro, we conducted studies to determine the stability of the strain during in vitro growth. Reversion analysis was performed on 3 separate occasions. The ΔleuD/ΔpanCD strain was cultured in broth medium supplemented with both leucine and pantothenate, but without hygromycin; and then plated onto 7H10 agar (with 10% OADC, 0.2% glycerol, 100 μg/ml cycloheximide) containing either pantothenate alone or leucine alone. No prototrophic clones (out of $2\times10^9$; $2\times10^{10}$ and $2\times10^{10}$ CFU plated for experiments 1, 2, and 3, respectively) were identified, establishing the reversion frequency as $<10^{-11}$. Similarly, no reversion was observed after repeated in vitro subculturing of the strain. After 6 in vitro passages, representing approximately 41 doublings, no prototrophic clones arose out of a final $3\times10^{10}$ CFU plated, further demonstrating that the auxotrophic phenotype of the strain is stable and does not revert to prototrophy during repeated in vitro passage.

To ensure that the inclusion of a $hyg^R$ marker in the strain did not influence susceptibility to commonly used anti-tuberculous agents, the ΔleuD/ΔpanCD strain was tested for sensitivity to the following antibiotics: ethambutol (2.5 μg/ml), isoniazid (0.1 and 0.4 μg/ml), pyrazinamide (100 μg/ml), rifampin (2.0 μg/ml) and streptomycin (2.0 μg/ml) (Focus Technologies Microbiology laboratories, Cypress, Calif.). The strain was fully sensitive to all five antibiotics tested.

ΔleuD/ΔpanCD is attenuated in immunocompromised SCID mice. A critical property of a live MTB vaccine strain is that it be fully attenuated even in immunocompromised hosts. This is particularly relevant in consideration of the worldwide HIV epidemic, in which immunocompromised individuals represent an important potential target population for any new TB vaccine candidate (Dye et al., 1999). Previously, we found that the individual auxotrophic strains were highly attenuated in vivo (Hondalus et al., 2000; Sambandamurthy et al., 2002), therefore the double auxotroph would also be expected to be fully attenuated. To confirm this, the in vivo attenuation of ΔleuD/ΔpanCD was assessed by infection of immunocompromised BALB/cJ SCID mice, which lack T- and B-cells. Mice were obtained from Jackson Laboratories (Bar Harbor, Me.), and housed according to institutional protocols. BALB/cJ SCID mice are highly susceptible to MTB infection, and succumb to intravenous challenge with $7\times10^3$ CFU wild-type MTB H37Rv in approximately 4 weeks (mean survival time (MST)=31 days)(FIG. 27). However, SCID mice challenged with ΔleuD/ΔpanCD at 4 times the wild-type challenge dose ($3\times10^4$ CFU) were able to clear the infection and have remained healthy for >41 weeks (FIG. 27). This demonstrates that the ΔleuD/ΔpanCD strain is attenuated even in a severely immunocompromised host, which succumbs to BCG challenge (Guleria et al., 1996). Furthermore, infection of SCID mice with a doubly complemented ΔleuD/ΔpanCD strain (both the leuD and panCD loci) resulted in a similar rate of mortality to wild-type infected animals, (MST=40 days) (FIG. 27), thereby confirming that the observed attenuation of the double auxotroph was due to the mutations in the leuD and panCD loci, and not to polar effects on adjacent genes.

Immunogenicity and protective efficacy in guinea pigs. Previous investigations of the vaccine potential of the individual leucine and pantothenate auxotrophs suggested that these strains were able to elicit protection against challenge with virulent *M. tuberculosis*, in the murine model (Hondalus et al., 2000; Sambandamurthy et al., 2002). Both strains reduced lung pathology and increased survival times of infected animals. However, the mouse is relatively resistant to MTB infection, in contrast to the far more susceptible guinea pig (McMurray, 1994; Riley et al., 1959). Therefore, we chose to test the immunizing and protective capacity of the double auxotroph in the more rigorous and highly susceptible guinea pig aerosol TB challenge model.

Previous data had shown that the single ΔleuD auxotroph apparently does not replicate in vivo and is cleared from lung, liver and spleens of immunocompetent BALB/cJ mice within 13 weeks (Hondalus et al., 2000). As this relatively rapid clearance might limit the quantity of antigen available for immune priming, we also included a ΔleuD/ΔpanCD primed and boosted group in the experimental design, in an attempt to achieve more prolonged immunization. Female Hartley guinea pigs (300 g-400 g) (Elm Hill Breeders, Chelmsford, Mass.) were housed according to institutional protocols. One group of animals was immunized intradermally (i.d.) with ΔleuD/ΔpanCD, followed six weeks later by a second immunization with ΔleuD/ΔpanCD. At this time, a second group of animals received a single immunization with ΔleuD/ΔpanCD, and a third group received *M. bovis* BCG (Pasteur) (BCG-P), for comparison to the currently available *M. tuberculosis* vaccine. An unimmunized group was included as a negative control.

To confirm that the highly attenuated ΔleuD/ΔpanCD strain was able to elicit a specific immune response to mycobacterial antigens, T-cell proliferative responses of the vaccinated guinea pigs to PPD were measured in vitro. Five weeks after the last immunization, PBMCs were collected via cardiac puncture from 2 animals in each group and cultured with 5 μg of PPD/well (Mycos Research, LLC, Loveland, Colo.), then pulsed with [$^3$H]-thymidine to assay specific proliferative responses to *M. tuberculosis* antigens. PBMCs from unimmunized guinea pigs did not proliferate in response to PPD, whereas those from ΔleuD/ΔpanCD-immunized animals showed proliferative responses comparable to BCG-P-immunized animals (FIG. 21A). Both singly immunized and boosted animals exhibited similar responses. Next, we assessed the cutaneous delayed-type hypersensitivity (DTH) response to PPD in all groups. At 7 weeks post final immunization, guinea pigs were intradermally tested with 4 and 40 tuberculin units (TU) (FIGS. 21B and 28) of PPD (FDA/CBER, Bethesda, Md.), followed by measurement of the diameter of induration 24 hours later. As illustrated in FIG. 22B, ΔleuD/ΔpanCD-immunization induced statistically equivalent DTH responses when compared to immunization with viable BCG-P (FIG. 21B). These data demonstrate that despite its apparent inability to replicate, the double auxotroph is able to induce robust cell-mediated immune responses following immunization.

Having established that the attenuated ΔleuD/ΔpanCD auxotroph elicited strong cellular immune responses in vivo, we investigated whether this translated into protection against challenge with virulent *M. tuberculosis*. Therefore, the unimmunized control group and the ΔleuD/ΔpanCD- and BCG-P-vaccinated groups were challenged at seven weeks after the last immunization by aerosol with 20 CFU of *M. tuberculosis* H37Rv per animal. At 5 weeks post-challenge, right caudal lung and spleen bacterial burdens were determined by dilution plating of organ homogenates. Plates contained 2 μg/ml of thiophene-2-carboxylic acid hydrazide (Sigma), to prevent growth of any residual BCG-P. Guinea pigs immunized with ΔleuD/ΔpanCD (either once or twice) showed statistically significant reductions in both lung (1 log) and spleen (2-3 logs) bacterial burdens relative to naive controls. The protection afforded by single or double immunization with ΔleuD/ΔpanCD was statistically equivalent to that provided by BCG-P (FIG. 22). Splenic burden following aerosol challenge is an indication of hematogenous dissemination of the infection and it is particularly noteworthy that a single immunization with the double auxotroph protected well against dissemination. In fact, in 3 of 5 animals receiving a single immunization with ΔleuD/ΔpanCD, no bacteria could be detected in the spleen (limit of detection, 50 CFU). Boosting with ΔleuD/ΔpanCD did not appear to enhance the protective effect.

Assessment of protective efficacy of ΔleuD/ΔpanCD vaccination by lung histopathology evaluation. Although guinea pig infection has many desirable features as a model for TB, the financial expense and space constraints associated with experiments in this species often preclude long-term survival studies in this model. It has been suggested that bacillary burden at early time points may not necessarily correlate with survival; rather pulmonary pathology may be a better predictor of long-term disease outcome following MTB infection (Baldwin et al. 1998). Histological evaluation of the lungs from guinea pigs in this study demonstrated that both BCG-P immunization and a single immunization with the ΔleuD/ΔpanCD auxotroph caused significant reduction in severity of lung damage following aerosol infection with a virulent strain of MTB. Whereas the unvaccinated guinea pigs developed severe pneumonia with extensive widespread coalescing granulomas and severe caseation necrosis (FIGS. 23A and B), BCG-P vaccinated animals developed milder, focal, localized granulomas and perivascular lymphocytic accumulations dispersed throughout the lung (FIGS. 23C and D). The guinea pigs vaccinated once i.d. with the ΔleuD/ΔpanCD double auxotrophic strain showed multiple scattered peribronchial, well-defined, fewer and smaller granulomas, reduced in severity compared to the unvaccinated group (FIGS. 23E and F). However, guinea pigs boosted with the ΔleuD/ΔpanCD double auxotroph developed more extensive granulomatous pneumonia compared to the guinea pigs given either BCG or a single dose of the ΔleuD/ΔpanCD strain (FIGS. 23G and H). The booster immunization offered no advantage; and the pulmonary pathology appeared to be more severe compared to a single immunization. In summary, a single immunization with the live-attenuated ΔleuD/ΔpanCD MTB auxotrophic vaccine strain induced protection in the susceptible guinea pig tuberculosis model comparable to that provided by BCG.

To semi-quantitatively evaluate the extent of lung pathology, morphometric analysis was performed (FIG. 24) using Scion Imaging Software (Scion Corporation, Frederick, MD) (Dascher et al., 2003) to measure the area of the lung inflammation as a percentage of the total lung area. The BCG-P and singly immunized ΔleuD/ΔpanCD groups showed statistically significant and equivalent reductions in the extent of lung damage compared to unvaccinated animals after challenge (FIG. 24). However, the lung pathology was exacerbated in the boostered group (FIG. 24). This observation is consistent with other recent studies (Moreira et al., 2002; Tayler et al., 1997; Turner et al., 2000). For example, it has been reported that existing MTB infection in mice was worsened by the delivery of additional mycobacterial antigens administered either subcutaneously or by aerosol in the form of viable or heat killed BCG and MTB (Moreira et al., 2002). The mechanism proposed to explain these findings is that, analogous to the well-known Koch phenomenon (Koch, 1891), the increased load of mycobacterial antigen induced a stronger inflammatory response and a worsening of lung pathology (Moreira et al., 2002). This may explain the more severe lung pathology associated with the booster dose as reported here. These observations could have important implications for the design and implementation of any future TB vaccines. It will be important to know whether prior BCG immunization or subclinical infection would result in similar adverse inflammatory responses if such an individual were boosted with the new vaccine, and whether adverse reactions could be avoided by adjusting the timing and or dose of the prime-boost strategy.

In summary, our work describes the development of a live *M. tuberculosis* vaccine candidate with two attenuating auxotrophic mutations. This strain is fully attenuated and yet retains immunogenicity and protective capacity in a sensitive guinea pig tuberculosis aerosol challenge model. We have taken into consideration certain regulatory issues in the hope of facilitating subsequent development of the vaccine for human clinical trials. The ΔleuD/ΔpanCD strain is safe even in severely immunocompromised (SCID) mice. Importantly, although the ΔleuD/ΔpanCD strain is apparently non-replicating, and is fully attenuated in contrast with live BCG, the two vaccines elicited equivalent protection. In the case of the double auxotroph, since the protection achieved is independent of bacterial replication, this vaccine may have the advantage of greater safety in the context of target populations with high prevalence of HIV infection, high exposure to environmental mycobacteria or prior BCG vaccination. Importantly, recent data demonstrate that long-term protection in mice can be achieved by immunization with a related double auxotroph of MTB (Sambandamurthy et al., 2005). We believe these data justify further development and testing of the ΔleuD/ΔpanCD double auxotroph as a vaccine candidate against tuberculosis.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

SEQ ID Nos

SEQ ID NO:1—An RD1 region of *Mycobacterium tuberculosis* H37Rv. Bases 4350263-4359716 of the genome of *M. tuberculosis* H37Rv, as provided in GenBank Accession No. NC000962.

```
4350263 gatcgtgg gtgccgccgg ggggatgccg ccgatggcac
4350301 cgctggcccc gttattgccg gcggcggcag atatcgggtt gcacatcatt gtcacctgtc
4350361 agatgagcca ggcttacaag gcaaccatgg acaagttcgt cggcgccgca ttcgggtcgg
4350421 gcgctccgac aatgttcctt tcgggcgaga agcaggaatt cccatccagt gagttcaagg
4350481 tcaagcggcg ccccctggc caggcatttc tcgtctcgcc agacggcaaa gaggtcatcc
4350541 aggcccccta catcgagcct ccagaagaag tgttcgcagc acccccaagc gccggttaag
4350601 attatttcat tgccggtgta gcaggacccg agctcagccc ggtaatcgag ttcgggcaat
4350661 gctgaccatc gggtttgttt ccggctataa ccgaacggtt tgtgtacggg atacaaatac
4350721 agggagggaa gaagtaggca aatggaaaaa atgtcacatg atccgatcgc tgccgacatt
4350781 ggcacgcaag tgagcgacaa cgctctgcac ggcgtgacgg ccggctcgac ggcgctgacg
4350841 tcggtgaccg ggctggttcc cgcgggggcc gatgaggtct ccgcccaagc ggcgacggcg
4350901 ttcacatcgg agggcatcca attgctggct tccaatgcat cggcccaaga ccagctccac
4350961 cgtgcgggcg aagcggtcca ggacgtcgcc cgcacctatt cgcaaatcga cgacggcgcc
4351021 gccggcgtct tcgccgaata ggcccccaac acatcggagg gagtgatcac catgctgtgg
4351081 cacgcaatgc caccggagct aaataccgca cggctgatgg ccggcgcggg tccggctcca
4351141 atgcttgcgg cggccgcggg atggcagacg ctttcggcgg ctctggacgc tcaggccgtc
4351201 gagttgaccg cgcgcctgaa ctctctggga gaagcctgga ctggaggtgg cagcgacaag
```

-continued

```
4351261  gcgcttgcgg ctgcaacgcc gatggtggtc tggctacaaa ccgcgtcaac acaggccaag
4351321  acccgtgcga tgcaggcgac ggcgcaagcc gcggcataca cccaggccat ggccacgacg
4351381  ccgtcgctgc cggagatcgc cgccaaccac atcacccagg ccgtccttac ggccaccaac
4351441  ttcttcggta tcaacacgat cccgatcgcg ttgaccgaga tggattattt catccgtatg
4351501  tggaaccagg cagccctggc aatggaggtc taccaggccg agaccgcggt taacacgctt
4351561  ttcgagaagc tcgagccgat ggcgtcgatc cttgatcccg cgcgagcca gagcacgacg
4351621  aacccgatct cggaatgcc ctcccctggc agctcaacac cggttggcca gttgccgccg
4351681  gcggctaccc agaccctcgg ccaactgggt gagatgagcg cccgatgca gcagctgacc
4351741  cagccgctgc agcaggtgac gtcgttgttc agccaggtgg gcggcaccgg cggcggcaac
4351801  ccagccgacg aggaagccgc gcagatgggc ctgctcggca ccagtccgct gtcgaaccat
4351861  ccgctggctg gtggatcagg ccccagcgcg ggcgcgggcc tgctgcgcgc ggagtcgcta
4351921  cctggcgcag gtgggtcgtt gacccgcacg ccgctgatgt ctcagctgat cgaaaagccg
4351981  gttgccccct cggtgatgcc ggcggctgct gccggatcgt cggcgacggg tggcgccgct
4352041  ccggtgggtg cgggagcgat gggccagggt gcgcaatccg gcggctccac caggccgggt
4352101  ctggtcgcgc cggcaccgct cgcgcaggag cgtgaagaag acgacgagga cgactgggac
4352161  gaagaggacg actggtgagc tcccgtaatg acaacagact ccccggccac ccgggccgga
4352221  agacttgcca acattttggc gaggaaggta aagagagaaa gtagtccagc atggcagaga
4352281  tgaagaccga tgccgctacc ctcgcgcagg aggcaggtaa tttcgagcgg atctccggcg
4352341  acctgaaaac ccagatcgac caggtggagt cgacggcagg ttcgttgcag gccagtggc
4352401  gcggcgcggc ggggacggcc gcccaggccg cggtggtgcg cttccaagaa gcagccaata
4352461  agcagaagca ggaactcgac gagatctcga cgaatattcg tcaggccggc gtccaatact
4352521  cgagggccga cgaggagcag cagcaggcgc tgtcctcgca aatgggcttc tgacccgcta
4359581  aaacggagca aaaacatgac agagcagcag tggaatttcg cgggtatcga
4352641  ggccgcggca agcgcaatcc agggaaatgt cacgtccatt cattccctcc ttgacgaggg
4352701  gaagcagtcc ctgaccaagc tcgcagcggc ctggggcggt agcggttcgg aggcgtacca
4352761  gggtgtccag caaaaatggg acgccacggc taccgagctg aacaacgcgc tgcagaacct
4352821  ggcgcggacg atcagcgaag ccggtcaggc aatggcttcg accgaaggca acgtcactgg
4352881  gatgttcgca tagggcaacg ccgagttcgc gtagaattgc gaaacacggg atcgggcgag
4352941  ttcgaccttc cgtcggtctc gcccttttctc gtgtttatac gtttgagcgc actctgagag
4353001  gttgtcatgg cggccgacta cgacaagctc ttccggccgc acgaaggtat ggaagctccg
4353061  gacgatatgg cagcgcagcc gttcttcgac cccagtgctt cgtttccgcc ggcgcccgca
4353121  tcggcaaacc taccgaagcc caacggccag actccgcccc cgacgtccga cgacctgtcg
4353181  gagcggttcg tgtcggcccc gccgccgcca cccccacccc cacctccgcc tccgccaact
4353241  ccgatgccga tcgccgcagg agagccgccc tcgccggaac cggccgcatc taaaccaccc
4353301  acacccccca tgcccatcgc cggacccgaa ccggccccac ccaaaccacc cacaccccc
4353361  atgcccatcg ccggacccga accggcccca cccaaaccac ccacacctcc gatgcccatc
4353421  gccggacctg cacccacccc aaccgaatcc cagttggcgc ccccccagacc acgacacca
4353481  caaacgccaa ccggagcgcc gcagcaaccg gaatcaccgg cgccccacgt accctcgcac
4353541  gggccacatc aacccggcg caccgcacca gcaccgccct gggcaaagat gccaatcggc
4353601  gaaccccgc ccgctccgtc cagaccgtct gcgtccccgg ccgaaccacc gacccggcct
```

```
4353661 gcccccccaac actcccgacg tgcgcgccgg ggtcaccgct atcgcacaga caccgaacga
4353721 aacgtcggga aggtagcaac tggtccatcc atccaggcgc ggctgcgggc agaggaagca
4353781 tccggcgcgc agctcgcccc cggaacggag ccctcgccag cgccgttggg ccaaccgaga
4353841 tcgtatctgg ctccgccccac ccgccccgcg ccgacagaac ctccccccag cccctcgccg
4353901 cagcgcaact ccggtcggcg tgccgagcga cgcgtccacc ccgatttagc cgcccaacat
4353961 gccgcggcgc aacctgattc aattacggcc gcaaccactg gcggtcgtcc ccgcaagcgt
4354021 gcagcgccgg atctcgacgc gacacagaaa tccttaaggc cggcggccaa ggggccgaag
4354081 gtgaagaagg tgaagcccca gaaaccgaag gccacgaagc cgcccaaagt ggtgtcgcag
4354141 cgcggctggc gacattgggt gcatgcgttg acgcgaatca acctgggcct gtcacccgac
4354201 gagaagtacg agctggacct gcacgctcga gtccgccgca atccccgcgg gtcgtatcag
4354261 atcgccgtcg tcggtctcaa aggtggggct ggcaaaacca cgctgacagc agcgttgggg
4354321 tcgacgttgg ctcaggtgcg ggccgaccgg atcctggctc tagacgcgga tccaggcgcc
4354381 ggaaacctcg ccgatcgggt agggcgacaa tcgggcgcga ccatcgctga tgtgcttgca
4354441 gaaaaagagc tgtcgcacta caacgacatc cgcgcacaca ctagcgtcaa tgcggtcaat
4354501 ctggaagtgc tgccggcacc ggaatacagc tcggcgcagc gcgcgctcag cgacgccgac
4354561 tggcatttca tcgccgatcc tgcgtcgagg ttttacaacc tcgtcttggc tgattgtggg
4354621 gccggcttct tcgacccgct gacccgcggc gtgctgtcca cggtgtccgg tgtcgtggtc
4354681 gtggcaagtg tctcaatcga cggcgcacaa caggcgtcgg tcgcgttgga ctggttgcgc
4354741 aacaacggtt accaagattt ggcgagccgc gcatgcgtgg tcatcaatca catcatgccg
4354801 ggagaaccca atgtcgcagt taaagacctg gtgcggcatt tcgaacagca agttcaaccc
4354861 ggccgggtcg tggtcatgcc gtgggacagg cacattgcgg ccggaaccga gatttcactc
4354921 gacttgctcg accctatcta caagcgcaag gtcctcgaat tggccgcagc gctatccgac
4354981 gatttcgaga gggctggacg tcgttgagcg cacctgctgt tgctgctggt cctaccgccg
4355041 cggggggcaac cgctgcgcgg cctgccacca cccgggtgac gatcctgacc ggcagacgga
4355101 tgaccgattt ggtactgcca gcggcggtgc cgatggaaac ttatattgac gacaccgtcg
4355161 cggtgctttc cgaggtgttg aagacacgc cggctgatgt actcggcggc ttcgacttta
4355221 ccgcgcaagg cgtgtgggcg ttcgctcgtc ccggatcgcc gccgctgaag ctcgaccagt
4355281 cactcgatga cgccggggtg gtcgacgggt cactgctgac tctggtgtca gtcagtcgca
4355341 ccgagcgcta ccgaccgttg gtcgaggatg tcatcgacgc gatcgccgtg cttgacgagt
4355401 cacctgagtt cgaccgcacg gcattgaatc gctttgtggg ggcggcgatc ccgcttttga
4355461 ccgcgcccgt catcgggatg gcgatgcggg cgtggtggga aactgggcgt agcttgtggt
4355521 ggccgttggc gattggcatc ctggggatcg ctgtgctggt aggcagcttc gtcgcgaaca
4355581 ggttctacca gagcggccac ctggccgagt gcctactggt cacgacgtat ctgctgatcg
4355641 caaccgccgc agcgctggcc gtgccgttgc cgcgcggggt caactcgttg ggggcgccac
4355701 aagagccgg cgccgctacg gccgtgctgt ttttgacctt gatgacgcgg ggcggccctc
4355761 ggaagcgtca tgagttggcg tcgtttgccg tgatcaccgc tatcgcggtc atcgcggccg
4355821 ccgctgcctt cggctatgga taccaggact gggtccccgc gggggggatc gcattcgggc
4355881 tgttcattgt gacgaatgcg gccaagctga ccgtcgcggt cgcgcggatc gcgctgccgc
4355941 cgattccggt acccggcgaa accgtggaca acgaggagtt gctcgatccc gtcgcgaccc
4356001 cggaggctac cagcgaagaa accccgacct ggcaggccat catcgcgtcg gtgcccgcgt
```

-continued

```
4356061  ccgcggtccg gctcaccgag cgcagcaaac tggccaagca acttctgatc ggatacgtca
4356121  cgtcgggcac cctgattctg gctgccggtg ccatcgcggt cgtggtgcgc gggcacttct
4356181  ttgtacacag cctggtggtc gcgggtttga tcacgaccgt ctgcggattt cgctcgcggc
4356241  tttacgccga gcgctggtgt gcgtgggcgt tgctggcggc gacggtcgcg attccgacgg
4356301  gtctgacggc caaactcatc atctggtacc cgcactatgc ctggctgttg ttgagcgtct
4356361  acctcacggt agccctggtt gcgctcgtgg tggtcgggtc gatggctcac gtccggcgcg
4356421  tttcaccggt cgtaaaacga actctggaat tgatcgacgg cgccatgatc gctgccatca
4356481  ttcccatgct gctgtggatc accggggtgt acgacacggt ccgcaatatc cggttctgag
4356541  ccggatcggc tgattggcgg ttcctgacag aacatcgagg acacggcgca ggtttgcata
4356601  ccttcggcgc ccgacaaatt gctgcgattg agcgtgtggc gcgtccggta aaatttgctc
4356661  gatggggaac acgtatagga gatccggcaa tggctgaacc gttggccgtc gatcccaccg
4356721  gcttgagcgc agcggccgcg aaattggccg gcctcgtttt tccgcagcct ccggcgccga
4356781  tcgcggtcag cggaacggat tcggtggtag cagcaatcaa cgagaccatg ccaagcatcg
4356841  aatcgctggt cagtgacggg ctgcccggcg tgaaagccgc cctgactcga acagcatcca
4356901  acatgaacgc ggcggcggac gtctatgcga agaccgatca gtcactggga accagtttga
4356961  gccagtatgc attcggctcg tcgggcgaag gctggctgg cgtcgcctcg gtcggtggtc
4357021  agccaagtca ggctacccag ctgctgagca caccgtgtc acaggtcacg acccagctcg
4357081  gcgagacggc cgctgagctg gcaccccgtg ttgttgcgac ggtgccgcaa ctcgttcagc
4357141  tggctccgca cgccgttcag atgtcgcaaa acgcatcccc catcgctcag acgatcagtc
4357201  aaaccgccca acaggccgcc cagagcgcgc agggcggcag cggcccaatg cccgcacagc
4357261  ttgccagcgc tgaaaaaccg gccaccgagc aagcggagcc ggtccacgaa gtgacaaacg
4357321  acgatcaggg cgaccagggc gacgtgcagc cggccgaggt cgttgccgcg gcacgtgacg
4357381  aaggcgccgg cgcatcaccg ggccagcagc ccggcggggg cgttcccgcg caagccatgg
4357441  ataccggagc cggtgcccgc ccagcggcga gtccgctggc ggcccccgtc gatccgtcga
4357501  ctccggcacc ctcaacaacc acaacgttgt agaccgggcc tgccagcggc tccgtctcgc
4357561  acgcagcgcc tgttgctgtc ctggcctcgt cagcatgcgg cggccagggc ccggtcgagc
4357621  aacccggtga cgtattgcca gtacagccag tccgcgacgg ccacacgctg gacggccgcg
4357681  tcagtcgcag tgtgcgcttg gtgcagggca atctcctgtg agtgggcagc gtaggcccgg
4357741  aacgcccgca gatgagcggc ctcgcggccg gtagcggtgc tggtcatggg cttcatcagc
4357801  tcgaaccaca gcatgtgccg ctcatcgccc ggtggattga catccaccgg cgccggcggc
4357861  aacaagtcga gcaaacgctg atcggtagtg tcgccagct gagccgccgc cgagggggtcg
4357921  acgacctcca gccgcgaccg gcccgtcatt ttgccgctct ccggaatgtc atctggctcc
4357981  agcacaatct tggccacacc gggatccgaa ctggccaact gctccgcggt accgatcacc
4358041  gcccgcagcg tcatgtcgtg gaaagccgcc caggcttgca cggccaaaac cgggtaggtg
4358101  gcacagcgtg caatttcgtc aaccgggatt gcgtgatccg cgctggccaa gtacaccta
4358161  ttcggcaatt ccatcccgtc gggtatgtag gccagcccat agctgttggc cacgacgatg
4358221  gaaccgtcgg tggtcaccgc ggtgatccag aagaacccgt agtcgcccgc gttgttgtcg
4358281  gacgcgttga gcgccgccgc gatgcgtcgc gccaaccgca gcgcatcacc gcggccacgc
4358341  tggcgggcgc tggcagctgc agtggcggcg tcgcgtgccg cccgagccgc cgacaccggg
4358401  atcatcgaca ccggcgtacc gtcatctgca gactcgctgc gatcgggttt gtcgatgtga
```

```
4358461 tcggtcgacg gcgggcgggc aggaggtgcc gtccgcgccg aggccgcccg cgtgctcggt 4358521 gccgccgcct tgtccgaggt agccaccggc gcccgcccag tggcagcatg cgacccgcgc 4358581 cccgaggccg cggccgtacc cacgctcgaa cgcgcgcccg ctcccacggc ggtaccgctc 4358641 ggcgcggcgg ccgccgcccg tgcgcccggg acaccggacg ccgcagccgg cgtcaccgac 4358701 gcggcggatt cgtccgcatg ggcaggcccc gactgcgtcc ccccgcccgc atgctggccc 4358761 ggcacaccag gttgctccgc caacgccgcg ggtttgacgt gcggcgccgg ctcgcccct 4358821 ggggtgcccg gtgttgctgg accagacgga ccgggaaagg ccggtgtaac cggctggggc 4358881 ccaggcgatg gcgccggtgc cggagccggc tgcgggtgtg gagcgggagc tggggtaacg 4358941 ggcgtggccg gggttgccgg tgtggccggg gcgaccgggg gggtgaccgg cgtgatcggg 4359001 gttggctcgc ctggtgtgcc cggtttgacc ggggtcaccg gggtgaccgg cttgccgggg 4359061 gtcaccggcg tgacgggagt gccgggcgtt ggtgtgatcg gagttaccgg cgctcccggg 4359121 atgggtgtga ttggggttcc cggggtgatc ggggttcccg gggtgatcgg ggttcccggt 4359181 gtgccggtg tgcccgggga tggcacgacc agggtaggca cgtctggggg tggcggcgac 4359241 ttctgctgaa gcaaatcctc gagtgcgttc ttcggaggtt tccaattctt ggattccagc 4359301 acccgctcag cggtctcggc gaccagactg acattggccc catgcgtcgc cgtgaccaat 4359361 gaattgatgg cggtatggcg ctcatcagca tccaggctag ggtcattctc caggatatcg 4359421 atctcccgtt gagcgccatc cacattattg ccgatatcgg atttagcttg ctcaatcaac 4359481 ccggcaatat gcctgtgcca ggtaatcacc gtggcgagat aatcctgcag cgtcatcaat 4359541 tgattgatgt ttgcacccag ggcgccgttg gcagcattgg cggcgccgcc ggaccatagg 4359601 ccgccttcga agacgtggcc tttctgctgg cggcaggtgt ccaatacatc ggtgaccctt 4359661 tgcaaaacct ggctatattc ctgggcccgg tcatagaaag tgtcttcatc ggcttc
```

SEQ ID NO:2—A panCD region of *Mycobacterium tuberculosis* H37Rv. Deleted in ΔpanCD strain of Example 2.

```
GGTCTAGCAGCTCGCCCGCGTTTTCGGGCACAAATGCCGGATCGTGGCCC
ATGTCGATCGGTTTGTTGTAAGCGTCGACAAACACGATCCGCGGCTGGTA
TGTGCGGGCCCGGGCGTCGTCCATCGTCGCGTACGCAATCAGAATCACCA
GATCCCCCGGATGCACCAAGTGCGCGGCGGCACCGTTGATGCCAATCACA
CCACTGCCGCGTCGCCGGTGATCGCGTAGGTGACCAGTCGAGCACCGTTG
TCGATATCGACGATGGTTACCTGTTCGCCTTCCAGCAGGTCGGCGGCGTC
CATCAAGTCGGCATCGATGGTCACCGAGCCGACGTAGTGCAGGTCGGCGC
AGGTCACCGTGGCGCGGTGGATCTTCGACTTCAGCATCGTCCGTAACATC
AGTTTCTCCAATGTGATTCGAGGATTGCCCGGTATCCGTCCGGGCGGTCG
GTGCCCGGCGAAAGTTCCGATTTCAATCGCAATGTTGTCCAGCAGCCTGG
TGGTGCCAAGCCGGGCAGCAACCAGCAGCCGACCGGAACCGTTGAGCGGC
ATCGGGCCAAGCCCGATATCGCGCAGCTCCAGGTAGTCGACCGCCACGCC
GGGTGCAGCGTCGAGCACCGCACGGGCGGCATCCAGCGCGGCCTGCGCGC
CAGCCGTTGCCGCATGCGCTGCGGCCGTTTAGCGCCGCCGAGAGCGCGAC
GGCCGCCGCACGCTGGGCCGGGTCCAGGTAGCGGTTGCGCGACGACATCG
CCAGCCCGTCGGCTTCGCGCACGGTCGGCACGCCGACCACCGCGACATCG
AGGTTGAAGTCCGCGACCAGCTGCCGGATCAGCACCAGCTGCTGGTAGTC
CTTCTCACCGAAGAACACCCGATCCGGGCGCACGATCTGCAGCAGCTTTA
GCACGACCGTCAGCACGCCGGCGAAATGGGTTTGGCCGCGGGCCGCCCTC
GAGTTCGGCGGCCAACGGACCGGGTTGCACGGTGGTGCGCAGGCCGTCGG
GATACATCGCCGCGGTAGTTGGCGTGAAAGCGATTTCCACGCCTTCGGCC
CGCAGTTGCGCCAGGTCGTCGTCCGGGGTGCGGGGGATAGGCGTCGAGAT
CTTCCCCCGGCACCGAATTGCATCGGGTTGACGAAGATCGACACGACGAC
GACCGATCCGGGCACCCGCTTGGCCGCACGCACCAACGCGAGGTGGCCTT
CGTGCAGCGCACCCATAGTAGGCAGCAACATCACTCGCCGGCCGGTGAGT
CGCAGTGCGCGACTGACATCGGCGACATCCCCCGGTGCCGAGTACACATT
GA
```

SEQ ID NO:3—A nadBC region of *Mycobacterium tuberculosis* H37Rv. Deleted in ΔnadBC strain of Example 2.

```
AACGGGCGATGAGCCGGGACGCGTCGATGTACCGCGCCGCCGCCGGGCTG
CACCGGACTGTGCGACAGCCTATCCGGAGCACAGGTTCGCGACGTGGCTT
GTCGCCGCGATTTCGAGGACGTGGCGCTCACGCTGGTCGCGCAGAGCGTG
ACCGCCGCCGCCTTGGCCCGCACCGAAAGCCGTGGCTGCCATCATCGCGC
```

-continued

```
GGAGTACCCGTGCACCGTGCCGGAGCAGGCACGCAGCATCGTGGTCCGGG
GAGCCGACGACGCAAATGCGGTGTGTGTCCAGGCGCTAGTGGCGGTGTGC
TGATGGGGTTATCCGACTGGGAGCTGGCTGCGGCTCGAGCAGCAATCGCG
CGTGGGCTCGACGAGGACCTCCGGTACGGCCCGGATGTCACCACATTGGC
GACGGTGCCTGCCAGTGCGACGACCACCGCATCGCTGGTGACCCGGGAGG
CCGGTGTGGTTGCCGGATTGGATGTCGCGCTGCTGACGCTGAACGAAGTC
CTGGGCACCAACGGTTATCGGGTGCTCGACCGCGTCGAGGACGGCGCCCG
GGTGCCGCCGGGAGAGGCACTTATGACGCTGGAAGCCCAAACGCGCGGAT
TGTTGACCGCCGAGCGCACCATGTTGAACCTGGTCGGTCACCTGTCGGGA
ATCGCCACCGCGACGGCCGCGTGGGTCGATGCTGTGCGCGGGACCAAAGC
GAAAATCCGCGATACCCGTAAGACGCTGCCCGGCCTGCGCGCGCTGCAAA
AATACGCGGTGCGTACCGGTGG
```

SEQ ID NO:4 lysA sequence in ΔlysA strains

```
GTGAACGAGCTGCTGCACTTAGCGCCGAATGTGTGGCCGCGCAATACTAC
TCGCGATGAAGTCGGTGTGGTCTGCATCGCAGGAATTCCACTGACGCAGC
TCGCCCAGGAGTACGGGACCCCGCTGTTCGTCATCGACGAGGACGACTTT
CGCTCGCGCTGCCGAGAAACCGCCGCGGCCTTTGGAAGTGGGGCGAACGT
GCACTATGCCGCCAAGGCGTTCCTGTGCAGCGAAGTAGCCCGGTGGATCA
GCGAAGAAGGGCTCTGTCTGGACCTTTGCACCGGTGGGGAGTTGGCGGTC
GCGCTGCACGCTAGCTTTCCGCCCGAGCGAATTACCTTGCACGGCAACAA
CAAATCGGTCTCAGAGTTGACCGCTGCGGTCAAAGCCGGAGTCGGCCATA
TTGTCGTCGATTCGATGACCGAGATCGAGCGCCTCGACGCCATCGCGGGC
GAGGCCGGAATCGTCCAGGATGTCCTGGTGCGTCTCACCGTCGGTGTCGA
GGCGCACACCCACGAGTTCATCTCCACCGCGCACGAGACGCGTCAGCCAC
ATCGGTTCGCAGATCTTCGACGTGGACGGCTTCGAACTCGCCGCGCACCG
TGTCATCGGCCTGCTACGCGACGTCGTCGGCGAGTTCGGTCCCGAAAAGA
CGGCACAGATCGCGACCGTCGATCTCGGTGGCGGCTTGGGCATCTCGTAT
TGCCGTCCGACGACCCACCGCCGATAGCCGAGCTCGCGGCCAAGCTGGGT
ACCATCGTGAGCGACGAGTCAACGGCCGTGGGGCTGACCGACGCCCAAGC
TCCGTTGTGGAGCCCGGACGCGCCATCGCCGACCGGGCACCATCACGTG
TATGAGGTCGGCACCGTTAAGGACGTCGATGTCAGCGCCACAGCGCATCG
ACGTTACGTCAGTGTCGACGGCGGCATGAGCGACAACATCCGCACCGCGC
TCTACGGCGCGCAGTATGACGTCCGGCTGGTGTCTCGAGTCAGCGACGCC
CCGCCGGTACCGGCCCGTCTGGTCGGAAAGCACTGCGAAAGTGGCGATAT
CATCGTGCGGGACACCTGGGTGCCCGACGATATTCGGCCCGGCGATCTGG
TTGCGGTTTGCCGCCACCGGCGCTACTGCTTTCGCTGTCGAGTCGTTACA
ACATGGTCGGCCGTCCCGCTGTGGTAGCGGTGCACGCGGGCAACGCTCGC
CTGGTCCTGCGTCGGGAGACGGTCGACGATTTGCTGAGTTTGGAAGTGAG
GTGA
```

SEQ ID NO:5 leuD sequence, deleted in ΔleuD strains

```
GGGGGCGGGTAGAGTGCGCGGTTTCCAGTACGCGCACGCACCCTCAAAGG
CCTCGATCTCGTCGAGTTCCGCAGCGTAAGGGCTATATCGTCGAGACCTT
TCAAGCAGCCGCCACGCCGAGTGGTCGTCAATCTTGAACGGCAGCACCAC
TGTTTGCTGCGGTGATAATCGATCTTGAAGATTGGCAGTGATTCCAGGCC
CGGACTCTGCTCAATGAGCTTCCACAGGAGTTCCACATCGTCTTGGGCAA
CCTCGGCCGCCAGCAGCCCGGCTTGCCCGCGTTGCCGCGGAAAATGTCAC
CAAATCGGGATGAGATAACCACCCGGAATCCGTAGTCCATGAGCGCCCAG
ACCGCAT
```

What is claimed is:

1. A non-naturally occurring *Mycobacterium tuberculosis* auxotrophic for leucine and pantothenate, wherein the *M. tuberculosis* exhibits attenuated virulence in a mammal when compared to the *M. tuberculosis* without the leucine and pantothenate auxotrophy.

2. The *M. tuberculosis* of claim 1, wherein the leucine auxotrophy is due to a deletion in a leuD gene.

3. The *M. tuberculosis* of claim 2, wherein the deleted region of the leuD gene has at least 95% homology to SEQ ID NO:5.

4. The *M. tuberculosis* of claims 1, wherein the pantothenate auxotrophy is due to a deletion in a panCD gene.

5. The *M. tuberculosis* of claim 4, wherein the deleted region of the panCD gene has at least 95% homology to SEQ ID NO:2.

6. The *M. tuberculosis* of claim 1, wherein the leucine auxotrophy is due to a deletion in a leuD gene and the pantothenate auxotrophy is due to a deletion in a panCD gene.

7. The *M. tuberculosis* of claim 6, wherein the deleted region of the leuD gene has at least 95% homology to SEQ ID NO:5 and the deleted region of the panCD gene has at least 95% homology to SEQ ID NO:2.

8. A mycobacterium in the *Mycobacterium tuberculosis* complex, genetically engineered to comprise a deletion causing leucine auxotrophy and a deletion causing pantothenate auxotrophy.

9. The mycobacterium of claim 8, wherein the deletion causing leucine auxotrophy is from a leuD gene and the deletion causing pantothenate auxotrophy is from a panCD gene.

10. The mycobacterium of claim 8, wherein the mycobacterium is a *Mycobacterium bovis*.

11. The mycobacterium of claim 8, wherein the mycobacterium is a *Mycobacterium tuberculosis*.

12. The mycobacterium of claim 9, wherein the deletion of the leuD gene has at least 95% homology to SEQ ID NO:5.

13. The mycobacterium of claim 9, wherein the deletion of the panCD gene has at least 95% homology to SEQ ID NO:2.

14. The mycobacterium of claim 9, wherein the deletion of the leuD gene has at least 95% homology to SEQ ID NO:5 and the deletion of the panCD gene has at least 95% homology to SEQ ID NO:2.

15. A tuberculosis vaccine comprising the *M. tuberculosis* of claim 1 in a pharmaceutically acceptable excipient, wherein the vaccine is capable of protecting a mammal from challenge by a virulent *M. tuberculosis*.

16. A tuberculosis vaccine comprising the mycobacterium of claim 11 in a pharmaceutically acceptable excipient, wherein the vaccine is capable of protecting a mammal from challenge by a virulent *M. tuberculosis*.

* * * * *